US010894959B2

(12) United States Patent
Cox et al.

(10) Patent No.: US 10,894,959 B2
(45) Date of Patent: Jan. 19, 2021

(54) VARIANT LIBRARIES OF THE IMMUNOLOGICAL SYNAPSE AND SYNTHESIS THEREOF

(71) Applicant: TWIST BIOSCIENCE CORPORATION, San Francisco, CA (US)

(72) Inventors: Anthony Cox, Mountain View, CA (US); Siyuan Chen, San Mateo, CA (US)

(73) Assignee: TWIST BIOSCIENCE CORPORATION, San Francisco, CA (US)

(*) Notice: Subject to any disclaimer, the term of this patent is extended or adjusted under 35 U.S.C. 154(b) by 62 days.

(21) Appl. No.: 15/921,537

(22) Filed: Mar. 14, 2018

(65) Prior Publication Data

US 2018/0273936 A1   Sep. 27, 2018

Related U.S. Application Data

(60) Provisional application No. 62/471,810, filed on Mar. 15, 2017.

(51) Int. Cl.
C12N 15/10 (2006.01)
C12Q 1/6806 (2018.01)

(52) U.S. Cl.
CPC ....... *C12N 15/1093* (2013.01); *C12Q 1/6806* (2013.01)

(58) Field of Classification Search
None
See application file for complete search history.

(56) References Cited

U.S. PATENT DOCUMENTS

| | | |
|---|---|---|
| 3,549,368 A | 12/1970 | Robert et al. |
| 3,920,714 A | 11/1975 | Streck |
| 4,123,661 A | 10/1978 | Wolf et al. |
| 4,415,732 A | 11/1983 | Caruthers et al. |
| 4,613,398 A | 9/1986 | Chiong et al. |
| 4,726,877 A | 2/1988 | Fryd et al. |
| 4,808,511 A | 2/1989 | Holmes |
| 4,837,401 A | 6/1989 | Hirose et al. |
| 4,863,557 A | 9/1989 | Kokaku et al. |
| 4,981,797 A | 1/1991 | Jessee et al. |
| 4,988,617 A | 1/1991 | Landegren et al. |
| 5,102,797 A | 4/1992 | Tucker et al. |
| 5,118,605 A | 6/1992 | Urdea |
| 5,137,814 A | 8/1992 | Rashtchian et al. |
| 5,143,854 A | 9/1992 | Pirrung et al. |
| 5,242,794 A | 9/1993 | Whiteley et al. |
| 5,242,974 A | 9/1993 | Holmes |
| 5,288,514 A | 2/1994 | Ellman |
| 5,291,897 A | 3/1994 | Gastrin et al. |
| 5,299,491 A | 4/1994 | Kawada |
| 5,384,261 A | 1/1995 | Winkler et al. |
| 5,387,541 A | 2/1995 | Hodge et al. |
| 5,395,753 A | 3/1995 | Prakash |
| 5,431,720 A | 7/1995 | Nagai et al. |
| 5,445,934 A | 8/1995 | Fodor et al. |
| 5,449,754 A | 9/1995 | Nishioka |
| 5,459,039 A | 10/1995 | Modrich et al. |
| 5,474,796 A | 12/1995 | Brennan |
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes |
| 5,530,516 A | 6/1996 | Sheets |

(Continued)

FOREIGN PATENT DOCUMENTS

| | | |
|---|---|---|
| AU | 3157000 A | 9/2000 |
| CA | 2362939 A1 | 8/2000 |

(Continued)

OTHER PUBLICATIONS

Rajpal et al., "A general method for greatly improving the affinity of antibodies by using combinatorial libraries," Proc. Natl. Acad. Sci. USA 2005, 102(24):8466-8471. (Year: 2005).*
Eroshenko et al.: Gene Assembly from Chip-Synthesized Oligonucleotides; Current Protocols in Chemical biology 4: 1-17 (2012).
European Patent Application No. 16871446.7 First Official Action dated Nov. 13, 2019.
Galka et al.: QuickLib, a method for building fully synthetic plasmid libraries by seamless cloning of degenerate oligonucleotides. PLOS ONE, 12, e0175146:1-9 (2017).
Galka et al.: QuickLib, a method for building fully synthetic plasmid libraries by seamless cloning of degenerate oligonucleotides. PLOS ONE, 12, e0175146:S1 figure (2017).

(Continued)

*Primary Examiner* — Kaijiang Zhang
(74) *Attorney, Agent, or Firm* — Wilson Sonsini Goodrich & Rosati

(57) ABSTRACT

Disclosed herein are methods for the generation of highly accurate nucleic acid libraries encoding for predetermined variants of a nucleic acid sequence. The nucleic acid sequence may encode for all or part of a reference domain of a CAR. The degree of variation may be complete, resulting in a saturated variant library, or less than complete, resulting in a non-saturating library of variants. The variant nucleic acid libraries described herein may be designed for further processing by transcription or translation. The variant nucleic acid libraries described herein may be designed to generate variant RNA, DNA and/or protein populations. Further provided herein are method for identifying variant species with increased or decreased activities, with applications in regulating biological functions and the design of therapeutics for treatment or reduction of a disease, such as cancer.

13 Claims, 21 Drawing Sheets

Specification includes a Sequence Listing.

(56) References Cited

U.S. PATENT DOCUMENTS

| | | |
|---|---|---|
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,683,879 A | 11/1997 | Laney et al. |
| 5,688,642 A | 11/1997 | Chrisey et al. |
| 5,700,637 A | 12/1997 | Southern |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,739,386 A | 4/1998 | Holmes |
| 5,750,672 A | 5/1998 | Kempe |
| 5,780,613 A | 7/1998 | Letsinger et al. |
| 5,830,643 A | 11/1998 | Yamamoto et al. |
| 5,830,655 A | 11/1998 | Monforte et al. |
| 5,830,662 A | 11/1998 | Soares et al. |
| 5,834,252 A | 11/1998 | Stemmer et al. |
| 5,843,669 A | 12/1998 | Kaiser et al. |
| 5,843,767 A | 12/1998 | Beattie |
| 5,846,717 A | 12/1998 | Brow et al. |
| 5,854,033 A | 12/1998 | Lizardi |
| 5,858,754 A | 1/1999 | Modrich et al. |
| 5,861,482 A | 1/1999 | Modrich et al. |
| 5,863,801 A | 1/1999 | Southgate et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 5,962,272 A | 10/1999 | Chenchik et al. |
| 5,976,842 A | 11/1999 | Wurst |
| 5,976,846 A | 11/1999 | Passmore et al. |
| 5,989,872 A | 11/1999 | Luo et al. |
| 5,994,069 A | 11/1999 | Hall et al. |
| 6,001,567 A | 12/1999 | Brow et al. |
| 6,008,031 A | 12/1999 | Modrich et al. |
| 6,013,440 A | 1/2000 | Lipshutz et al. |
| 6,015,674 A | 1/2000 | Woudenberg et al. |
| 6,017,434 A | 1/2000 | Simpson et al. |
| 6,020,481 A | 2/2000 | Benson et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,087,482 A | 7/2000 | Teng et al. |
| 6,090,543 A | 7/2000 | Prudent et al. |
| 6,090,606 A | 7/2000 | Kaiser et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,130,045 A | 10/2000 | Wurst et al. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,274,725 B1 | 8/2001 | Sanghvi et al. |
| 6,284,465 B1 | 9/2001 | Wolber |
| 6,287,776 B1 | 9/2001 | Hefti |
| 6,287,824 B1 | 9/2001 | Lizardi |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,312,911 B1 | 11/2001 | Bancroft et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |
| 6,399,394 B1 | 6/2002 | Dahm et al. |
| 6,399,516 B1 | 6/2002 | Ayon |
| 6,403,314 B1 | 6/2002 | Lange et al. |
| 6,406,849 B1 | 6/2002 | Dorsel et al. |
| 6,406,851 B1 | 6/2002 | Bass |
| 6,408,308 B1 | 6/2002 | Maslyn et al. |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |
| 6,458,526 B1 | 10/2002 | Schembri et al. |
| 6,458,535 B1 | 10/2002 | Hall et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,472,147 B1 | 10/2002 | Janda et al. |
| 6,492,107 B1 | 12/2002 | Kauffman et al. |
| 6,518,056 B2 | 2/2003 | Schembri et al. |
| 6,521,427 B1 | 2/2003 | Evans |
| 6,521,453 B1 | 2/2003 | Crameri et al. |
| 6,555,357 B1 | 4/2003 | Kaiser et al. |
| 6,558,908 B2 | 5/2003 | Wolber et al. |
| 6,562,611 B1 | 5/2003 | Kaiser et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | Van et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,642,373 B2 | 11/2003 | Manoharan et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B1 | 12/2003 | Wengel et al. |
| 6,673,552 B2 | 1/2004 | Frey |
| 6,682,702 B2 | 1/2004 | Barth et al. |
| 6,689,319 B1 | 2/2004 | Fisher et al. |
| 6,692,917 B2 | 2/2004 | Neri et al. |
| 6,702,256 B2 | 3/2004 | Killeen et al. |
| 6,706,471 B1 | 3/2004 | Brow et al. |
| 6,706,875 B1 | 3/2004 | Goldberg et al. |
| 6,709,852 B1 | 3/2004 | Bloom et al. |
| 6,709,854 B2 | 3/2004 | Donahue et al. |
| 6,713,262 B2 | 3/2004 | Gillibolian et al. |
| 6,716,629 B2 | 4/2004 | Hess et al. |
| 6,716,634 B1 | 4/2004 | Myerson |

(56) References Cited

U.S. PATENT DOCUMENTS

| | | |
|---|---|---|
| 6,723,509 B2 | 4/2004 | Ach |
| 6,728,129 B2 | 4/2004 | Lindsey et al. |
| 6,743,585 B2 | 6/2004 | Dellinger et al. |
| 6,753,145 B2 | 6/2004 | Holcomb et al. |
| 6,768,005 B2 | 7/2004 | Mellor et al. |
| 6,770,748 B2 | 8/2004 | Imanishi et al. |
| 6,770,892 B2 | 8/2004 | Corson et al. |
| 6,773,676 B2 | 8/2004 | Schembri |
| 6,773,888 B2 | 8/2004 | Li et al. |
| 6,780,982 B2 | 8/2004 | Lyamichev et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | Celsa |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | De et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,951,719 B1 | 10/2005 | Dupret et al. |
| 6,958,119 B1 | 10/2005 | Yin et al. |
| 6,960,464 B2 | 11/2005 | Jessee et al. |
| 6,969,449 B2 | 11/2005 | Maher et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 6,991,922 B2 | 1/2006 | Dupret et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,041,445 B2 | 5/2006 | Chenchik et al. |
| 7,045,289 B2 | 5/2006 | Allawi et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Staehler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,122,364 B1 | 10/2006 | Lyamichev et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,150,982 B2 | 12/2006 | Allawi et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |
| 7,193,077 B2 | 3/2007 | Dellinger et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,217,522 B2 | 5/2007 | Brenner |
| 7,220,573 B2 | 5/2007 | Shea et al. |
| 7,221,785 B2 | 5/2007 | Curry et al. |
| 7,226,862 B2 | 6/2007 | Staehler et al. |
| 7,227,017 B2 | 6/2007 | Mellor et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,276,599 B2 | 10/2007 | Moore et al. |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,306,917 B2 | 12/2007 | Prudent et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |
| 7,371,519 B2 | 5/2008 | Wolber et al. |
| 7,371,580 B2 | 5/2008 | Yakhini et al. |
| 7,372,982 B2 | 5/2008 | Le |
| 7,384,746 B2 | 6/2008 | Lyamichev et al. |
| 7,385,050 B2 | 6/2008 | Dellinger et al. |
| 7,390,457 B2 | 6/2008 | Schembri |
| 7,393,665 B2 | 7/2008 | Brenner |
| 7,396,676 B2 | 7/2008 | Robotti et al. |
| 7,399,844 B2 | 7/2008 | Sampson et al. |
| 7,402,279 B2 | 7/2008 | Schembri |
| 7,411,061 B2 | 8/2008 | Myerson et al. |
| 7,413,709 B2 | 8/2008 | Roitman et al. |

(56) References Cited

U.S. PATENT DOCUMENTS

| | | |
|---|---|---|
| 7,417,139 B2 | 8/2008 | Dellinger et al. |
| 7,422,911 B2 | 9/2008 | Schembri |
| 7,427,679 B2 | 9/2008 | Dellinger et al. |
| 7,432,048 B2 | 10/2008 | Neri et al. |
| 7,435,810 B2 | 10/2008 | Myerson et al. |
| 7,439,272 B2 | 10/2008 | Xu |
| 7,476,709 B2 | 1/2009 | Moody et al. |
| 7,482,118 B2 | 1/2009 | Allawi et al. |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |
| 7,524,942 B2 | 4/2009 | Wang et al. |
| 7,524,950 B2 | 4/2009 | Dellinger et al. |
| 7,527,928 B2 | 5/2009 | Neri et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,541,145 B2 | 6/2009 | Prudent et al. |
| 7,544,473 B2 | 6/2009 | Brenner |
| 7,556,919 B2 | 7/2009 | Chenchik et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |
| 7,604,996 B1 | 10/2009 | Stuelpnagel et al. |
| 7,608,396 B2 | 10/2009 | Delenstarr |
| 7,618,777 B2 | 11/2009 | Myerson et al. |
| 7,629,120 B2 | 12/2009 | Bennett et al. |
| 7,635,772 B2 | 12/2009 | McCormac |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,678,542 B2 | 3/2010 | Lyamichev et al. |
| 7,682,809 B2 | 3/2010 | Sampson |
| 7,709,197 B2 | 5/2010 | Drmanac |
| 7,718,365 B2 | 5/2010 | Wang |
| 7,718,786 B2 | 5/2010 | Dupret et al. |
| 7,723,077 B2 | 5/2010 | Young et al. |
| 7,737,088 B1 | 6/2010 | Staehler et al. |
| 7,737,089 B2 | 6/2010 | Guimil et al. |
| 7,741,463 B2 | 6/2010 | Gormley et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,776,532 B2 | 8/2010 | Gibson et al. |
| 7,790,369 B2 | 9/2010 | Stahler et al. |
| 7,790,387 B2 | 9/2010 | Dellinger et al. |
| 7,807,356 B2 | 10/2010 | Sampson et al. |
| 7,807,806 B2 | 10/2010 | Allawi et al. |
| 7,811,753 B2 | 10/2010 | Eshoo |
| 7,816,079 B2 | 10/2010 | Fischer |
| 7,820,387 B2 | 10/2010 | Neri et al. |
| 7,829,314 B2 | 11/2010 | Prudent et al. |
| 7,855,281 B2 | 12/2010 | Dellinger et al. |
| 7,862,999 B2 | 1/2011 | Zheng et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,935,800 B2 | 5/2011 | Allawi et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,842 B2 | 9/2011 | Brenner |
| 8,021,844 B2 | 9/2011 | Wang |
| 8,034,917 B2 | 10/2011 | Yamada |
| 8,036,835 B2 | 10/2011 | Sampas et al. |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |
| 8,063,184 B2 | 11/2011 | Allawi et al. |
| 8,067,556 B2 | 11/2011 | Hogrefe et al. |
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,137,936 B2 | 3/2012 | Macevicz |
| 8,148,068 B2 | 4/2012 | Brenner |
| 8,154,729 B2 | 4/2012 | Baldo et al. |
| 8,168,385 B2 | 5/2012 | Brenner |
| 8,168,388 B2 | 5/2012 | Gormley et al. |
| 8,173,368 B2 | 5/2012 | Staehler et al. |
| 8,182,991 B1 | 5/2012 | Kaiser et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett |
| 8,263,335 B2 | 9/2012 | Carr et al. |
| 8,268,605 B2 | 9/2012 | Sorge et al. |
| 8,283,148 B2 | 10/2012 | Sorge et al. |
| 8,288,093 B2 | 10/2012 | Hall et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,383,338 B2 | 2/2013 | Kitzman et al. |
| 8,415,138 B2 | 4/2013 | Leproust |
| 8,435,736 B2 | 5/2013 | Gibson et al. |
| 8,445,205 B2 | 5/2013 | Brenner |
| 8,445,206 B2 | 5/2013 | Bergmann et al. |
| 8,470,996 B2 | 6/2013 | Brenner |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,497,069 B2 | 7/2013 | Hutchison, III et al. |
| 8,500,979 B2 | 8/2013 | Elibol et al. |
| 8,501,454 B2 | 8/2013 | Liu et al. |
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,563,478 B2 | 10/2013 | Gormley et al. |
| 8,569,046 B2 | 10/2013 | Love et al. |
| 8,577,621 B2 | 11/2013 | Troup et al. |
| 8,586,310 B2 | 11/2013 | Mitra et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |

(56) References Cited

U.S. PATENT DOCUMENTS

| | | |
|---|---|---|
| 8,669,053 B2 | 3/2014 | Stuelpnagel et al. |
| 8,679,756 B1 | 3/2014 | Brenner et al. |
| 8,685,642 B2 | 4/2014 | Sampas |
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |
| 8,808,896 B2 | 8/2014 | Choo et al. |
| 8,808,986 B2 | 8/2014 | Jacobson et al. |
| 8,815,600 B2 | 8/2014 | Liu et al. |
| 8,889,851 B2 | 11/2014 | Leproust et al. |
| 8,932,994 B2 | 1/2015 | Gormley et al. |
| 8,962,532 B2 | 2/2015 | Shapiro et al. |
| 8,968,999 B2 | 3/2015 | Gibson et al. |
| 8,980,563 B2 | 3/2015 | Zheng et al. |
| 9,018,365 B2 | 4/2015 | Brenner |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,328,378 B2 | 5/2016 | Earnshaw et al. |
| 9,347,091 B2 | 5/2016 | Bergmann et al. |
| 9,375,748 B2 | 6/2016 | Harumoto et al. |
| 9,376,677 B2 | 6/2016 | Mir |
| 9,376,678 B2 | 6/2016 | Gormley et al. |
| 9,384,320 B2 | 7/2016 | Church |
| 9,384,920 B1 | 7/2016 | Bakulich |
| 9,388,407 B2 | 7/2016 | Jacobson |
| 9,394,333 B2 | 7/2016 | Wada et al. |
| 9,403,141 B2 | 8/2016 | William |
| 9,409,139 B2 | 8/2016 | Banyai et al. |
| 9,410,149 B2 | 8/2016 | Brenner et al. |
| 9,410,173 B2 | 8/2016 | Betts et al. |
| 9,416,411 B2 | 8/2016 | Stuelpnagel et al. |
| 9,422,600 B2 | 8/2016 | Ramu et al. |
| 9,487,824 B2 | 11/2016 | Kutyavin et al. |
| 9,499,848 B2 | 11/2016 | Carr et al. |
| 9,523,122 B2 | 12/2016 | Zheng et al. |
| 9,528,148 B2 | 12/2016 | Zheng et al. |
| 9,534,251 B2 | 1/2017 | Young et al. |
| 9,555,388 B2 | 1/2017 | Banyai et al. |
| 9,568,839 B2 | 2/2017 | Stahler et al. |
| 9,580,746 B2 | 2/2017 | Leproust et al. |
| 9,670,529 B2 | 6/2017 | Osborne et al. |
| 9,670,536 B2 | 6/2017 | Casbon et al. |
| 9,677,067 B2 | 6/2017 | Toro et al. |
| 9,695,211 B2 | 7/2017 | Wada et al. |
| 9,718,060 B2 | 8/2017 | Venter et al. |
| 9,745,573 B2 | 8/2017 | Stuelpnagel et al. |
| 9,745,619 B2 | 8/2017 | Rabbani et al. |
| 9,765,387 B2 | 9/2017 | Rabbani et al. |
| 9,771,576 B2 | 9/2017 | Gibson et al. |
| 9,833,761 B2 | 12/2017 | Banyai et al. |
| 9,834,774 B2 | 12/2017 | Carstens |
| 9,839,894 B2 | 12/2017 | Banyai et al. |
| 9,879,283 B2 | 1/2018 | Ravinder et al. |
| 9,889,423 B2 | 2/2018 | Banyai et al. |
| 9,895,673 B2 | 2/2018 | Peck et al. |
| 9,925,510 B2 | 3/2018 | Jacobson et al. |
| 9,932,576 B2 | 4/2018 | Raymond et al. |
| 9,981,239 B2 | 5/2018 | Banyai et al. |
| 10,053,688 B2 | 8/2018 | Cox |
| 10,384,188 B2 | 8/2019 | Banyai et al. |
| 10,583,415 B2 | 3/2020 | Banyai et al. |
| 10,618,024 B2 | 4/2020 | Banyai et al. |
| 10,632,445 B2 | 4/2020 | Banyai et al. |
| 10,669,304 B2 | 6/2020 | Indermuhle et al. |
| 10,754,994 B2 | 8/2020 | Peck |
| 10,773,232 B2 | 9/2020 | Banyai et al. |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0025561 A1 | 2/2002 | Hodgson |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths et al. |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van et al. |
| 2003/0022207 A1 | 1/2003 | Balasubramanian et al. |
| 2003/0022240 A1 | 1/2003 | Luo et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0082719 A1 | 5/2003 | Schumacher et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du |
| 2004/0009498 A1* | 1/2004 | Short ............... C07K 16/00 435/5 |
| 2004/0043509 A1 | 3/2004 | Stahler et al. |
| 2004/0053362 A1 | 3/2004 | De et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 6/2004 | Xu et al. |
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0213795 A1 | 10/2004 | Collins et al. |
| 2004/0219663 A1 | 11/2004 | Page et al. |
| 2004/0236027 A1 | 11/2004 | Maeji et al. |
| 2004/0248161 A1 | 12/2004 | Rothberg et al. |
| 2004/0259146 A1 | 12/2004 | Friend et al. |
| 2005/0022895 A1 | 2/2005 | Barth et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0112679 A1 | 5/2005 | Myerson et al. |
| 2005/0124022 A1 | 6/2005 | Srinivasan et al. |
| 2005/0137805 A1 | 6/2005 | Lewin et al. |
| 2005/0208513 A1 | 9/2005 | Agbo et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2006/0003381 A1 | 1/2006 | Gilmore et al. |

(56) References Cited

U.S. PATENT DOCUMENTS

| | | |
|---|---|---|
| 2006/0003958 A1 | 1/2006 | Melville et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0127920 A1 | 6/2006 | Church et al. |
| 2006/0134638 A1 | 6/2006 | Mulligan et al. |
| 2006/0160138 A1 | 7/2006 | Church |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2007/0031857 A1 | 2/2007 | Makarov et al. |
| 2007/0031877 A1 | 2/2007 | Stahler et al. |
| 2007/0043516 A1 | 2/2007 | Gustafsson et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099208 A1 | 5/2007 | Drmanac et al. |
| 2007/0122817 A1 | 5/2007 | Church et al. |
| 2007/0141557 A1 | 6/2007 | Raab et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085511 A1 | 4/2008 | Peck et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0300842 A1 | 12/2008 | Govindarajan et al. |
| 2008/0308884 A1 | 12/2008 | Kalvesten |
| 2008/0311628 A1 | 12/2008 | Shoemaker |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0246788 A1 | 10/2009 | Albert et al. |
| 2009/0263802 A1 | 10/2009 | Drmanac |
| 2009/0285825 A1 | 11/2009 | Kini et al. |
| 2009/0324546 A1 | 12/2009 | Notka et al. |
| 2010/0004143 A1 | 1/2010 | Shibahara |
| 2010/0009872 A1 | 1/2010 | Eid et al. |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0099103 A1 | 4/2010 | Hsieh et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0286290 A1 | 11/2010 | Lohmann et al. |
| 2010/0292102 A1 | 11/2010 | Nouri |
| 2010/0300882 A1 | 12/2010 | Zhang et al. |
| 2011/0009607 A1 | 1/2011 | Komiyama et al. |
| 2011/0082055 A1 | 4/2011 | Fox et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0217738 A1 | 9/2011 | Jacobson |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0032366 A1 | 2/2012 | Ivniski et al. |
| 2012/0046175 A1 | 2/2012 | Rodesch et al. |
| 2012/0050411 A1 | 3/2012 | Mabritto et al. |
| 2012/0094847 A1 | 4/2012 | Warthmann et al. |
| 2012/0128548 A1 | 5/2012 | West et al. |
| 2012/0129704 A1 | 5/2012 | Gunderson et al. |
| 2012/0149602 A1 | 6/2012 | Friend et al. |
| 2012/0164127 A1 | 6/2012 | Short et al. |
| 2012/0164633 A1 | 6/2012 | Laffler |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005585 A1 | 1/2013 | Anderson et al. |
| 2013/0005612 A1 | 1/2013 | Carr et al. |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0040836 A1 | 2/2013 | Himmler et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0164308 A1 | 6/2013 | Foletti et al. |
| 2013/0196864 A1 | 8/2013 | Govindarajan et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |

(56) References Cited

U.S. PATENT DOCUMENTS

| | | |
|---|---|---|
| 2013/0296192 A1 | 11/2013 | Jacobson et al. |
| 2013/0296194 A1 | 11/2013 | Jacobson et al. |
| 2013/0298265 A1 | 11/2013 | Cunnac et al. |
| 2013/0309725 A1 | 11/2013 | Jacobson et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0031240 A1 | 1/2014 | Behlke et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |
| 2014/0170665 A1 | 6/2014 | Hiddessen et al. |
| 2014/0178992 A1 | 6/2014 | Nakashima et al. |
| 2014/0221250 A1 | 8/2014 | Vasquez et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0056609 A1 | 2/2015 | Daum et al. |
| 2015/0057625 A1 | 2/2015 | Coulthard |
| 2015/0065357 A1 | 3/2015 | Fox |
| 2015/0065393 A1 | 3/2015 | Jacobson |
| 2015/0099870 A1 | 4/2015 | Bennett et al. |
| 2015/0120265 A1 | 4/2015 | Amirav-Drory et al. |
| 2015/0159152 A1 | 6/2015 | Allen et al. |
| 2015/0183853 A1 | 7/2015 | Sharma et al. |
| 2015/0191524 A1 | 7/2015 | Smith et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0240280 A1 | 8/2015 | Gibson et al. |
| 2015/0261664 A1 | 9/2015 | Goldman et al. |
| 2015/0269313 A1 | 9/2015 | Church |
| 2015/0293102 A1 | 10/2015 | Shim |
| 2015/0307875 A1 | 10/2015 | Happe et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0019341 A1 | 1/2016 | Harris et al. |
| 2016/0024138 A1 | 1/2016 | Gebeyehu et al. |
| 2016/0024576 A1 | 1/2016 | Chee et al. |
| 2016/0026753 A1 | 1/2016 | Krishnaswami et al. |
| 2016/0026758 A1 | 1/2016 | Jabara et al. |
| 2016/0032396 A1 | 2/2016 | Diehn et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0089651 A1 | 3/2016 | Banyai |
| 2016/0090592 A1 | 3/2016 | Banyai et al. |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0122800 A1 | 5/2016 | Bernick et al. |
| 2016/0152972 A1 | 6/2016 | Stapleton et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0215283 A1 | 7/2016 | Braman et al. |
| 2016/0229884 A1 | 8/2016 | Indermuhle et al. |
| 2016/0230175 A1 | 8/2016 | Carstens |
| 2016/0230221 A1 | 8/2016 | Bergmann et al. |
| 2016/0251651 A1 | 9/2016 | Banyai et al. |
| 2016/0256846 A1 | 9/2016 | Smith et al. |
| 2016/0264958 A1 | 9/2016 | Toro et al. |
| 2016/0289758 A1 | 10/2016 | Akeson et al. |
| 2016/0289839 A1 | 10/2016 | Harumoto et al. |
| 2016/0303535 A1 | 10/2016 | Banyai et al. |
| 2016/0304862 A1 | 10/2016 | Igawa et al. |
| 2016/0304946 A1 | 10/2016 | Betts et al. |
| 2016/0310426 A1 | 10/2016 | Wu |
| 2016/0310927 A1 | 10/2016 | Banyai et al. |
| 2016/0318016 A1 | 11/2016 | Hou et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0348098 A1 | 12/2016 | Stuelpnagel et al. |
| 2016/0354752 A1 | 12/2016 | Banyai et al. |
| 2016/0355880 A1 | 12/2016 | Gormley et al. |
| 2017/0017436 A1 | 1/2017 | Church |
| 2017/0066844 A1 | 3/2017 | Glanville |
| 2017/0067099 A1 | 3/2017 | Zheng et al. |
| 2017/0073664 A1 | 3/2017 | McCafferty et al. |
| 2017/0073731 A1 | 3/2017 | Zheng et al. |
| 2017/0081660 A1 | 3/2017 | Cox et al. |
| 2017/0081716 A1 | 3/2017 | Peck |
| 2017/0088887 A1 | 3/2017 | Makarov et al. |
| 2017/0095785 A1 | 4/2017 | Banyai et al. |
| 2017/0096706 A1 | 4/2017 | Behlke et al. |
| 2017/0114404 A1 | 4/2017 | Behlke et al. |
| 2017/0141793 A1 | 5/2017 | Strauss et al. |
| 2017/0147748 A1 | 5/2017 | Staehler et al. |
| 2017/0151546 A1 | 6/2017 | Peck et al. |
| 2017/0159044 A1 | 6/2017 | Toro et al. |
| 2017/0175110 A1 | 6/2017 | Jacobson et al. |
| 2017/0218537 A1 | 8/2017 | Olivares |
| 2017/0233764 A1 | 8/2017 | Young et al. |
| 2017/0247473 A1 | 8/2017 | Short |
| 2017/0249345 A1 | 8/2017 | Malik et al. |
| 2017/0253644 A1 | 9/2017 | Steyaert et al. |
| 2017/0320061 A1 | 11/2017 | Venter et al. |
| 2017/0327819 A1 | 11/2017 | Banyai et al. |
| 2017/0355984 A1 | 12/2017 | Evans et al. |
| 2017/0357752 A1 | 12/2017 | Diggans |
| 2017/0362589 A1 | 12/2017 | Banyai et al. |
| 2018/0029001 A1 | 2/2018 | Banyai |
| 2018/0051278 A1 | 2/2018 | Cox et al. |
| 2018/0051280 A1 | 2/2018 | Gibson et al. |
| 2018/0068060 A1 | 3/2018 | Ceze et al. |
| 2018/0101487 A1 | 4/2018 | Peck |
| 2018/0104664 A1 | 4/2018 | Fernandez |
| 2018/0126355 A1 | 5/2018 | Peck et al. |
| 2018/0142289 A1 | 5/2018 | Zeitoun |
| 2018/0171509 A1 | 6/2018 | Cox |
| 2018/0236425 A1 | 8/2018 | Banyai et al. |
| 2018/0253563 A1 | 9/2018 | Peck et al. |
| 2018/0264428 A1 | 9/2018 | Banyai et al. |
| 2018/0282721 A1 | 10/2018 | Cox et al. |
| 2018/0312834 A1 | 11/2018 | Cox et al. |
| 2018/0326388 A1 | 11/2018 | Banyai et al. |
| 2018/0346585 A1 | 12/2018 | Zhang et al. |
| 2018/0355351 A1 | 12/2018 | Nugent et al. |
| 2019/0060345 A1 | 2/2019 | Harrison et al. |
| 2019/0118154 A1 | 4/2019 | Marsh et al. |
| 2019/0135926 A1 | 5/2019 | Glanville |
| 2019/0240636 A1 | 8/2019 | Peck et al. |
| 2019/0244109 A1 | 8/2019 | Bramlett et al. |
| 2019/0352635 A1 | 11/2019 | Toro et al. |
| 2019/0366293 A1 | 12/2019 | Banyai et al. |
| 2020/0017907 A1 | 1/2020 | Zeitoun et al. |
| 2020/0102611 A1 | 4/2020 | Zeitoun et al. |

(56) References Cited

U.S. PATENT DOCUMENTS

| | | |
|---|---|---|
| 2020/0156037 A1 | 5/2020 | Banyai et al. |
| 2020/0181667 A1 | 6/2020 | Wu et al. |
| 2020/0222875 A1 | 7/2020 | Peck et al. |
| 2020/0283760 A1 | 9/2020 | Nugent et al. |

FOREIGN PATENT DOCUMENTS

| | | |
|---|---|---|
| CA | 2792676 A1 | 9/2011 |
| CN | 1771336 A | 5/2006 |
| CN | 102159726 A | 8/2011 |
| CN | 103907117 A | 7/2014 |
| CN | 104520864 A | 4/2015 |
| CN | 104562213 A | 4/2015 |
| CN | 104734848 A | 6/2015 |
| DE | 10260805 A1 | 7/2004 |
| EP | 0090789 A1 | 10/1983 |
| EP | 0126621 B1 | 8/1990 |
| EP | 0753057 A1 | 1/1997 |
| EP | 1153127 A1 | 11/2001 |
| EP | 1314783 A1 | 5/2003 |
| EP | 1363125 A2 | 11/2003 |
| EP | 1546387 A2 | 6/2005 |
| EP | 1153127 B1 | 7/2006 |
| EP | 1728860 A1 | 12/2006 |
| EP | 1072010 B1 | 4/2010 |
| EP | 2175021 A2 | 4/2010 |
| EP | 2330216 A1 | 6/2011 |
| EP | 1343802 B1 | 5/2012 |
| EP | 2504449 A1 | 10/2012 |
| EP | 2751729 A1 | 7/2014 |
| EP | 2872629 A1 | 5/2015 |
| EP | 2928500 A1 | 10/2015 |
| EP | 2971034 A1 | 1/2016 |
| EP | 3030682 A2 | 6/2016 |
| EP | 3044228 A4 | 4/2017 |
| EP | 2994509 B1 | 6/2017 |
| EP | 3204518 A1 | 8/2017 |
| JP | 2002536977 A | 11/2002 |
| JP | 2002538790 A | 11/2002 |
| JP | 2006503586 A | 2/2006 |
| JP | 2008523786 A | 7/2008 |
| JP | 2008218579 A | 9/2008 |
| JP | 2009294195 A | 12/2009 |
| JP | 2016527313 A | 9/2016 |
| WO | WO-9015070 A1 | 12/1990 |
| WO | WO-9210092 A1 | 6/1992 |
| WO | WO-9210588 A1 | 6/1992 |
| WO | WO-9309668 A1 | 5/1993 |
| WO | WO-9525116 A1 | 9/1995 |
| WO | WO-9526397 A1 | 10/1995 |
| WO | WO-9615861 A1 | 5/1996 |
| WO | WO-9710365 A1 | 3/1997 |
| WO | WO-9822541 A2 | 5/1998 |
| WO | WO-9841531 A2 | 9/1998 |
| WO | WO-9942813 A1 | 8/1999 |
| WO | WO-0013017 A2 | 3/2000 |
| WO | WO-0018957 A1 | 4/2000 |
| WO | WO-0042559 A1 | 7/2000 |
| WO | WO-0042560 A2 | 7/2000 |
| WO | WO-0042561 A2 | 7/2000 |
| WO | WO-0049142 A1 | 8/2000 |
| WO | WO-0053617 A1 | 9/2000 |
| WO | WO-0156216 A2 | 8/2001 |
| WO | WO-0210443 A1 | 2/2002 |
| WO | WO-0156216 A3 | 3/2002 |
| WO | WO-0220537 A2 | 3/2002 |
| WO | WO-0224597 A2 | 3/2002 |
| WO | WO-0227638 A1 | 4/2002 |
| WO | WO-0233669 A1 | 4/2002 |
| WO | WO-02072791 A2 | 9/2002 |
| WO | WO-03040410 A1 | 5/2003 |
| WO | WO-03046223 A1 | 6/2003 |
| WO | WO-03054232 A2 | 7/2003 |
| WO | WO-03060084 A2 | 7/2003 |
| WO | WO-03064026 A1 | 8/2003 |
| WO | WO-03064027 A2 | 8/2003 |
| WO | WO-03064699 A2 | 8/2003 |
| WO | WO-03065038 A2 | 8/2003 |
| WO | WO-03066212 A2 | 8/2003 |
| WO | WO-03089605 A2 | 10/2003 |
| WO | WO-03093504 A1 | 11/2003 |
| WO | WO-03100012 A2 | 12/2003 |
| WO | WO-2004024886 A2 | 3/2004 |
| WO | WO-2004029220 A2 | 4/2004 |
| WO | WO-2004029586 A1 | 4/2004 |
| WO | WO-2004031351 A2 | 4/2004 |
| WO | WO-2004031399 A2 | 4/2004 |
| WO | WO-2004059556 A2 | 7/2004 |
| WO | WO-03060084 A3 | 8/2004 |
| WO | WO-2005014850 A2 | 2/2005 |
| WO | WO-2005051970 A2 | 6/2005 |
| WO | WO-2005059096 A2 | 6/2005 |
| WO | WO-2005059097 A2 | 6/2005 |
| WO | WO-2006023144 | 3/2006 |
| WO | WO-2006044956 A1 | 4/2006 |
| WO | WO-2006076679 A1 | 7/2006 |
| WO | WO-2006116476 A1 | 11/2006 |
| WO | WO-2007109221 A2 | 9/2007 |
| WO | WO-2007120627 A2 | 10/2007 |
| WO | WO-2007137242 A2 | 11/2007 |
| WO | WO-2008003116 A2 | 1/2008 |
| WO | WO-2008006078 A2 | 1/2008 |
| WO | WO-2008027558 A2 | 3/2008 |
| WO | WO-2008045380 | 4/2008 |
| WO | WO-2008054543 A2 | 5/2008 |
| WO | WO-2008063134 A1 | 5/2008 |
| WO | WO-2008063135 A1 | 5/2008 |
| WO | WO-2008109176 A2 | 9/2008 |
| WO | WO-2010025310 A2 | 3/2010 |
| WO | WO-2010025566 A1 | 3/2010 |
| WO | WO-2010027512 A2 | 3/2010 |
| WO | WO-2010089412 A1 | 8/2010 |
| WO | WO-2010141433 A2 | 12/2010 |
| WO | WO-2010141433 A3 | 4/2011 |
| WO | WO-2011053957 A2 | 5/2011 |
| WO | WO-2011056644 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011103468 A2 | 8/2011 |
| WO | WO-2011109031 A1 | 9/2011 |
| WO | WO-2011143556 A1 | 11/2011 |
| WO | WO-2011150168 A1 | 12/2011 |
| WO | WO-2011161413 A2 | 12/2011 |
| WO | WO-2012013913 A1 | 2/2012 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013030827 A1 | 3/2013 |
| WO | WO-2013032850 A2 | 3/2013 |
| WO | WO-2013036668 A1 | 3/2013 |
| WO | WO-2013101896 A1 | 7/2013 |
| WO | WO-2013154770 A1 | 10/2013 |
| WO | WO-2013177220 A1 | 11/2013 |
| WO | WO-2014004393 A1 | 1/2014 |
| WO | WO-2014008447 A1 | 1/2014 |
| WO | WO-2014035693 A2 | 3/2014 |
| WO | WO-2014088693 A1 | 6/2014 |
| WO | WO-2014089160 A1 | 6/2014 |
| WO | WO-2014093330 A1 | 6/2014 |
| WO | WO-2014093694 A1 | 6/2014 |
| WO | WO-2014151117 A1 | 9/2014 |
| WO | WO-2014151696 A1 | 9/2014 |
| WO | WO-2014160004 A1 | 10/2014 |
| WO | WO-2014160059 A1 | 10/2014 |
| WO | WO-2014206304 A1 | 12/2014 |
| WO | WO-2015017527 A2 | 2/2015 |
| WO | WO-2015021080 A2 | 2/2015 |
| WO | WO-2015021280 A1 | 2/2015 |
| WO | WO-2015031689 A1 | 3/2015 |
| WO | WO-2015040075 A1 | 3/2015 |
| WO | WO-2015054292 A1 | 4/2015 |

(56) References Cited

FOREIGN PATENT DOCUMENTS

| | | |
|---|---|---|
| WO | WO-2015066174 A1 | 5/2015 |
| WO | WO-2015081114 A2 | 6/2015 |
| WO | WO-2015081142 A1 | 6/2015 |
| WO | WO-2015090879 A1 | 6/2015 |
| WO | WO-2015095404 A2 | 6/2015 |
| WO | WO-2015120403 A1 | 8/2015 |
| WO | WO-2015136072 A1 | 9/2015 |
| WO | WO-2015160004 A1 | 10/2015 |
| WO | WO-2015175832 A1 | 11/2015 |
| WO | WO-2016007604 A1 | 1/2016 |
| WO | WO-2016011080 A2 | 1/2016 |
| WO | WO-2016022557 A1 | 2/2016 |
| WO | WO-2016053883 A1 | 4/2016 |
| WO | WO-2016055956 A1 | 4/2016 |
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016161244 A2 | 10/2016 |
| WO | WO-2016162127 A1 | 10/2016 |
| WO | WO-2016172377 A1 | 10/2016 |
| WO | WO-2016173719 A1 | 11/2016 |
| WO | WO-2016183100 A1 | 11/2016 |
| WO | WO-2017017423 A1 | 2/2017 |
| WO | WO-2017049231 A1 | 3/2017 |
| WO | WO-2017053450 A1 | 3/2017 |
| WO | WO-2017059399 A1 | 4/2017 |
| WO | WO-2017095958 A1 | 6/2017 |
| WO | WO-2017100441 A1 | 6/2017 |
| WO | WO-2017118761 A1 | 7/2017 |
| WO | WO-2017158103 A1 | 9/2017 |
| WO | WO-2017214574 A1 | 12/2017 |
| WO | WO-2018026920 A1 | 2/2018 |
| WO | WO-2018038772 A1 | 3/2018 |
| WO | WO-2018057526 A2 | 3/2018 |
| WO | WO-2018094263 A1 | 5/2018 |
| WO | WO-2018112426 A1 | 6/2018 |
| WO | WO-2018156792 A1 | 8/2018 |
| WO | WO-2018170164 A1 | 9/2018 |
| WO | WO-2018170169 A1 | 9/2018 |
| WO | WO-2018200380 A1 | 11/2018 |
| WO | WO-2018231872 A1 | 12/2018 |
| WO | WO-2019051501 A1 | 3/2019 |
| WO | WO-2019079769 A1 | 4/2019 |
| WO | WO-2019084500 A1 | 5/2019 |
| WO | WO-2019136175 A1 | 7/2019 |
| WO | WO-2019222706 A1 | 11/2019 |
| WO | WO-2020139871 A1 | 7/2020 |
| WO | WO-2020176362 A1 | 9/2020 |
| WO | WO-2020176678 A1 | 9/2020 |
| WO | WO-2020176680 A1 | 9/2020 |

OTHER PUBLICATIONS

Galka et al.: QuickLib, a method for building fully synthetic plasmid libraries by seamless cloning of degenerate oligonucleotides. PLOS ONE, 12, e0175146:S1 Table (2017).
Galka et al.: QuickLib, a method for building fully synthetic plasmid libraries by seamless cloning of degenerate oligonucleotides. PLOS ONE, 12, e0175146:S2 figure (2017).
International Application No. PCT/US2018/019268 International Preliminary Report on Patentability dated Sep. 6, 2019.
International Application No. PCT/US2019/032992 International Search Report and Written Opinion dated Oct. 28, 2019.
International Application No. PCT/US2019/032992 Invitation to Pay Additional Fees dated Sep. 6, 2019.
Paul et al.: Acid binding and detritylation during oligonucleotide synthesis. Nucleic Acids Research. 15. pp. 3048-3052 (1996).
PubChem Data Sheet Acetonitrile. Printed from website https://pubchem.ncbi.nlm.nig.gov/ pp. 1-124 (2020).
PubChem Data Sheet Methylene Chloride. Printed from website https://pubchem.ncbi.nlm.nih.gov/ pp. 1-140 (2020).
Solomon et al.: Genomics at Agilent: Driving Value in DNA Sequencing.https://www.agilent.com/labs/features/2010_genomics.html, 8 pages (Aug. 5, 2010).
U.S. Appl. No. 14/241,874 Final Office Action dated Jan. 28, 2019.
U.S. Appl. No. 15/015,059 Office Action dated Aug. 19, 2019.
U.S. Appl. No. 15/151,316 Office Action dated Oct. 4, 2019.
U.S. Appl. No. 15/156,134 Final Office Action dated Jan. 3, 2020.
U.S. Appl. No. 15/187,714 Final Office Action dated Sep. 17, 2019.
U.S. Appl. No. 15/268,422 Final Office Action dated Oct. 3, 2019.
U.S. Appl. No. 15/603,013 Final Office Action dated Nov. 6, 2019.
U.S. Appl. No. 15/619,322 Office Action dated Aug. 14, 2019.
U.S. Appl. No. 15/816,995 Office Action dated Sep. 20, 2019.
U.S. Appl. No. 15/835,342 Office Action dated Dec. 2, 2019.
U.S. Appl. No. 15/835,342 Restriction Requirement dated Sep. 10, 2019.
U.S. Appl. No. 15/844,395 Office Action dated Jan. 24, 2020.
U.S. Appl. No. 15/921,479 Office Action dated Nov. 12, 2019.
U.S. Appl. No. 15/960,319 Office Action dated Aug. 16, 2019.
U.S. Appl. No. 15/991,992 Restriction Requirement dated Mar. 10, 2020.
U.S. Appl. No. 16/006,581 Office Action dated Sep. 25, 2019.
U.S. Appl. No. 16/165,952 Office Action dated Mar. 12, 2020.
U.S. Appl. No. 16/239,453 Office Action dated Nov. 7, 2019.
U.S. Appl. No. 16/384,678 Office Action dated Jan. 21, 2020.
U.S. Appl. No. 16/409,608 Office Action dated Sep. 9, 2019.
U.S. Appl. No. 16/530,717 Office Action dated Sep. 6, 2019.
U.S. Appl. No. 16/535,777 Office Action dated Jan. 23, 2020.
U.S. Appl. No. 16/535,779 First Action Interview dated Feb. 10, 2020.
Acevedo-Rocha et al. Directed evolution of stereoselective enzymes based on genetic selection as opposed to screening systems. J. Biotechnol. 191:3-10 (2014).
Arand et al. Structure of Rhodococcus erythropolis limonene-1,2-epoxide hydrolase reveals a novel active site. EMBO J. 22:2583-2592 (2003).
Assembly manual for the POSaM:THE ISB Piezoelelctric Oligonucleotide Synthesizer and Microarrayer, The Institute for Systems Biology, May 28, 2004 (50 pages).
Carter and Friedman, DNA synthesis and Biosecurity: Lessons learned and options for the future. J. Craig Venter Institute, La Jolla, CA, 28 pages, Oct. 2015.
Chilamakuri et al. Performance comparison of four exome capture systems for deep sequencing. BMC Genomics 15(1):449 (2014).
Cruse et al. Atlas of Immunology, Third Edition. Boca Raton:CRC Press (pp. 282-283) (2010).
Dillon et al. Exome sequencing has higher diagnostic yield compared to simulated disease-specific panels in children with suspected monogenic disorders. Eur J Hum Genet 26(5):644-651 (2018).
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).
European Patent Application No. 12827479.2 Extended European Search Report dated May 18, 2015.
European Patent Application No. 12827479.2 Partial European Search Report dated Jan. 29, 2015.
European Patent Application No. 14834665.3 Further Examination Report dated Nov. 28, 2018.
European Patent Application No. 16847497.1 Extended European Search Report dated Jan. 9, 2019.
European Patent Application No. 16871446.7 European Search Report dated Apr. 10, 2019.
Gao et al. A method for the generation of combinatorial antibody libraries using pIX phage display. PNAS 99(20):12612-12616 (2002).
Goldfeder et al. Medical implications of technical accuracy in genome sequencing. Genome Med 8(1):24 (2016).
International Application No. PCT/US2017/026232 International Preliminary Report on Patentability dated Feb. 26, 2019.
International Application No. PCT/US2017/045105 International Preliminary Report on Patentability dated Feb. 5, 2019.
International Application No. PCT/US2017/052305 International Preliminary Report on Patentability dated Apr. 30, 2019.

(56) References Cited

OTHER PUBLICATIONS

International Application No. PCT/US2017/062391 International Preliminary Report on Patentability dated May 21, 2019.
International Application No. PCT/US2018/050511 International Search Report and Written Opinion dated Jan. 11, 2019.
International Application No. PCT/US2018/057857 International Search Report and Written Opinion dated Mar. 18, 2019.
International Application No. PCT/US2019/012218 International Search Report and Written Opinion dated Mar. 21, 2019.
Jacobus et al. Optimal cloning of PCR fragments by homologous recombination in *Escherichia soli*. PLoS One 10(3):e0119221 (2015).
Li et al. Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Light source unit for printable patterning VUV-Aligner / USHIO Inc., Link here: https://www.ushio.co.jp/en/products/1005.html, published Apr. 25, 2016, printed from the internet on Aug. 2, 2016, 3 pages.
Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).
Meynert et al. Quantifying single nucleotide variant detection sensitivity in exome sequencing. BMC Bioinformatics 14:195 (2013).
Meynert et al. Variant detection sensitivity and biases in whole genome and exome sequencing. BMC Bioinformatics 15:247 (2014).
Mulligan. Commercial Gene Synthesis Technology PowerPoint presentation. BlueHeron® Biotechnology. Apr. 5, 2006 (48 pgs).
Jo et al.: Engineering therapeutic antibodies targeting G-protein-coupled receptors; Experimental & Molecular Medicine; 48; 9 pages (2016).
Douthwaite et al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
PCT/IL2012/000326 International Preliminary Report on Patentability dated Dec. 5, 2013.
PCT/IL2012/000326 International Search Report dated Jan. 29, 2013.
PCT/US2016/064270 International Preliminary Report on Patentability dated Jun. 14, 2018.
PCT/US2018/022487 International Search Report and Written Opinion dated Aug. 1, 2018.
PCT/US2018/022493 International Search Report and Written Opinion dated Aug. 1, 2018.
PCT/US2018/037152 International Search Report and Written Opinion dated Aug. 28, 2018.
PCT/US2018/037161 International Search Report and Written Opinion dated Oct. 22, 2018.
PCT/US2018/037161 Invitation to Pay Additional Fees dated Aug. 27, 2018.
PCT/US2018/056783 International Search Report and Written Opinion of the International Searching Authority dated Dec. 20, 2018.
PCT/US2018/19268 International Search Report and Written Opinion dated Jun. 26, 2018.
Puigbo. Optimizer: a web server for optimizing the codon usage of DNA sequences. Nucleic Acid Research, 35(14):126-131, 2007.
Sharan et al. Recombineering: a homologous recombination-based method of genetic engineering. Nat Profile 4(2):1-37 (originally pp. 206-223) (2009).
Martinez-Torrecuadrada et al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).
U.S. Appl. No. 15/187,714 Office Action dated Apr. 4, 2019.
U.S. Appl. No. 15/603,013 Office Action dated Jun. 26, 2019.
Sullivan et al. Library construction and evaluation for site saturation mutagenesis. Enzyme Microb. Technol. 53:70-77 (2013).
Sun et al. Structure-Guided Triple-Code Saturation Mutagenesis: Efficient Tuning of the Stereoselectivity of an Epoxide Hydrolase. ACS Catal. 6:1590-1597 (2016).
U.S. Appl. No. 14/241,874 Office Action dated Jul. 14, 2016.
U.S. Appl. No. 14/241,874 Office Action dated May 4, 2018.
U.S. Appl. No. 14/885,963 Office Action dated Feb. 5, 2016.
U.S. Appl. No. 14/885,965 Office Action dated Aug. 28, 2018.
U.S. Appl. No. 15/015,059 Final Office Action dated Jul. 17, 2019.
U.S. Appl. No. 15/015,059 Office Action dated Feb. 7, 2019.
U.S. Appl. No. 15/156,134 Office Action dated Apr. 4, 2019.
U.S. Appl. No. 15/187,714 Restriction Requirement dated Sep. 17, 2018.
U.S. Appl. No. 15/268,422 Office Action dated Mar. 1, 2019.
U.S. Appl. No. 15/268,422 Restriction Requirement dated Oct. 4, 2018.
U.S. Appl. No. 15/377,547 Final Office Action dated Feb. 8, 2019.
U.S. Appl. No. 15/377,547 Office Action dated Jul. 27, 2018.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/602,991 Office Action dated May 31, 2019.
U.S. Appl. No. 15/603,013 Office Action dated Jul. 10, 2018.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated May 30, 2019.
U.S. Appl. No. 15/816,995 Restriction Requirement dated Apr. 4, 2019.
U.S. Appl. No. 15/844,395 Restriction Requirement dated May 17, 2019.
U.S. Appl. No. 15/860,445 Final Office Action dated Dec. 13, 2018.
U.S. Appl. No. 15/921,479 Restriction Requirement dated May 24, 2019.
U.S. Appl. No. 15/151,316 Final Office Action dated Feb. 21, 2019.
Van Der Werf et al. Limonene-1,2-epoxide hydrolase from Rhodococcus erythropolis DCL14 belongs to a novel class of epoxide hydrolases. J. Bacteriol. 180:5052-5057 (1998).
Warr et al. Exome Sequencing: current and future perspectives. G3: (Bethesda) 5(8):1543-1550 (2015).
Wu, et al. Sequence-Specific Capture of Protein-DNA Complexes for Mass Spectrometric Protein Identification PLoS ONE. Oct. 20, 2011, vol. 6, No. 10.
Zheng et al. Manipulating the Stereoselectivity of Limonene Epoxide Hydrolase by Directed Evolution Based on Iterative Saturation Mutagenesis. J. Am. Chem. Soc. 132:15744-15751 (2010).
Zhou, et al. Establishment and application of a loop-mediated isothermal amplification (LAMP) system for detection of cry1Ac transgenic sugarcane Scientific Reports May 9, 2014, vol. 4, No. 4912.
De Silva et al. New Trends of Digital Data Storage in DNA. BioMed Res Int. 2016:8072463 (2016).
European Patent Application No. 14834665.3 Office Action dated May 2, 2018.
Gibson et al. Creation of a Bacterial Cell Controlled by a Chemically Synthesized Genome. Science 329(5989):52-56 (2010).
Han et al. Linking T-cell receptor sequence to functional phenotype at the single-cell level. Nat Biotechnol 32(7):684-692 (2014).
Jager et al. Simultaneous Humoral and Cellular: Immune Response against Cancer—Testis Antigen NY-ES0-1: Definition of Human Histocompatibility LeukocyteAntigen (HLA)-A2—binding Peptide Epitopes. J. Exp. Med. 187(2):265-270 (1998).
Li et al. Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
PCT/US2016/052336 International Preliminary Report on Patentability dated Mar. 29, 2018.
PCT/US2016/052916 International Preliminary Report on Patentability dated Apr. 5, 2018.

(56) References Cited

OTHER PUBLICATIONS

PCT/US2017/062391 International Search Report and Written Opinion dated Mar. 28, 2018.
PCT/US2017/066847 International Search Report and Written Opinion dated May 4, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
Skerra. Phosphorothioate primers improve the amplification of DNA sequences by DNA polymerases with proofreading activity. Nucleic Acids Res. Jul. 25, 1992; 20(14):3551-4.
Twist Bioscience | White Paper. DNA-Based Digital Storage. Retrieved from the internet, Twistbioscience.com, Mar. 27, 2018, 5 pages.
U.S. Appl. No. 15/151,316 Office Action dated Jun. 7, 2018.
U.S. Appl. No. 15/602,991 Office Action dated May 31, 2018.
U.S. Appl. No. 15/729,564 Office Action dated Jun. 6, 2018.
U.S. Appl. No. 15/860,445 Office Action dated May 30, 2018.
CeGaT. Tech Note available at https://www.cegat.de/web/wp-content/uploads/2018/06/Twist-Exome-Tech-Note.pdf (4 pgs.) (2018).
Abudayyeh et al., C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf , 17 pages.
Adessi, et al. Solid phase DNA amplification: characterisation of primer attachment and amplification mechanisms. Nucleic Acids Res. 28(20):E87, 2000.
Alexeyev, Mikhail F. et al., "Gene synthesis, bacterial expression and purification of the Rickettsia prowazekii ATP/ADP translocase", Biochimica et Biophysics Acta, 1419:299-306, 1999.
Al-Housseiny et al., Control of interfacial instabilities using flow geometry Nature Physics, 8:747-750, 2012.
Amblard, Francois et al., "A magnetic manipulator for studying local rheology and micromechanical properties of biological systems", Rev. Sci. Instrum., 67(3):18-827, 1996.
Andoni and Indyk, Near-Optimal Hashing Algorithms for Approximate Nearest Neighbor in High Dimensions, Communications of the ACM, 51(1):117-122, 2008.
Arkles, et al. The Role of Polarity in the Structure of Silanes Employed in Surface Modification. Silanes and Other Coupling Agents. 5:51-64, 2009.
Arkles, Hydrophobicity, Hydrophilicity Reprinted with permission from the Oct. 2006 issue of Paint & Coatings Industry magazine, Retrieved on Mar. 19, 2016, 10 pages.
Assi, Fabiano et al., "Massive-parallel adhesion and reactivity—measurements using simple and inexpensive magnetic tweezers", J. Appl. Phys., 92(9):5584-5586, 2002.
ATDBio, "Nucleic Acid Structure," Nucleic Acids Book, 9 pages, published on Jan. 22, 2005. from: http://www.atdbio.com/content/5/Nucleic-acid-structure.
ATDBio, "Solid-Phase Oligonucleotide Synthesis," Nucleic Acids Book, 20 pages, Published on Jul. 31, 2011. from: http://www.atdbio.com/content/17/Solid-phase-oligonucleotide-synthesis.
Au, Lo-Chun et al. "Gene synthesis by a LCR-based approach: high level production of Leptin-L54 using synthetic gene in *Escherichia coli*", Biochemical and Biophysical Research Communications, 248:200-203, 1998.
Baedeker, Mathias et al., Overexpression of a designed 2.2kb gene of eukaryotic phenylalanine ammonialyase in *Escherichia coli*•. FEBS Letters, 457:57-60, 1999.
Barbee, et al. Magnetic Assembly of High-Density DNA Arrays for Genomic Analyses. Anal Chem. 80(6):2149-2154, 2008.
Barton et al., A desk electrohydrodynamic jet printing system. Mechatronics, 20:611-616, 2010.
Beaucage, et al. Advances in the synthesis of oligonucleotides by the phosphoramidite approach. Tetrahedron. 48:2223-2311, 1992.
Beaucage, et al. Deoxynucleoside phosphoramidites—A new class of key intermediates for deoxypolynucleotide synthesis. Tetrahedron Lett. 22(20):1859-1862, 1981.
Beaucage, Serge L. et al., "The Chemical synthesis of DNA/RNA" Chapter 2 in: Encyclopedia of Cell Biology, 1:36-53, 2016.
Beaulieu, Martin et al., "PCR candidate region mismatch scanning adaptation to quantitative, high-throughput genotyping", Nucleic Acids Research, 29(5):1114-1124, 2001.
Beigelman, et al. Base-modified phosphoramidite analogs of pyrimidine ribonucleosides for RNA structure-activity studies. Methods Enzymol. 317:39-65, 2000.
Bethge et al., "Reverse synthesis and 3'-modification of RNA." Jan. 1, 2011, pp. 64-64, XP055353420. Retrieved from the Internet: URL:http://www.is3na.org/assets/events/Category%202-Medicinal%20Chemistry%20of%2001igonucleotides%20%2864-108%29.pdf.
Binkowski et al., Correcting errors in synthetic DNA through consensus shuffling. Nucleic Acids Research, 33(6):e55, 8 pages, 2005.
Biswas, Indranil et al., "Identification and characterization of a thermostable MutS homolog from Thennus aquaticus", The Journal of Biological Chemistry, 271(9):5040-5048, 1996.
Biswas, Indranil et al., "Interaction of MutS protein with the major and minor grooves of a heteroduplex DNA", The Journal of Biological Chemistry, 272(20):13355-13364, 1997.
Bjornson, Keith P. et al., "Differential and simultaneous adenosine Di- and Tri~hosphate binding by MutS", The Journal of Biological Chemistry, 278(20):18557-18562, 2003.
Blanchard, et al., "High-Density Oligonucleotide Arrays," Biosensors & Bioelectronics, 11(6/7):687-690, 1996.
Blanchard, in: Genetic Engineering, Principles and Methods, vol. 20, Ed. J. Sedlow, New York: Plenum Press, p. 111-124, 1979.
Blawat et al., Forward error correction for DNA data storage. Procedia Computer Science, 80:1011-1022, 2016.
Bonini and Mondino, Adoptive T-cell therapy for cancer: The era of engineered T cells. European Journal of Immunology, 45:2457-2469, 2015.
Bornholt et al., A DNA-Based Archival Storage System, in International Conference on Architectural Support for Programming Languages and Operating Systems (ASPLOS), Apr. 2-6, 2016, Atlanta, GA, 2016, 637-649.
Borovkov et al., High-quality gene assembly directly from unpurified mixtures of microassay-synthesized oligonucleotides. Nucleic Acid Research, 38(19):e180, 10 pages, 2010.
Brunet, Aims and methods of biosteganography. Journal of Biotechnology, 226:56-64, 2016.
Buermans et al., "Next Generation sequencing technology: Advances and applications," Biochimica et Biophysica Acta (BBA)—Molecular Basis of Disease, 1842:1931-1941, 2014.
Butler, et al. In situ synthesis of oligonucleotide arrays by using surface tension. J Am Chem Soc. 123(37):8887-94, 2001.
Calvert, Lithographically patterned self-assembled films. In: Organic Thin Films and Surfaces: Directions for the Nineties, vol. 20, p. 109, ed. By Abraham Ulman, San Diego: Academic Press, 1995.
Cardelli, Two-Domain DNA Strand Displacement, Electron. Proc. Theor. Comput. Sci., 26:47-61, 2010.
Carlson, "Time for New DNA Synthesis and Sequencing Cost Curves," 2014. [Online]. Available: http://www.synthesis.cc/synthesis/2014/02/time_for_new_cost_curves_2014. 10 pages.
Carr, et al. Protein-mediated error correction for de novo DNA synthesis. Nucleic Acids Res. 32(20):e162, 9 pages, 2004.
Caruthers, Chemical synthesis of deoxyoligonucleotides by the phosphoramidite method. In Methods in Enzymology, Chapter 15, 154:287-313, 1987.
Caruthers. Gene synthesis machines: DNA chemistry and its uses. Science. 230(4723):281-5, 1985.
Caruthers, The Chemical Synthesis of DNA/RNA: Our Gift to Science. J. Biol. Chem., 288(2):1420-1427, 2013.
Casmiro, Danilo R. et al., "PCR-based gene synthesis and protein NMR spectroscopy", Structure, 5(11):1407-1412, 1997.
Cello, et al. Chemical synthesis of poliovirus cDNA: generation of infectious virus in the absence of natural template. Science. 297(5583):1016-8, 2000.

(56) References Cited

OTHER PUBLICATIONS

Chalmers, et al. Scaling up the ligase chain reaction-based approach to gene synthesis. Biotechniques. 30(2):249-52, 2001.
Chan, et al. Natural and engineered nicking endonucleases—from cleavage mechanism to engineering of strand-specificity. Nucleic Acids Res. 39(1):1-18, 2011.
Chen, et al. Chemical modification of gene silencing oligonucleotides for drug discovery and development. Drug Discov Today. 10(8):587-93 2005.
Chen et al., Programmable chemical controllers made from DNA, Nat. Nanotechnol., 8(10):755-762, 2013.
Cheng, et al. High throughput parallel synthesis of oligonucleotides with 1536 channel synthesizer. Nucleic Acids Res. 30(18):e93, 2002.
Cho, et al. Capillary passive valve in microfluidic systems. NSTI-Nanotech. 2004; 1:263-266.
Chrisey et al., Fabrication of patterned DNA surfaces Nucleic Acids Research, 24(15):3040-3047 (1996).
Chung et al., One-step preparation of competent *Escherichia coli*: Transformation and storage of bacterial cells in the same solution. Proc Natl Acad Sci U S A. Apr. 1989;86(7):2172-2175.
Church et al., Next-generation digital information storage in DNA. Science, 337:6102, 1628-1629, 2012.
Cleary et al., "Production of complex nucleic acid libraries using highly parallel in situ oligonucleotide synthesis," Nature Methods, 1(13):241-248, 2004.
Cohen et al., Human population: The next half century. Science, 302:1172-1175, 2003.
Crick. On protein synthesis. Symp Soc Exp Biol 12:138-163,1958.
Cutler, David J. et al., "High-throughput variation detection and genotyping using microarrays", Genome Research, vol. 11, 1913-19 (2001).
Dahl, et al. Circle-to-circle amplification for precise and sensitive DNA analysis. Proc Natl Acad Sci U S A. Mar. 30, 2004;101(13):4548-53.
De Mesmaeker, et al. Backbone modifications in oligonucleotides and peptide nucleic acid systems. Curr Opin Struct Biol. Jun. 1995;5(3):343-55.
Deamer, David W. et al., "Characterization of nucleic acids by nanopore analysis", Ace. Cham. Res., vol. 35, No. 10, 817-825 (2002).
Deaven, The Human Genome Project: Recombinant clones for mapping and sequencing DNA. Los Alamos Science, 20:218-249, 1992.
Deng et al., Targeted bisulfite sequencing reveals changes in DNA methylation associated with nuclear reprogramming Nature Biotechnology, 27:352-360 (2009).
Dietrich, Rudiger.et al., "Gene assembly based on blunt-ended double-stranded DNA-modules", Biotechnology Techniques, vol. 12, No. 1, 49-54 (Jan. 1998).
Dormitzer et al., Synthetic generation of influenza vaccine viruses for rapid response to pandemics. Sci Translational Medicine, 5(185):185ra68, 14 pages, 2013.
Doudna et al. Genome editing. The new frontier of genome engineering with CRISPR-Cas9. Science 346(6213):1258096-1-1258096-9, 2014.
Dower et al., High efficiency transformation of *E.coli* by high voltage electroporation. Nucleic Acids Res. 16(13):6127-45 (1988).
Dressman, et al. Transforming single DNA molecules into fluorescent magnetic particles for detection and enumeration of genetic variations. Proc Natl Acad Sci U S A. Jul. 22, 2003;100(15):8817-22.
Drmanac, et al. Human genome sequencing using unchained base reads on self-assembling DNA nanoarrays. Science. Jan. 1, 2010;327(5961):78-81.
Droege and Hill, The Genome Sequencer FLXTM System—Longer reads, more applications, straight forward bioinformatics and more complete data sets . Journal of Biotechnology, 136:3-10, 2008.
Duffy, et al. Rapid Prototyping of Microfluidic Systems in Poly(dimethylsiloxane). Anal Chem. Dec. 1, 1998;70(23):4974-84.

Duggan, et al. Expression profiling using cDNA microarrays. Nat Genet. Jan. 1999;21(1 Suppl):10-4.
Eadie, et al. Guanine modification during chemical DNA synthesis. Nucleic Acids Res. Oct. 26, 1987;15(20):8333-49.
Eisen, Jonathan A., "A phylogenomic study of the MutS family of proteins", Nucleic Acids Research, vol. 26, No. 18, 4291-4300 (1998).
Ellis, et al. DNA assembly for synthetic biology: from parts to pathways and beyond. Integr Biol (Camb). Feb. 2011;3(2):109-18.
El-Sagheer, et al. Biocompatible artificial DNA linker that is read through by DNA polymerases and is functional in *Escherichia coli*. Proc Natl Acad Sci U S A. Jul. 12, 2011;108(28):11338-43.
Elsik et al., The Genome sequence of taurine cattle: A window of ruminant biology and evolution. Science, 324:522-528, 2009.
Elsner et al., 172 nm excimer VUV-triggered photodegradation and micropatterning of aminosilane films, Thin Solid Films, 517:6772-6776, 2009.
Engler, et al. A one pot, one step, precision cloning method with high throughput capability. PLoS One. 2008;3(11):e3647.
Engler, et al. Golden gate shuffling: a one-pot DNA shuffling method based on type IIs restriction enzymes. PLoS One. 2009;4(5):e5553.
Erlich and Zielinski, DNA fountain enables a robust and efficient storage architecture. Science, 355(6328):950-054, 2017.
European Patent Application No. 14834665.3 extended European Search Report dated Apr. 28, 2017.
Evans et al, DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided).
Fahy, et al. Self-sustained sequence replication (3SR): an isothermal transcription-based amplification system alternative to PCR. PCR Methods Appl. Aug. 1991;1(1):25-33.
Fedoryak, Olesya D. et al., "Brominated hydroxyquinoline as a photolabile protecting group with sensitivity to multiphoton excitation", Org. Lett., vol. 4, No. 2 , 3419-3422 (2002).
Ferretti et al., Total synthesis of a gene for bovine rhodopsin. PNAS, 83:599-603 (1986).
Finger et al., The wonders of Flap Endonucleases: Structure, function, mechanism and regulation. Subcell Biochem., 62:301-326, 2012.
Fodor et al. "Light-Directed, Spatially Addressable Parallel Chemical Synthesis," Science, 251(4995):767-773, 1991.
Fogg et al., Structural basis for uracil recognition by archaeal family B DNA polymerases. Nature Structural Biology, 9(12):922-927, 2002.
Foldesi, et al. The synthesis of deuterionucleosides. Nucleosides Nucleotides Nucleic Acids. Oct.-Dec. 2000;19(10-12):1615-56.
Frandsen, et al. Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The USER Friendly technology. USER cloning. Oct. 7, 2010, 2 pages. http://www.rasmusfrandsen.dk/user_cloning.htm.
Fullwood et al., Next-generation DNA sequencing of paired-end tags [PET] for transcriptome and genome analysis Genome Research, 19:521-532, 2009.
Galneder. et al., Microelectrophoresis of a bilayer-coated silica bead in an optical trap: application to enzymology. Biophysical Journal, vol. 80, No. 5, 2298-2309 (May 2001).
Gao, et al. A flexible light-directed DNA chip synthesis gated by deprotection using solution photogenerated acids. Nucleic Acids Res. Nov. 15, 2001;29(22):4744-50.
Gao, et al. Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj, et al. Graphene as a subnanometre trans-electrode membrane. Nature. Sep. 9, 2010;467(7312):190-3.
Garbow, Norbert et al., "Optical tweezing electroghoresis of isolated, highly charged colloidal spheres", Colloids and Surfaces A: Physiochem. Eng. Aspects, vol. 195, 227-241 (2001).

(56) References Cited

OTHER PUBLICATIONS

GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores, et al. USER fusion: a rapid and efficient method for simultaneous fusion and cloning of multiple PCR products. Nucleic Acids Res. 2007;35(7):e55.
Gibson Assembly. Product Listing. Application Overview. 2 pages, available online Dec. 16, 2014.
Gibson, et al. Complete chemical synthesis, assembly, and cloning of a Mycoplasma genitalium genome. Science. Feb. 29, 2008;319(5867):1215-20.
Goldman et al., Towards practical, high-capacity, low-maintenance information storage in synthesized DNA, Nature, 494(7435):77-80, 2013.
Gosse, Charlie et al. "Magnetic tweezers: micromanipulation and force measurement at the molecular level", Biophysical Journal, vol. 8, 3314-3329 (Jun. 2002).
Grass, et al., Robust chemical preservation of digital information on DNA in silica with error-correcting codes, Angew. Chemie—Int. Ed., 54(8):2552-2555, 2015.
Greagg et al., A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al., Depletion of abundant sequences by hybridization (DASH): using Cas9 to remove unwanted high-abundance species in sequencing libraries and molecular counting applications. Genome Biology, 17:41, 13 pages, 2016.
Haber, Charbel et al., Magnetic tweezers for DNA micromanipulation, Rev. Sci. Instrum., vol. 71, No. 12, 4561-4570 (Dec. 2000).
Hanahan and Cold Spring Harbor Laboratory, Studies on transformation of *Escherichia coli* with plasmids J. Mol. Biol. 166:557-580 (1983).
Hanahan et al., Plasmid transformation of *Escherichia coli* and other bacteria. Methods Enzymol, vol. 204, p. 63-113 (1991).
Harada, et al. Unexpected substrate specificity of T4 DNA ligase revealed by in vitro selection. Nucleic Acids Res. May 25, 1993;21(10):2287-91.
Heckers Karl H. et al., "Error analysis of chemically synthesized polynucleotides", BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al., "DNAWorks: an automated method for designing oligonucleotides for PCR-based gene synthesis", Nucleic Acids Research, vol. 30, No. 10, e43, 7 pages (2002).
Hosu, Basarab G. et al., Magnetic tweezers for intracellular applications•, Rev. Sci. Instrum., vol. 74, No. 9, 4158-4163 (Sep. 2003).
Huang, Hayden et al., "Three-dimensional cellular deformation analysis with a two-photon magnetic manipulator workstation", Biophysical Journal, vol. 82, No. 4, 2211.2223 (Apr. 2002).
Hughes, et al. Expression profiling using microarrays fabricated by an ink-jet oligonucleotide synthesizer. Nat Biotechnol. Apr. 2001;19(4):342-7.
Hughes et al. Principles of early drug discovery. Br J Pharmacol 162(2):1239-1249, 2011.
Hutchison, et al. Cell-free cloning using phi29 DNA polymerase. Proc Natl Acad Sci U S A. Nov. 29, 2005;102(48):17332-6.
Imgur: The magic of the internet. Uploaded May 10, 2012, 2 pages, retrieved from: https://imgur.com/mEWuW.
In-Fusion Cloning: Accuracy, Not Background. Cloning & Competent Cells, ClonTech Laboratories, 3 pages, available online Jul. 6, 2014.

Jackson, Brian A. et al., "Recognition of DNA base mismatches by a rhodium intercalator", J. Am. Chem. Soc., vol. 19, 12986•12987 (1997).
Jacobs and Schar, DNA glycosylases: In DNA repair and beyond Chromosome, 121:1-20 (2012)—http://www.ncbi.nlm.nih.gov/pmc/articles/PMC3260424/.
Jinek et al., A Programmable dual-RNA-guided DNA endonuclease in adaptive bacterial immunity. Science, 337:816-821, 2012.
Karagiannis and El-Osta, RNA interference and potential therapeutic applications of short interfering RNAs Cancer Gene Therapy, 12:787-795, 2005.
Ke, Song-Hua et al., "Influence of neighboring base pairs on the stability of single base bulges and base pairs in a DNA fragment", Biochemistry, Vo. 34, 4593-4600 (1995).
Kelley, Shana, et al. Single-base mismatch detection based on charge transduction through DNA, Nucleic Acids Research, vol. 27, No. 24, 4830-4837 (1999).
Kim et al., High-resolution patterns of quantum dots formed by electrohydrodynamic jet printing for light-emitting diodes. Nano Letters, 15:969-973, 2015.
Kim, Yang-Gyun et al., "Chimeric restriction endonuclease", Proc. Natl. Acad. Sci. USA, vol. 91, 883-887 (Feb. 1994).
Kim, Yang-Gyun, "The interaction between Z-ONA and the Zab domain of double-stranded RNA adenosine deaminase characterized using fusion nucleases", The Journal of Biological Chemistry, vol. 274, No. 27, 19081-19086 (1999).
Kim, Yan-Gyun et al., "Site specific cleavage of DNA-RNA hybrids by zinc finger/Fok I cleavage domain fusions" Gene, vol. 203, 43-49 (1997).
Kinde, et al. Detection and quantification of rare mutations with massively parallel sequencing. Proc Natl Acad Sci U S A. Jun. 7, 2011;108(23):9530-5.
Kodumal, et al. Total synthesis of long DNA sequences: synthesis of a contiguous 32-kb polyketide synthase gene cluster. Proc Natl Acad Sci U S A. Nov. 2, 2004;101(44):15573-8.
Koike-Yusa et al., Genome-wide recessive genetic screening in mammalian cells with a lentiviral CRISPR-guide RNA library. Nature Biotechnology, 32:267-273, 2014 (with three pages of supplemental "Online Methods").
Kong et al., Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp, Martin U. et al., "Chemical amplification: continuous-flow PCR on a chip", Science, vol. 280, 1046-1048 (May 15, 1998).
Kosuri and Church, "Large-scale de novo DNA synthesis: technologies and applications," Nature Methods, 11:499-507, 2014. Available at: http://www.nature.com/nmeth/journal/v11/n5/full/nmeth.2918.html.
Kosuri, et al. A scalable gene synthesis by selective amplification of DNA pools from high-fidelity microchips. Nature Biotechnology. 2010; 28:1295-1299.
Krayden, Inc., A Guide to Silane Solutions. Silane coupling agents. 7 pages. Published on May 31, 2005 at: http://krayden.com/pdf/xia_silane_chemistry.pdf.
Lagally, E.T. et al., "Single-molecule DNA amplification and analysis in an integrated microfluidic device" Anal. Chem., vol. 73, No. 565-570 (Feb. 1, 2001).
Lahue, R.S. et al., "DNA mismatch correction in a defined system", Science, vol. 425; No. 4914, 160-164 (Jul. 14, 1989).
Lambrinakos, A. et al., "Reactivity of potassium permanganate and tetraethylammonium chloride with mismatched bases and a simple mutation detection protocol", Nucleic Acids Research, vol. 27, No. 8, 1866-1874 (1999).
Landegren, et al. A ligase-mediated gene detection technique. Science. Aug. 26, 1988;241(4869):1077-80.
Lang, Matthew J. et al., "An automated two-dimensional optical force clamp for single molecule studies", Biophysical Journal, vol. 83, 491•501 (Jul. 2002).

(56) References Cited

OTHER PUBLICATIONS

Lashkari, et al. An automated multiplex oligonucleotide synthesizer: development of high-throughput, low-cost DNA synthesis. Proc Natl Acad Sci U S A. Aug. 15, 1995;92(17):7912-5.

Lausted et al., "POSaM: a fast, flexible, open-source, inkjet oligonucleotide synthesizer and microarrayer," Genome Biology, 5:R58, 17 pages, 2004. available at https://www.ncbi.nlm.nih.gov/pmc/articles/PMC507883/.

Leamon, et al. A massively parallel PicoTiterPlate based platform for discrete picoliter-scale polymerase chain reactions. Electrophoresis. Nov. 2003;24(21):3769-77.

Lee, Covalent end-immobilization of oligonucleotides onto solid surfaces. Thesis submitted to the Department of Chemical Engineering in Partial Fulfillment of the Requirements for the Degree of Doctor of Philosophy in Chemical Engineering at the Massachusetts Institute of Technology. Aug. 2001, 315 pages.

Lee, C.S. et al., "Microelectromagnets for the control of magnetic nanoparticles", Appl. Phys. Lett., vol. 79, No. 20, 3308-3310 (Nov. 12, 2001).

Lee, et al. A microfluidic oligonucleotide synthesizer. Nucleic Acids Research 2010 vol. 38(8):2514-2521.

Leproust, et al. Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.

Leproust et al., "Synthesis of high-quality libraries of long (150mer) oligonucleotides by a novel depurination controlled process," Nucleic Acids Research, 35(8):2522-2540, 2010.

Lesnikowski, et al. Nucleic acids and nucleosides containing carboranes. J. Organometallic Chem. 1999; 581:156-169.

Leumann. DNA analogues: from supramolecular principles to biological properties. Bioorg Med Chem. Apr. 2002;10(4):841-54.

Levene, et al. Zero-mode waveguides for single-molecule analysis at high concentrations. Science. Jan. 31, 2003;299(5607):682-6.

Lewontin and Harti, Population genetics in forensic DNA typing. Science, 254:1745-1750, 1991.

Limbachiya et al., Natural data storage: A review on sending information from now to then via Nature. ACM Journal on Emerging Technologies in Computing Systems, V(N):Article A, May 19, 2015, 17 pages.

Link Technologies. "Product Guide 2010." Nov. 27, 2009, 136 pages. XP055353191. Retrieved from the Internet: URL:http://www.linktech.co.uk/documents/517/517.pdf.

Lipshutz, Robert J. et al., "High density synthetic oligonucleotide arrays", Nature Genetics Supplement, vol. 21, 20-24 (Jan. 1999).

Lishanski, Alia et al., "Mutation detection by mismatch binding protein, MutS, in amplified DNA: application to the cystic fibrosis gene", Proc. Natl. Acad. Sci. USA, vol. 91, 2674-2678 (Mar. 1994).

Liu et al., Comparison of Next-Generation Sequencing Systems. Journal of Biomedicine and Biotechnology, 11 pages, 2012.

Liu, et al. Enhanced Signals and Fast Nucleic Acid Hybridization by Microfluidic Chaotic Mixing. Angew. Chem. Int. Ed. 2006; 45:3618-3623.

Liu et al., Rational design of CXCR4 specific antibodies with elongated CDRs. JACS, 136:10557-10560, 2014.

Lizardi, et al. Mutation detection and single-molecule counting using isothermal rolling-circle amplification. Nat Genet. Jul. 1998;19(3):225-32.

Li, Lin et al., "Functional domains in Fok I restriction endonuclease", Proc. Natl. Acad. Sci. USA, 89:4275-4279, 1992.

Lu, A.-Lien et al., "Methyl-directed repair of DNA base-pair mismatches in vitro", Proc. Natl. Acad. Sci. USA, 80:4639-4643, 1983.

Lund, et al. A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.

Ma, et al. DNA synthesis, assembly and application in synthetic biology. Current Opinion in Chemical Biology. 16:260-267, 2012.

Ma et al., Versatile surface functionalization of cyclic olefin copolymer (COC) with sputtered SiO2 thin film for potential BioMEMS applications. Journal of Materials Chemistry, 11 pages, 2009.

Mahato et al., Modulation of gene expression by antisense and antigene oligodeoxynucleotides and small interfering RNA Expert Opin. Drug Delivery, 2(1):3-28, 2005.

Margulies, et al. Genome sequencing in open microfabricated high-density picolitre reactors. Nature. 437(7057):376-80, 2005.

Matteucci, et al. Synthesis of deoxyoligonucleotides on a polymer support. J. Am. Chem. Soc. 103(11):3185-3191, 1981.

Matzas et al., Next generation gene synthesis by targeted retrieval of bead-immobilized, sequence verified DNA clones from a high throughput pyrosequencing device. Nat. Biotechnol., 28(12):1291-1294, 2010.

McBride & Caruthers, "An investigation of several deoxynucleoside phosphoramidites useful for synthesizing deoxyoligonucleotides." Tetrahedron Lett. 24: 245-248, 1983.

McGall, et al. Light-directed synthesis of high-density oligonucleotide arrays using semiconductor photoresists. Proc Natl Acad Sci USA. 93(24):13555-60, 1996.

McGall, et al. The Efficiency of Light-Directed Synthesis of DNA Arrays on Glass Substrates. J. Am. Chem. Soc. 119(22):5081-5090, 1997.

Mei et al., Cell-free protein synthesis in microfluidic array devices Biotechnol. Prog., 23(6):1305-1311, 2007.

Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-portal.org/smash/get/diva2:161926/FULLTEXT01.pdf.

Meyers and Friedland, Knowledge-based simulation of genetic regulation in bacteriophage lambda. Nucl. Acids Research, 12(1):1-16, 1984.

Milo and Phillips, Numbers here reflect the number of protein coding genes and excludes tRNA and non-coding RNA. Cell Biology by the Numbers, p. 286, 2015.

Mitra, et al. In situ localized amplification and contact replication of many individual DNA molecules. Nucleic Acids Res. 27(24):e34, 1999.

Morin et al., Profiling the HeLa S3 transcriptome using randomly primed cDNA and massively parallel short-read sequencing. Biotechniques, 45:81-94, 2008.

Morris and Stauss, Optimizing T-cell receptor gene therapy for hematologic malignancies. Blood, 127(26):3305-3311, 2016.

Muller, Caroline et al. "Protection and labelling of thymidine by a fluorescent photolabile group", Helvetica Chimica Acta, vol. 84, 3735-3741 (2001).

Nakatani, Kazuhiko et al., "Recognition of a single guanine bulge by 2-Acylamino-1,8-naphthyridine", J. Am. Chem. Soc., vol. 122, 2172-2177 (2000).

Neiman M.S,. Negentropy principle in information processing systems. Radiotekhnika, 1966, No 11, p. 2-9.

Neiman M.S., On the bases of the theory of information retrieval. Radiotekhnika, 1967, No 5, p. 2-10.

Neiman M.S., On the molecular memory systems and the directed mutations. Radiotekhnika, 1965, No. 6, pp. 1-8.

Neiman M.S., On the relationships between the reliability, performance and degree of microminiaturization at the molecular-atomic level. Radiotekhnika, 1965, No. 1, pp. 1-9.

Neiman M.S., Some fundamental issues of microminiaturization. Radiotekhnika, 1964, No. 1, pp. 3-12.

Nishikura, A short primer on RNAi: RNA-directed RNA polymerase acts as a key catalyst Cell, 107:415-418, 2001.

Nour-Eldin, et al. USER Cloning and USER Fusion: The Ideal Cloning Techniques for Small and Big Laboratories. Plant Secondary Metabolism Engineering. Methods in Molecular Biology vol. 643, 2010, pp. 185-200.

Ochman, et al. Genetic applications of an inverse polymerase chain reaction. Genetics. Nov. 1988;120(3):621-3.

Organick et al., Random access in large-scale DNA data storage. Nature Biotechnology, Advance Online Publication, 8 pages, 2018.

(56) References Cited

OTHER PUBLICATIONS

Organick et al., Scaling up DNA data storage and random access retrieval, bioRxiv, preprint first posted online Mar. 7, 2017, 14 pages.
Pan, et al. An approach for global scanning of single nucleotide variations. Proc Natl Acad Sci U S A. Jul. 9, 2002;99(14):9346-51.
Pankiewicz. Fluorinated nucleosides. Carbohydr Res. Jul. 10, 2000;327(1-2):87-105.
PCT/US14/049834 International Preliminary Report on Patentability dated Feb. 18, 2016.
PCT/US2014/049834 International Search Report and Written Opinion dated Mar. 19, 2015.
PCT/US2014/049834, "Invitation to Pay Additional Fees and, where applicable, protest fee," dated Jan. 5, 2015.
PCT/US2015/043605 International Preliminary Report on Patentability dated Feb. 16, 2017.
PCT/US2015/043605 International Search Report and Written Opinion dated Jan. 6, 2016.
PCT/US2015/043605 Invitation to Pay Additional Fees dated Oct. 28, 2015.
PCT/US2016/016459 International Preliminary Report on Patentability dated Aug. 17, 2017.
PCT/US2016/016459 International Search Report and Written Opinion dated Apr. 13, 2016.
PCT/US2016/016636 International Preliminary Report on Patentability dated Aug. 17, 2017.
PCT/US2016/016636 International Search Report and Written Opinion dated May 2, 2016.
PCT/US2016/028699 International Preliminary Report on Patentability dated Nov. 2, 2017.
PCT/US2016/028699 International Search Report and Written Opinion dated Jul. 29, 2016.
PCT/US2016/031674 International Preliminary Report on Patentability dated Nov. 23, 2017.
PCT/US2016/031674 International Search Report and Written Opinion dated Aug. 11, 2016.
PCT/US2016/052336 International Search Report and Written Opinion dated Dec. 7, 2016.
PCT/US2016/052916 International Search Report and Written Opinion dated Dec. 30, 2016.
PCT/US2016/064270 International Search Report and Written Opinion dated Apr. 28, 2017.
PCT/US2017/026232 International Search Report and Written Opinion dated Aug. 28, 2017.
PCT/US2017/036868 International Search Report and Written Opinion dated Aug. 11, 2017.
PCT/US2017/045105 International Search Report and Written Opinion dated Oct. 20, 2017.
PCT/US2017/052305 International Search Report and Written Opinion dated Feb. 2, 2018.
Pease, et al. Light-generated oligonucleotide arrays for rapid DNA sequence analysis. Proc Natl Acad Sci U S A. May 24, 1994;91(11):5022-6.
Peisajovich, et al. BBF RFC 28: A method for combinatorial multi-part assembly based on the type-IIs restriction enzyme aarI. Sep. 16, 2009, 7 pages.
Pellois, et al. "Individually addressable parallel peptide synthesis on microchips", Nature Biotechnology, vol. 20, 922-926 (Sep. 2002).
Petersen, et al. LNA: a versatile tool for therapeutics and genomics. Trends Biotechnol. Feb. 2003;21(2):74-81.
Pierce and Wangh, Linear-after-the-exponential polymerase chain reaction and allied technologies Real-time detection strategies for rapid, reliable diagnosis from single cells Methods Mol. Med. 132:65-85 (2007) (Abstract only).
Pirrung. How to make a DNA chip. Angew. Chem. Int. Ed., 41:1276-1289, 2002.
Plesa et al., Multiplexed gene synthesis in emulsions for exploring protein functional landscapes. Science, 10.1126/science.aao5167, 10 pages, 2018.
Pon. Solid-phase supports for oligonucleotide synthesis. Methods Mol Biol. 1993;20:465-96.
Poster. Reimagine Genome Scale Research. 2016, 1 page. Available at http://www2.twistbioscience.com/Oligo_Pools_CRISPR_poster.
Powers et al. Optimal strategies for the chemical and enzymatic synthesis of bihelical deoxyribonucleic acids. J Am Chem Soc., 97(4):875-884, 1975.
Pray. "Discovery of DNA Structure and Function: Watson and Crick," Nature Education, 2008, 6 pages. available at: http://www.nature.com/scitable/topicpage/discovery-of-dna-structure-and-function-watson-397.
Prodromou, et al. Recursive PCR: a novel technique for total gene synthesis. Protein Eng. Dec. 1992;5(8):827-9.
Qian and Winfree, Scaling up digital circuit computation with DNA strand displacement cascades. Science, 332(6034):196-1201, 2011.
Qian, et al., Neural network computation with DNA strand displacement cascades, Nature, 475(7356):368-372, 2011.
Quan et al., "Parallel on-chip gene synthesis and application to optimization of protein expression," Nature Biotechnology, 29(5):449-452, 2011.
Rafalski and Morgante, Corn and humans: recombination and linkage disequilibrium in two genomes of similar size. Trends in Genetics, 20(2):103-111, 2004.
Raje and Murma, A Review of electrohydrodynamic-inkjet printing technology. International Journal of Emerging Technology and Advanced Engineering, 4(5):174-183, 2014.
Rastegari, et al., XNOR-Net: ImageNet Classification Using Binary Convolutional Neural Networks, in ECCV 2016, Part IV, LNCS 9908, p. 525-542, 2016.
Reimagine SequenceSpace, Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source "flat excimer," 16 pages dated Jan. 2016. From: http://www.hamamatsu.com/jp/en/product/category/1001/3026/index.html.
Richmond, et al. Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science—A Tradition of Premium Quality and Scientific Support. FAQS and Ordering Guide. Roche Applied Science. Accessed Jan. 12, 2015, 37 pages.
Rogozin et al., Origin and evolution of spliceosomal introns. Biology Direct, 7:11, 2012.
Ruminy, et al., "Long-range identification of hepatocyte nuclear factor-3 (FoxA) high and low-affinity binding Sites with a chimeric nuclease", J. Mol. Bioi., vol. 310, 523-535 (2001).
Saaem et al., In situ synthesis of DNA microarray on functionalized cyclic olefin copolymer substrate ACS Applied Materials & Interfaces, 2(2):491-497, 2010.
Saboulard, et al. High-throughput site-directed mutagenesis using oligonucleotides synthesized on DNA chips. Biotechniques. Sep. 2005;39(3):363-8.
Sacconi, L. et al., Three-dimensional magneto-optic trap for micro-object manipulation, Optics Letters, vol. 26, No. 17, 1359-1361 (Sep. 1, 2001).
Saiki et al. Analysis of enzymatically amplified beta-globin and HLA-DQ alpha DNA with allele-specific oligonucleotide probes. Nature 324:163-166 (1986).
Sandhu, et al. Dual asymmetric PCR: one-step construction of synthetic genes. Biotechniques. Jan. 1992;12(1):14-6.
Sargolzaei et al., Extent of linkage disequilibrium in Holstein cattle in North America. J.Dairy Science, 91:2106-2117, 2007.
Schaller, et al. Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing et al. Microchip electrophoresis: a method for high-speed SNP detection. Nucleic Acids Res 28(9):E43 (2000).

(56) References Cited

OTHER PUBLICATIONS

Schmitt et al., New strategies in engineering T-cell receptor gene-modified T cells to more effectively target malignancies. Clinical Cancer Research, 21(23):5191-5197, 2015.
Seelig, et al., Enzyme-Free Nucleic Acid Logic Circuits, Science 314(5805):1585-1588, 2006.
Sharpe and Mount, Genetically modified T cells in cancer therapy: opportunities and challenges. Disease Models and Mechanisms, 8:337-350, 2015.
Sierzchala, Agnieszka B. et al., "Solid-phase oligodeoxynucleotide synthesis : a two-step cycle using peroxy anion eprotection", J. Am. Chem. Soc., vol. 125, No. 44, 13427-13441 (2003).
Simonyan and Zisserman, Very Deep Convolutional Networks for Large-Scale Image Recognition, Published as a conference paper at Int. Conf. Learn. Represent., pp. 1-14, 2015.
Singh-Gasson, Sangeet et al., Maskless fabrication of light-directed olxyonucleotide microarrays using a digital micromirror array, Nature Biotechnology, vol. 17, 974-978 (Oct. 1999).
Smith, et al. Generating a synthetic genome by whole genome assembly: phiX174 bacteriophage from synthetic oligonucleotides. Proc Natl Acad Sci U S A. Dec. 23, 2003;100(26):15440-5.
Smith, et al. Generation of cohesive ends on PCR products by UDG-mediated excision of dU, and application for cloning into restriction digest-linearized vectors. PCR Methods Appl. May 1993;2(4):328-32.
Smith, Jane et al., "Mutation detection with MutH, MutL, and MutS mismatch repair proteins", Proc. Natl. Acad. Sci. USA, vol. 93, 4374-4379 (Apr. 1996).
Smith Jane et al., "Removal of Polymerase-Produced mutant sequences from PCR products", Proc. Natl. Acad. Sci. USA, vol. 94, 6847-6850 (Jun. 1997).
Smith, Steven B. et al., "Direct mechanical measurements of the elasticity of single DNA molecules using magnetic beads", Science, vol. 258, 1122-1126 (Nov. 13, 1992).
Soni, et al. Progress toward ultrafast DNA sequencing using solid-state nanopores. Clin Chem. Nov. 2007;53(11):1996-2001.
Southern, et al. Analyzing and comparing nucleic acid sequences by hybridization to arrays of oligonucleotides: evaluation using experimental models. Genomics. Aug. 1992;13(4):1008-17.
Sproat, et al. An efficient method for the isolation and purification of oligoribonucleotides. Nucleosides & Nucleotides. 1995; 14(1 &2):255-273.
Srivannavit et al., Design and fabrication of microwell array chips for a solution-based, photogenerated acid-catalyzed parallel oligonucleotide DNA synthesis. Sensors and Actuators A, 116:150-160, 2004.
Srivastava et al., "RNA synthesis: phosphoramidites for RNA synthesis in the reverse direction. Highly efficient synthesis and application to convenient introduction of ligands, chromophores and modifications of synthetic RNA at the 3'-end", Nucleic Acids Symposium Series, 52(1):103-104, 2008.
Steel, The Flow-Thru Chip A Three-dimensional biochip platform. In: Schena, Microarray Biochip Technology, Chapter 5, Natick, MA: Eaton Publishing, 2000, 33 pages.
Stemmer, et al. Single-step assembly of a gene and entire plasmid from large Numbers of oligodeoxyribonucleotides. Gene. Oct. 16, 1995;164(1):49-53.
Stryer. "DNA Probes and genes can be synthesized by automated solid-phase methods." Biochemistry, 3rd edition, New York: W.H. Freeman and Company, 1988; 123-125.
Stutz, et al. Novel fluoride-labile nucleobase-protecting groups for the synthesis of 3'(2')-O-amino-acylated RNA sequences. Helv. Chim. Acta. 2000; 83(9):2477-2503.
Takahashi, Cell-free cloning using multiply-primed rolling circle amplification with modified RNA primers. Biotechniques. Jul. 2009;47(1):609-15.
Tanase, M. et al., "Magnetic trapping of multicomponent nanowires", The Johns Hopkins University, Baltimore, Maryland, p. 1-3 (Jun. 25, 2001).
Taylor et al., Impact of surface chemistry and blocking strategies on DNA microarrays. Nucleic Acids Research, 31(16):e87, 19 pages, 2003.
The Hood Laboratory, "Beta Group." Assembly Manual for the POSaM: The ISB Piezoelelctric Oligonucleotide Synthesizer and Microarrayer, Inkjet Microarrayer Manual Version 1.2, 50 pages, May 28, 2004.
The SLIC, Gibson, CPEC and SLiCE assembly methods (and GeneArt Seamless, In-Fusion Cloning). 5 pages, available online Sep. 2, 2010.
Tian, et al. Accurate multiplex gene synthesis from programmable DNA microchips. Nature. Dec. 23, 2004;432(7020):1050-4.
Tsai et al., Dimeric CRISPR RNA-guided Fokl nucleases for highly specific genome editing Nat. Biotechnol., 32(6):569-576, 2014.
Unger, et al. Monolithic microfabricated valves and pumps by multilayer soft lithography. Science. Apr. 7, 2000;288(5463):113-6.
U.S. Appl. No. 14/241,874 Office Action dated Feb. 27, 2017.
U.S. Appl. No. 14/452,429 Notice of Allowance dated Jun. 7, 2016.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/154,879 Notice of Allowance dated Feb. 1, 2017.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2016.
U.S. Appl. No. 15/377,547 Office Action dated Mar. 24, 2017.
U.S. Appl. No. 15/377,547 Office Action dated Nov. 30, 2017.
U.S. Appl. No. 15/602,991 Notice of Allowance dated Oct. 25, 2017.
U.S. Appl. No. 15/602,991 Office Action dated Sep. 21, 2017.
U.S. Appl. No. 15/603,013 Office Action dated Jan. 30, 2018.
U.S. Appl. No. 15/603,013 Office Action dated Oct. 20, 2017.
U.S. Appl. No. 15/682,100 Office Action dated Jan. 2, 2018.
U.S. Appl. No. 15/682,100 Restriction Requirement dated Nov. 8, 2017.
U.S. Appl. No. 14/452,429 Office Action dated Apr. 9, 2015.
Vaijayanthi, et al. Recent advances in oligonucleotide synthesis and their applications. Indian J Biochem Biophys. Dec. 2003;40(6):377-91.
Van Den Brulle, et al. A novel solid phase technology for high-throughput gene synthesis. Biotechniques. 2008; 45(3):340-343.
Van Tassell et al., SNP discovery and allele frequency estimation by deep sequencing of reduced representation libraries. Nature Methods, 5:247-252, 2008.
Vargeese, et al. Efficient activation of nucleoside phosphoramidites with 4,5-dicyanoimidazole during oligonucleotide synthesis. Nucleic Acids Res. Feb. 15, 1998;26(4):1046-50.
Verma et al. Modified oligonucleotides: synthesis and strategy for users. Annu Rev Biochem 67:99-134 (1998).

(56) References Cited

OTHER PUBLICATIONS

Vincent, et al. Helicase-dependent isothermal DNA amplification. EMBO Rep. Aug. 2004;5(8):795-800.
Visscher et al., "Construction of multiple-beam optical traps with nanometer-resolution position sensing", IEEE Journal of Selected Topics in Quantum Electronics, vol. 2, No. 4, 1066-1076 (Dec. 1996.
Voldmans Joel et al., "Holding forces of single-particle dielectrophoretic traps." Biophysical Journal, vol. 80, No. 1, 531-541 (Jan. 2001).
Vos, et al. AFLP:A new technique for DNA fingerprinting. Nucleic Acids Res. Nov. 11, 1995;23(21):4407-14.
Wagner et al., "Nucleotides, Part LXV, Synthesis of 2'-Deoxyribonucleoside 5'-Phosphoramidites: New Building Blocks for the Inverse (5'-3')-0iigonucleotide Approach." Helvetica Chimica Acta, 83(8):2023-2035, 2000.
Wah, David A. et al., "Structure of Fok I has implications for DNA cleavage", Proc. Natl. Acad. Sci. USA, vol. 95, 10564-10569 (Sep. 1998).
Wah, David A. et al., "Structure of the multimodular endonuclease Fok I bound to DNA", Nature, vol. 388, 97-100 ( Jul. 1997).
Walker, et al. Strand displacement amplification—an isothermal, in vitro DNA amplification technique. Nucleic Acids Res. Apr. 11, 1992;20(7):1691-6.
Wan et al., Deep Learning for Content-Based Image Retrieval: A comprehensive study. in Proceedings of the 22nd ACM International Conference on Multimedia—Nov. 3-7, 2014, Orlando, FL, p. 157-166, 2014.
Weber, et al. A modular cloning system for standardized assembly of multigene constructs. PLoS One. Feb. 18, 2011;6(2):e16765.
Welz, et al. 5-(Benzylmercapto)-1H-tetrazole as activator for 2'-O-TBDMS phosphoramidite building blocks in RNA synthesis. Tetrahedron Lett. 2002; 43(5):795-797.
Westin et al., Anchored multiplex amplification on a microelectronic chip array Nature Biotechnology, 18:199-202 (2000) (abstract only).
Whitehouse, Adrian et al. "Analysis of the mismatch and insertion/deletion binding properties of Thermus thermophilus, HB8, MutS", Biochemical and Biophysical Research Communications, vol. 233, 834-837 (1997).
Wiedenheft et al., RNA-guided genetic silencing systems in bacteria and archaea. Nature, 482:331-338, 2012.
Wijshoff, Herman. Structure and fluid-dynamics in Piezo inkjet printheads. Thesis. Venio, The Netherlands, published 2008, p. 1-185.
Wirtz, Denis, "Direct measurement of the transport properties of a single DNA molecule", Physical Review Letters, vol. 75, No. 12, 2436-2439 (Sep. 18, 1995).
Withers-Martinez, Chrislaine et al., "PCR-based gene synthesis as an efficient approach for expression of the A+ T-rich malaria genome", Protein Engineering, vol. 12, No. 12, 1113-1120 (1999).
Wood, Richard D. et al., "Human DNA repair genes", Science, vol. 291, 1284-1289 (Feb. 16, 2001).
Wosnick, et al. Rapid construction of large synthetic genes: total chemical synthesis of two different versions of the bovine prochymosin gene. Gene. 1987;60(1):115-27.
Wright and Church, An open-source oligomicroarray standard for human and mouse. Nature Biotechnology, 20:1082-1083, 2002.
Wu, et al. RNA-mediated gene assembly from DNA arrays. Angew Chem Int Ed Engl. May 7, 2012;51(19):4628-32.
Wu, et al. Specificity of the nick-closing activity of bacteriophage T4 DNA ligase. Gene. 1989;76(2):245-54.
Wu, Xing-Zheng et al., "An improvement of the on-line electrophoretic concentration method for capillary electrophoresis of proteins an experimental factors affecting he concentration effect", Analytical Sciences, vol. 16, 329-331 (Mar. 2000).
Xiong, et al. A simple, rapid, high-fidelity and cost-effective PCR-based two-step DNA synthesis method for long gene sequences. Nucleic Acids Res. 2004, 32(12):e98.

Xiong et al., Chemical gene synthesis: Strategies, softwares, error corrections, and applications. FEMS Microbiol. Rev., 32:522-540, 2008.
Xiong, et al. Non-polymerase-cycling-assembly-based chemical gene synthesis: Strategies, methods, and progress. Biotechnology Advances. 26(2):121-134, 2008.
Xu et al., Design of 240,000 orthogonal 25mer DNA barcode probes. PNAS, 106(7):2289-2294, 2009.
Yang, et al "Purification, cloning, and characterization of the CEL I nuclease", Biochemistry, 39(13):3533-35, 2000.
Yazdi, et al., A Rewritable, Random-Access DNA-Based Storage System, Scientific Reports, 5, Article No. 14138, 27 pages, 2015.
Yehezkel et al., De novo DNA synthesis using single molecule PCR Nucleic Acids Research, 36(17):e107, 2008.
Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).
Youil, Rima et al., "Detection of 81 of 81 known mouse Beta-Giobin promoter mutations with T4 Endonuclease VII. The EMC Method", Genomics, 32:431-435, 1996.
Young, et al. Two-step total gene synthesis method. Nucleic Acids Res. 32(7):e59, 2004.
Zhang and Seelig, Dynamic DNA nanotechnology using strand-displacement reactions, Nat. Chem., 3(2):103-113, 2011.
Zheleznaya, et al. Nicking endonucleases. Biochemistry (Mosc). 74(13):1457-66, 2009.
Zhirnov et al., Nucleic acid memory. Nature Materials, 15:366, 2016.
Zhou et al., Microfluidic PicoArray synthesis of oligodeoxynucleotides and simultaneous assembling of multiple DNA sequences Nucleic Acids Research, 32(18):5409-5417, 2004.
Alberts et al.: Molecular Biology of the Cell. 4th edition. New York: Garland Science; 2002. The Generation of Antibody Diversity. https://www.ncbi.nlm.nih.gov/books/NBK26860/.
Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.
Chervin et al.: Design of T-cell receptor libraries with diverse binding properties to examine adoptive T-cell responses. Gene Therapy. 20(6):634-644 (2012).
Cui et al.: Information Security Technology Based on DNA Computing. International Workshop on Anti-Counterfeiting, Security and Identification (ASID); IEEE Xplore 4 pages (2007).
European Patent Application No. 17844060.8 Extended Search Report dated Apr. 20, 2020.
European Patent Application No. 17872347.4 Extended European Search Report dated Jun. 30, 2020.
European Patent Application No. 17881617.9 European Search Report and Written Opinion dated Jul. 2, 2020.
Goodwin et al.: immunoglobulin heavy chain variable region, partial [*Homo sapiens*]. Genbank entry (online). National Institute of Biotechnology Information. (2018) https://www.ncbi.nim.nih.gov/protein/AXA12486.1.
Hauser et al.: Trends in GPCR drug discovery: new agents, targets and indications. Nature Reviews Drug Discovery, 16, 829-842 (2017). doi:10.1038/nrd.2017.178 https://www.nature.com/articles/nrd.2017.178.
Hopcroft et al.: What is the Young's Modulus of Silicon?. Journal of Microelectromechanical Systems. 19(2):229-238 (2010).
Hötzel et al.: a strategy for risk mitigation of antibodies with fast clearance. mAbs, 4(6), 753-760 (2012). doi:10.4161/mabs.22189 https://www.ncbi.nlm.nih.gov/pubmed/23778268.
Jaiswal et al.: An architecture for creating collaborative semantically capable scientific data sharing infrastructures. Proceeding WIDM '06 Proceedings of the 8th annual ACM international workshop on Web information and data management. ACM Digital Library pp. 75-82 (2006).

(56) References Cited

OTHER PUBLICATIONS

Malecek et al.: Engineering improved T cell receptors using an alanine-scan guided T cell display selection system. Journal of Immunological Methods. Elsevier Science Publishers. 392(1):1-11 (2013).
(Novartis Institutes for Biomedical Research) Immunoglobulin Heavy Chain [*Homo sapiens*]. National Center for Biotechnology Information. Genbank Entry. pp. 1-2 (2018) https://www.ncbi.nlm.nih.gov/nuccore/MH975524.1ttps://https://www.ncbi.nlm.nih.gov/nuccore/MH975524.1.
(Novartis Institutes for Biomedical Research) Immunoglobulin Lambda Chain [*Homo sapiens*]. National Center for Biotechnology Information. Genbank Entry. pp. 1-2 (2018) https://www.ncbi.nlm.nih.gov/nuccore/MH975524.1.
PCT/US2018/037152 International Preliminary Report on Patentability dated Dec. 17, 2019.
PCT/US2018/037161 International Preliminary Report on Patentability dated Dec. 17, 2019.
PCT/US2018/050511 International Preliminary Report on Patentability dated Mar. 17, 2020.
PCT/US2018/056783 International Preliminary Report on Patentability dated Apr. 30, 2020.
PCT/US2018/057857 International Preliminary Report on Patentability dated Apr. 28, 2020.
PCT/US2019/012218 International Preliminary Report on Patentability dated Jul. 16, 2020.
PCT/US2019/068435 International Search Report and Written Opinion dated Apr. 23, 2020.
PCT/US2020/019371 International Search Report and Written Opinion dated Jun. 25, 2020.
PCT/US2020/019986 International Search Report and Written Opinion dated Jul. 29, 2020.
PCT/US2020/019986 Invitation to Pay Additional Fees dated Jun. 5, 2020.
PCT/US2020/019988 International Search Report and Written Opinion dated Jul. 29, 2020.
PCT/US2020/019988 Invitation to Pay Additional Fees dated Jun. 8, 2020.
Pierce et al.: Linear-after-the-exponential polymerase chain reaction and allied technologies. Real-time detection strategies for rapid, reliable diagnosis from single cells. Methods Mol Med. 2007;132:65-85.
U.S. Appl. No. 15/151,316 Final Office Action dated Jul. 9, 2020.
U.S. Appl. No. 15/272,004 Office Action dated Jun. 12, 2020.
U.S. Appl. No. 15/619,322 Final Office Action dated Mar. 30, 2020.
U.S. Appl. No. 15/816,995 Office Action dated May 19, 2020.
U.S. Appl. No. 15/835,342 Final Office Action dated Sep. 8, 2020.
U.S. Appl. No. 15/921,479 Final Office Action dated Jun. 15, 2020.
U.S. Appl. No. 15/991,992 Office Action dated May 21, 2020.
U.S. Appl. No. 16/031,784 Final Office Action dated May 12, 2020.
U.S. Appl. No. 16/039,256 Office Action dated Aug. 20, 2020.
U.S. Appl. No. 16/039,256 Restriction Requirement dated May 18, 2020.
U.S. Appl. No. 16/128,372 Restriction Requirement dated May 18, 2020.
U.S. Appl. No. 16/239,453 Office Action dated May 11, 2020.
U.S. Appl. No. 16/530,717 Final Office Action dated Apr. 15, 2020.
van der Velde: Thesis. Finding the Strength of Glass. Delft University of Technology. 1-16 (2015).
EPP104742EP51 Search Report Opinion dated Nov. 13, 2020.

\* cited by examiner

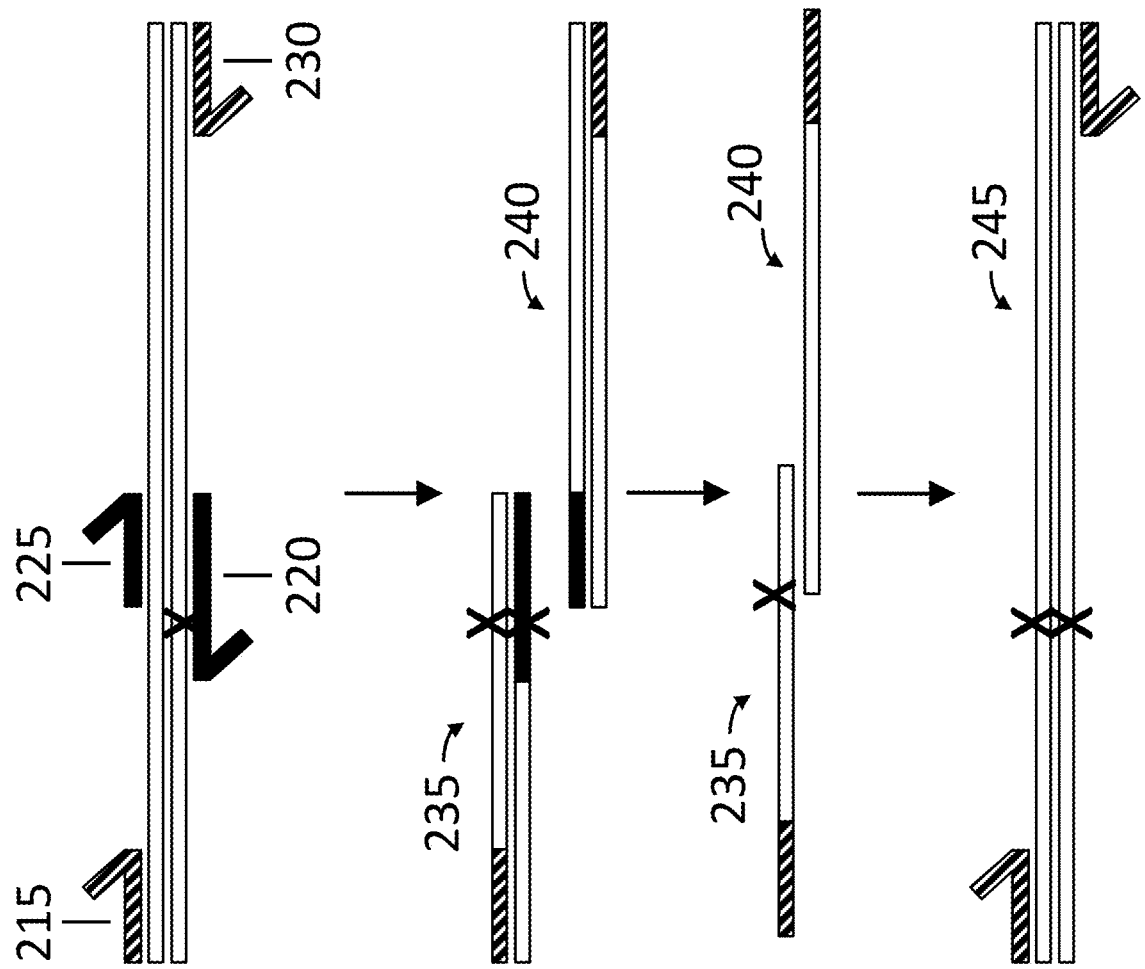

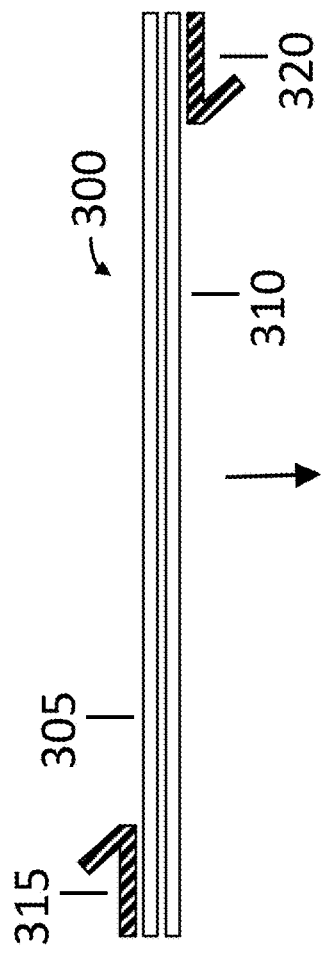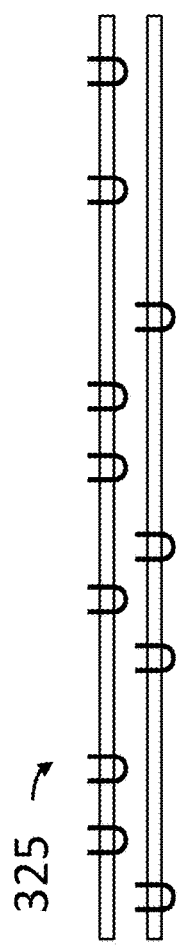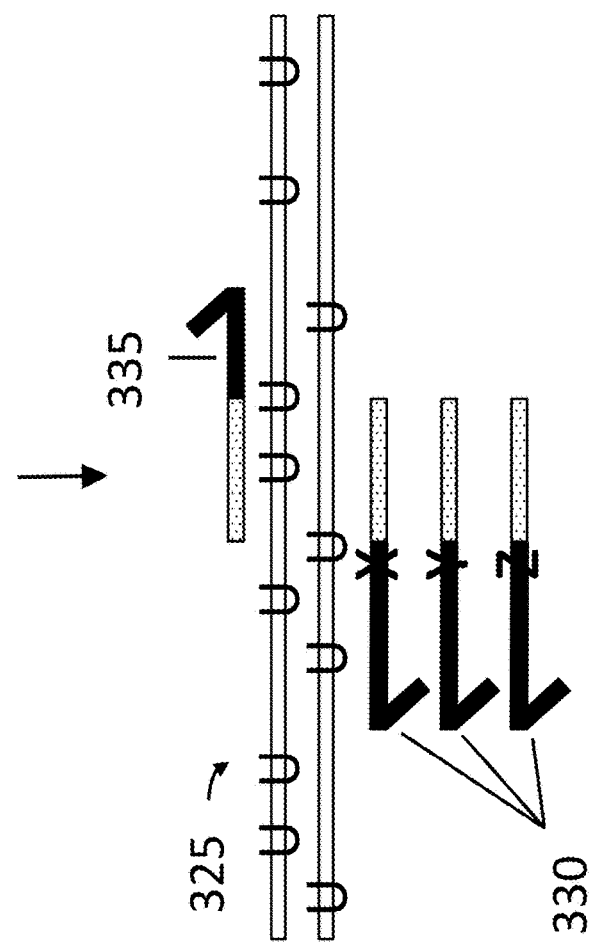
FIG. 3A
FIG. 3B
FIG. 3C

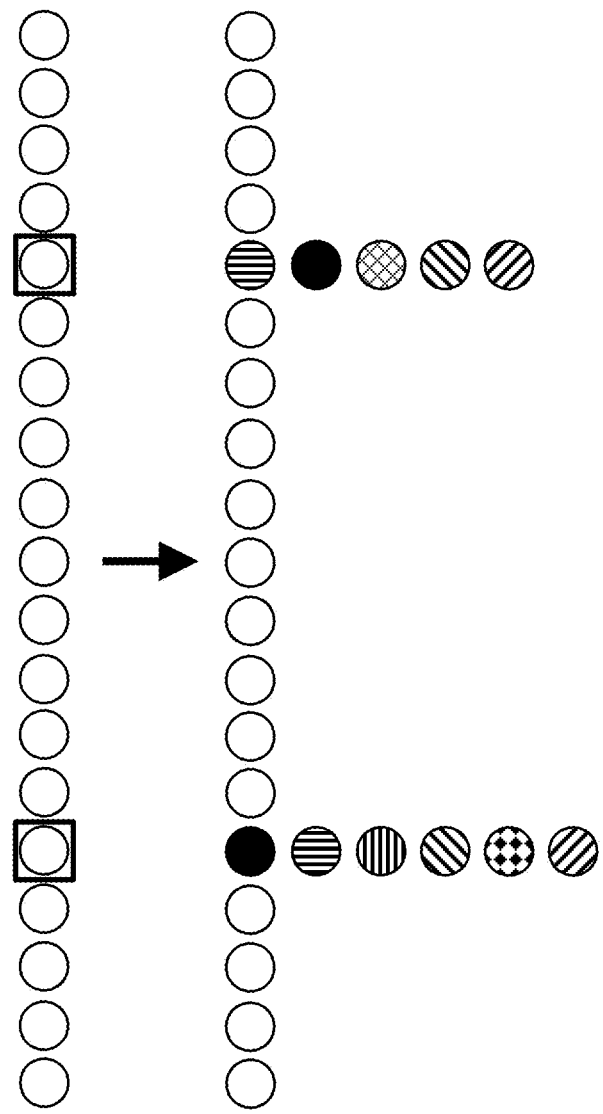

VARIANT LIBRARIES OF THE IMMUNOLOGICAL SYNAPSE AND SYNTHESIS THEREOF

CROSS-REFERENCE

This application claims benefit of U.S. Provisional Patent Application No. 62/471,810 filed on Mar. 15, 2017, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 9, 2018, is named 44854-733_201_SL.txt and is 19,476 bytes in size.

BACKGROUND

The cornerstone of synthetic biology is the design, build, and test process—an iterative process that requires DNA, to be made accessible for rapid and affordable generation and optimization of these custom pathways and organisms. In the design phase, the A, C, T and G nucleotides that constitute DNA are formulated into the various gene sequences that would comprise the locus or the pathway of interest, with each sequence variant representing a specific hypothesis that will be tested. These variant gene sequences represent subsets of sequence space, a concept that originated in evolutionary biology and pertains to the totality of sequences that make up genes, genomes, transcriptome and proteome.

Many different variants are typically designed for each design-build-test cycle to enable adequate sampling of sequence space and maximize the probability of an optimized design. Though straightforward in concept, process bottlenecks around speed, throughput and quality of conventional synthesis methods dampen the pace at which this cycle advances, extending development time. The inability to sufficiently explore sequence space due to the high cost of acutely accurate DNA and the limited throughput of current synthesis technologies remains the rate-limiting step.

Beginning with the build phase, two processes are noteworthy: oligonucleotide synthesis and gene synthesis. Historically, synthesis of different gene variants was accomplished through molecular cloning. While robust, this approach is not scalable. Early chemical gene synthesis efforts focused on producing a large number of oligonucleotides with overlapping sequence homology. These were then pooled and subjected to multiple rounds of polymerase chain reaction (PCR), enabling concatenation of the overlapping oligonucleotides into a full length double stranded gene. A number of factors hinder this method, including time-consuming and labor-intensive construction, requirement of high volumes of phosphoramidites, an expensive raw material, and production of nanomole amounts of the final product, significantly less than required for downstream steps, and a large number of separate oligonucleotides required one 96 well plate to set up the synthesis of one gene.

Synthesizing oligonucleotides on microarrays provided a significant increase in the throughput of gene synthesis. A large number of oligonucleotides could be synthesized on the microarray surface, then cleaved off and pooled together. Each oligonucleotide destined for a specific gene contains a unique barcode sequence that enabled that specific subpopulation of oligonucleotides to be depooled and assembled into the gene of interest. In this phase of the process, each subpool is transferred into one well in a 96 well plate, increasing throughput to 96 genes. While this is two orders of magnitude higher in throughput than the classical method, it still does not adequately support the design, build, test cycles that require thousands of sequences at one time due to a lack of cost efficiency and slow turnaround times. Thus, there is a need for more efficient generation of variant sequence libraries.

The immune system has the ability to seek and destroy harmful cells. T cells play an important role in such a process. As such, therapies comprising genetically modified T cells to teach the immune system to recognize and eliminate malignant cells are alternative therapies that may be used to treat diseases such as cancer. In particular, genetically modified T cells that express chimeric antigen receptors (CARs) may be designed to target deleterious cells, such as cancer cells. However, CAR therapies require further optimization due to their ability to cause undesirable effects such as on-target off-tumor toxicity, autoimmunity, host-graft toxicity, and sometimes death. Thus, there is a need for improved compositions and methods for cancer therapies utilizing CAR therapies.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

Provided herein are nucleic acid libraries, wherein the nucleic acid library comprises at least 10,000 nucleic acids, wherein each nucleic acid encodes for a preselected variant of a reference sequence that encodes for a chimeric antigen receptor or a functional domain thereof. Further provided herein are nucleic acid libraries, wherein the functional domain of the chimeric antigen receptor comprises an antigen recognition domain, a hinge domain, a transmembrane domain, or an intracellular domain. Further provided herein are nucleic acid libraries, wherein the library comprises at least 1,000,000 nucleic acids. Further provided herein are nucleic acid libraries, wherein each nucleic acid is 100 bases to 2000 bases in length. Further provided herein are nucleic acid libraries, wherein each nucleic acid is attached to a vector sequence. Further provided herein are nucleic acid libraries, wherein the vector sequence is a viral vector sequence.

Provided herein are nucleic acid libraries, wherein the nucleic acid library comprises a plurality of nucleic acids, wherein each nucleic acid encodes for a preselected variant of a reference sequence that encodes for a chimeric antigen receptor or a functional domain thereof, wherein the plurality of nucleic acids comprises all variations for at least two positions in the reference sequence, and wherein the at least two positions encode sequences from 5 to 20 different codons. Further provided herein are nucleic acid libraries, wherein the functional domain of the chimeric antigen receptor comprises an antigen recognition domain, a hinge domain, a transmembrane domain, or an intracellular domain. Further provided herein are nucleic acid libraries, wherein the plurality of nucleic acids comprises all variations for 2, 3, 4, or 5 positions in the reference sequence.

Further provided herein are nucleic acid libraries, wherein the at least two positions encode sequences from 10 to 20 different codons. Further provided herein are nucleic acid libraries, wherein the at least two positions encode sequences for about 10 different codons. Further provided herein are nucleic acid libraries, wherein each nucleic acid is 100 bases to 2000 bases in length.

Provided herein are oligonucleotide libraries, the oligonucleotide library comprising at least 10,000 oligonucleotides, wherein each oligonucleotide encodes for a preselected variant of a reference sequence that encodes for a region of a chimeric antigen receptor, wherein the region comprises a portion of an antigen recognition domain, a hinge domain, a transmembrane domain, or an intracellular domain. Further provided herein are oligonucleotide libraries, wherein the library comprises at least 1,000,000 oligonucleotides. Further provided herein are oligonucleotide libraries, wherein each oligonucleotide is 12 to 500 bases in length. Further provided herein are oligonucleotide libraries, wherein each oligonucleotide is attached to a vector sequence.

Provided herein are oligonucleotide libraries, wherein the oligonucleotide library comprises a plurality of oligonucleotides, wherein each oligonucleotide encodes for a preselected variant of a reference sequence that encodes for a region of a chimeric antigen receptor, wherein the region comprises a portion of an antigen recognition domain, a hinge domain, a transmembrane domain, or an intracellular domain, wherein each oligonucleotide is at least 12 bases in length, wherein the plurality of oligonucleotides comprises all variations for at least two positions in the reference sequence, and wherein the at least two positions encode sequences from 5 to 20 different codons. Further provided herein are oligonucleotide libraries, wherein the plurality of oligonucleotides comprises all variations for 2, 3, 4, or 5 positions. Further provided herein are oligonucleotide libraries, wherein the at least two positions encode sequences from 10 to 20 different codons. Further provided herein are oligonucleotide libraries, wherein the at least two positions encode sequences for about 10 different codons. Further provided herein are oligonucleotide libraries, wherein each oligonucleotide is 12 to 500 bases in length.

Provided herein are nucleic acid libraries comprising at least 400 nucleic acids, wherein a first plurality of the at least 400 nucleic acids encodes for a variant of a reference sequence that encodes for an antigen recognition domain, and wherein a second plurality of the at least 400 nucleic acids encodes for a variant of a reference sequence that encodes for a hinge domain, a transmembrane domain, or an intracellular domain of a chimeric antigen receptor (CAR). Further provided herein are nucleic acid libraries, wherein each nucleic acid is at least 100 bases in length. Further provided herein are nucleic acid libraries, wherein each nucleic acid is 100 to 2000 bases in length. Further provided herein are nucleic acid libraries, wherein the first plurality of the at least 400 nucleic acids comprises all variations for at least two positions in the reference sequence. Further provided herein are nucleic acid libraries, wherein the first plurality of the at least 400 nucleic acids comprises all variations for 2, 3, 4, or 5 positions in the reference sequence. Further provided herein are nucleic acid libraries, wherein the second plurality of the at least 400 nucleic acids comprises all variations for at least two positions in the reference sequence. Further provided herein are nucleic acid libraries, wherein the second plurality of the at least 400 nucleic acids comprises all variations for 2, 3, 4, or 5 positions in the reference sequence. Further provided herein are nucleic acid libraries, wherein the at least two positions encode sequences from 5 to 20 different codons. Further provided herein are nucleic acid libraries, wherein the at least two positions encode sequences from 10 to 20 different codons. Further provided herein are nucleic acid libraries, wherein the at least two positions encode sequences for about 10 different codons.

Provided herein are methods of synthesizing a nucleic acid library, comprising: (a) providing a first set of preselected oligonucleotide sequences encoding for at least 400 sequences of a chimeric antigen receptor gene or gene fragment, wherein each sequence comprises at least one variation of at least two preselected codons for an amino acid residue in an antigen recognition domain; (b) synthesizing the first set of preselected oligonucleotide sequences; and (c) screening a first activity for proteins encoded by the first set of oligonucleotide sequences, wherein the first activity is specificity, avidity, affinity, stability, or expression. Further provided herein are methods of synthesizing a nucleic acid library, wherein the antigen is a cancer antigen. Further provided herein are methods of synthesizing a nucleic acid library, wherein the cancer antigen is MAGE A3, MAGE A12, MAGE A2, MAGE A6, NY-ESO-1, or CEA. Further provided herein are methods of synthesizing a nucleic acid library, wherein each sequence comprises up to 100 variations at preselected codons for amino acid residues in the antigen recognition domain. Further provided herein are methods of synthesizing a nucleic acid library, wherein each sequence comprises up to 30 variations at preselected codons for amino acid residues in the antigen recognition domain. Further provided herein are methods of synthesizing a nucleic acid library further comprising (a) providing a second set of preselected oligonucleotide sequences encoding for at least one sequence of a chimeric antigen receptor gene or gene fragment, where each sequence comprises at least one variation at a preselected codon for an amino acid residue in the chimeric antigen receptor in a hinge domain, a transmembrane domain, or an intracellular domain; (b) synthesizing the second set of preselected oligonucleotide sequences; and (c) screening a second activity for proteins encoded by the second set of oligonucleotide sequences, wherein the second activity is specificity, avidity, affinity, stability, or expression, and wherein the second activity is different from the first activity.

Provided herein is an oligonucleotide library, the library comprising at least 10,000 variant oligonucleotides, wherein each variant oligonucleotide is at least 12 bases in length, wherein each variant oligonucleotide encodes for a variant of a reference sequence that encodes for an antigen recognition domain, a hinge domain, a transmembrane domain, or an intracellular domain of a chimeric antigen receptor, and wherein at least 80% of the variant oligonucleotides have no errors compared to the predetermined sequences without correcting errors. Further provided herein is an oligonucleotide library wherein the library comprises at least 1,000,000 variant oligonucleotides. Further provided herein is an oligonucleotide library, wherein each variant oligonucleotide is 20 to 500 bases in length. Further provided herein is an oligonucleotide library wherein at least 90% of the variant oligonucleotides have no errors compared to the predetermined sequences without correcting errors.

Provided herein is a nucleic acid library, the library comprising at least 10,000 variant nucleic acids, wherein each variant nucleic acid encodes for a variant of a reference sequence for a chimeric antigen receptor, wherein the variation occurs in the sequence for an antigen recognition domain, a hinge domain, a transmembrane domain, or an intracellular domain of a chimeric antigen receptor, and wherein at least 70% of the variant nucleic acids have no errors compared to the predetermined sequences without correcting errors. Further provided herein is a nucleic acid library wherein the library comprises about 10,000,000 variant nucleic acids. Further provided herein is a nucleic acid library wherein each variant nucleic acid is 600 to 3000 bases in length. Further provided herein is a nucleic acid library wherein each variant nucleic acid is attached to a vector sequence. Further provided herein is a nucleic acid library wherein the vector sequence is a viral vector sequence.

Provided herein is a method for nucleic acid synthesis, the method comprising: providing predetermined sequences encoding for a plurality of non-identical oligonucleotides, wherein each of the non-identical oligonucleotides is at least 20 bases in length, and wherein the plurality of non-identical oligonucleotides encodes for up to 19 variants for each of at least 2 codons compared to at least one reference sequence, wherein the at least one reference sequence encodes for a region of an antigen recognition domain, a hinge domain, a transmembrane domain, or an intracellular domain of a chimeric antigen receptor; providing a structure having a surface, wherein the surface comprises clusters of loci for oligonucleotide extension, each cluster comprising 50 to 500 loci; synthesizing the plurality of non-identical oligonucleotides, wherein each of the non-identical oligonucleotides extends from a separate locus; and performing an amplification reaction to assemble a library of variant nucleic acids, wherein the amplification reaction comprises mixing the plurality of non-identical oligonucleotides from a single cluster with a DNA polymerase and the at least one reference sequence. Further provided herein is a method wherein each cluster further comprises additional oligonucleotides, and wherein the plurality of non-identical oligonucleotides and the additional oligonucleotides within said cluster collectively encode for a single gene and variants thereof. Further provided herein is a method wherein the surface of the structure comprises at least 6000 of the clusters. Further provided herein is a method wherein at least 80% of the variant nucleic acids have no errors compared to the predetermined sequences without correcting errors. Further provided herein is a method wherein at least 90% of the variant nucleic acids have no errors compared to the predetermined sequences without correcting errors. Further provided herein is a method wherein a replicate of each non-identical oligonucleotide extends from the surface at up to 5 loci. Further provided herein is a method wherein a replicate of each non-identical oligonucleotide extends from the surface at up to 3 loci. Further provided herein is a method wherein the plurality of non-identical oligonucleotides encodes for up to 19 variants for each of at least 3 codons compared to at least one reference sequence. Further provided herein is a method further comprising expressing the variant nucleic acid library, wherein expression of the variant nucleic acid library provides for a variant protein having improved affinity, improved gene expression, improved avidity, improved stability, or improved target specificity compared to the expression product of the reference sequence.

Provided herein is a method for nucleic acid synthesis, the method comprising: providing predetermined sequences encoding for a plurality of non-identical oligonucleotides, wherein each of the non-identical oligonucleotides is at least 20 bases in length, and wherein the plurality of non-identical oligonucleotides encodes for up to 19 variants for each of at least 2 codons compared to at least one reference sequence, wherein the at least one reference sequence encodes for an epitope to a chimeric antigen receptor; providing a structure having a surface, wherein the surface comprises clusters of loci for oligonucleotide extension, each cluster comprising 50 to 500 loci; synthesizing the plurality of non-identical oligonucleotides, wherein each of the non-identical oligonucleotides extends from a separate locus; and performing an amplification reaction to assemble a library of variant nucleic acids, wherein the amplification reaction comprises mixing the plurality of non-identical oligonucleotides from a single cluster with a DNA polymerase and the at least one reference sequence. Further provided herein is a method wherein the surface of the structure comprises at least 6000 of the clusters. Further provided herein is a method wherein at least about 80% of the variant nucleic acids have no errors compared to the predetermined sequences without correcting errors. Further provided herein is a method wherein at least about 90% of the variant nucleic acids have no errors compared to the predetermined sequences without correcting errors. Further provided herein is a method wherein a replicate of each non-identical oligonucleotide extends from the surface at up to 5 loci. Further provided herein is a method wherein a replicate of each non-identical oligonucleotide extends from the surface at up to 3 loci. Further provided herein is a method wherein the plurality of non-identical oligonucleotides encodes for up to 19 variants for each of at least 3 codons compared to at least one reference sequence. Further provided herein is a method further comprising expressing the variant nucleic acid library, wherein expression of the variant nucleic acid library provides for a variant peptide having improved affinity, improved gene expression, improved avidity, improved stability, or improved target specificity compared to the expression product of the reference sequence. Further provided herein is a method wherein the at least one reference sequence encodes for the epitope to a chimeric antigen receptor and also for an epitope to a surface protein expressed by a non-lymphoid cell.

Provided herein is a method for nucleic acid synthesis of nucleic acid libraries for optimization assays, the method comprising: providing a first set of predetermined sequences encoding for a first plurality of non-identical oligonucleotides, wherein each of the non-identical oligonucleotides is at least 20 bases in length, and wherein the first plurality of non-identical oligonucleotides encodes for up to 19 variants for each of at least 3 codons compared to at least one reference sequence, wherein the at least one reference sequence encodes for a region of an antigen recognition domain, a hinge domain, a transmembrane domain, or an intracellular domain of a chimeric antigen receptor; providing a second set of predetermined sequences encoding for a second plurality of non-identical oligonucleotides, wherein each of the second non-identical oligonucleotides is at least 20 bases in length, and wherein the second plurality of non-identical oligonucleotides encodes for up to 19 variants for each of at least 3 codons compared to at least one reference sequence, wherein the at least one reference sequence encodes for an epitope to the chimeric antigen receptor; providing a structure having a surface, wherein the surface comprises clusters of loci for oligonucleotide extension, each cluster comprising 50 to 500 loci; synthesizing both the first plurality of non-identical oligonucleotides and the second plurality of non-identical oligonucleotides, wherein each non-identical oligonucleotides extends from a separate locus; and performing an amplification reaction to assemble a first library of nucleic acids, wherein the amplification reaction comprises mixing the first plurality of non-identical oligonucleotides from a single cluster with a DNA polymerase and the at least one reference sequence; performing an amplification reaction to assemble a second library of variant nucleic acids, wherein the amplification reaction comprises mixing the second plurality of non-identical oligonucleotides from a single cluster with a DNA polymerase and the at least one reference sequence. Further provided herein is a method further comprising screening purified protein expression products of the second library of variant nucleic acids against a library of cells expressing the first library of variant nucleic acids, wherein the library of cells comprises populations of cells, each population of cells expressing a different protein expression product encoded by the first library of variant nucleic acids. Further provided herein is a method wherein the at least one reference sequence for an epitope to the chimeric antigen receptor also encodes for an epitope to a surface protein expressed by a non-lymphoid cell.

BRIEF DESCRIPTION OF THE DRAWINGS

FIGS. 1A-1D depict a process workflow for the synthesis of variant biological molecules incorporating a PCR mutagenesis step.

FIGS. 2A-2D depict a process workflow for the generation of a nucleic acid comprising a nucleic acid sequence which differs from a reference nucleic acid sequence at a single predetermined codon site.

FIGS. 3A-3F depict an alternative workflow for the generation of a set of nucleic acid variants from a template nucleic acid, with each variant comprising a different nucleic acid sequence at a single codon position. Each variant nucleic acid encodes for a different amino acid at their single codon position, the different codons represented by X, Y, and Z.

FIG. 5A discloses SEQ ID NO: 42 and FIG. 5B discloses SEQ ID NOS 43-49, respectively, in order of appearance.

FIGS. 6A-6B depict a reference amino acid sequence (FIG. 6A) and a library of variant amino acid sequences (FIG. 6B), each variant comprising two sites of single position variants. Each variant is indicated by differently patterned circles. The reference amino acid sequence and variant sequences are encoded by nucleic acids and variants thereof generated by processes described herein.

DETAILED DESCRIPTION

Figure 3D:
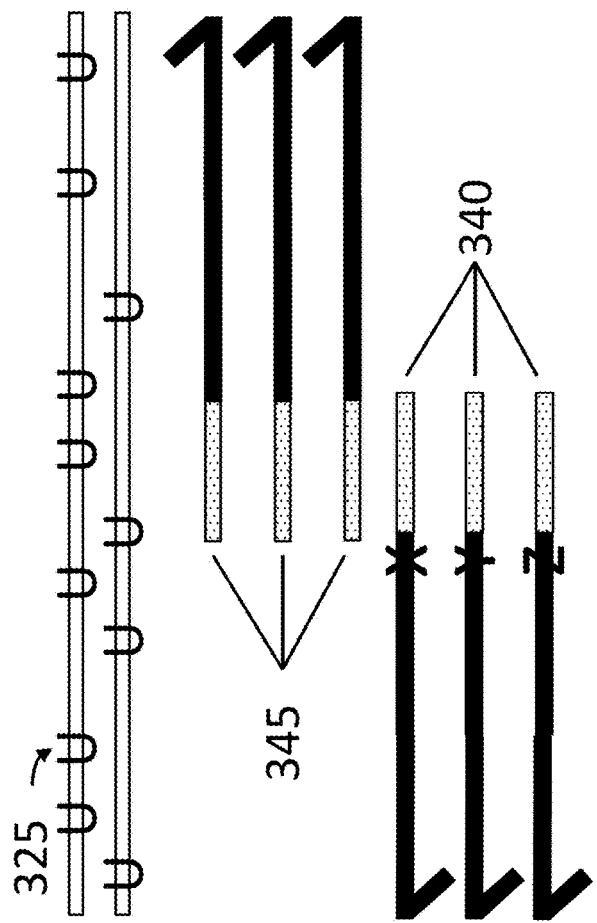
Figure 3E:
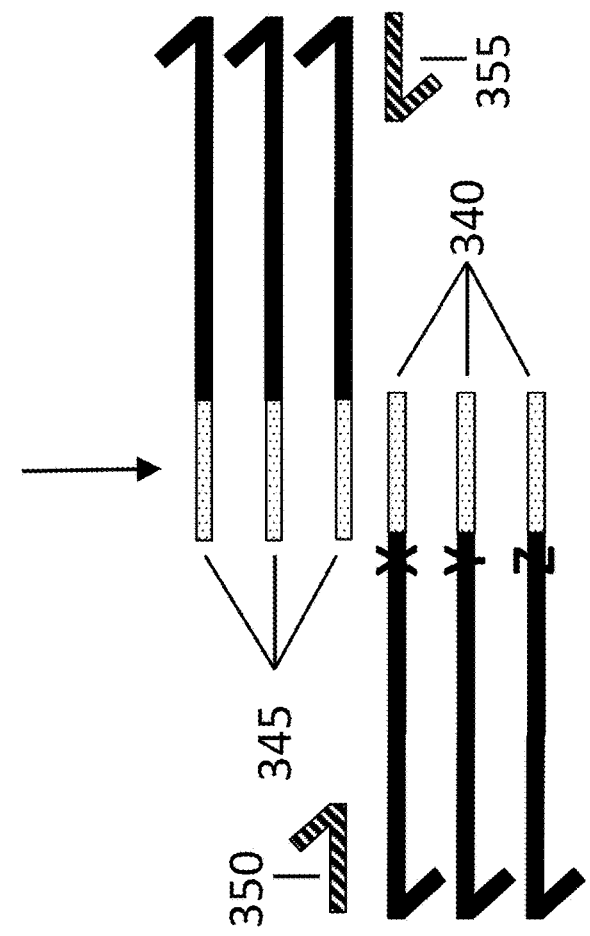
Figure 3F:
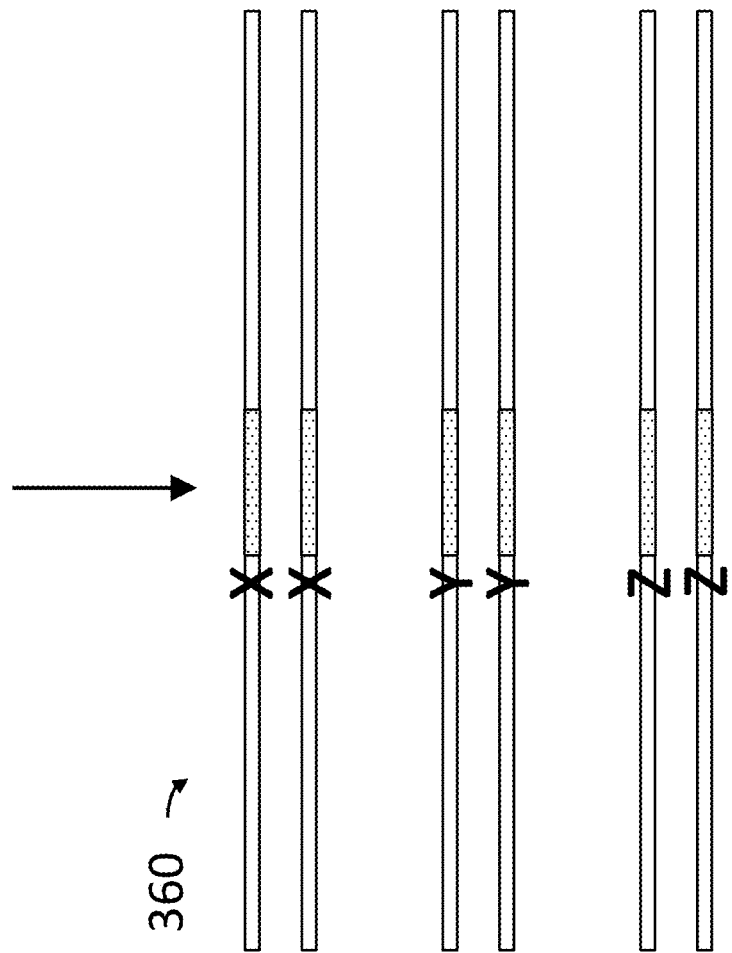

The present disclosure employs, unless otherwise indicated, conventional molecular biology techniques, which are within the skill of the art. Unless defined otherwise, all technical and scientific terms used herein have the same meaning as is commonly understood by one of ordinary skill in the art.

Definitions

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The term "nucleic acid" encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids.

As used herein, the terms "preselected sequence," "predefined sequence" or "predetermined sequence" are used interchangeably. The terms mean that the sequence of the polymer is known and chosen before synthesis or assembly of the polymer. In particular, various aspects of the invention are described herein primarily with regard to the preparation of nucleic acids molecules, the sequence of the oligonucleotide or polynucleotide being known and chosen before the synthesis or assembly of the nucleic acid molecules.

Provided herein are methods and compositions for production of synthetic (i.e. de novo synthesized or chemically synthesized) polynucleotides. The term oligonucleotide, oligo, oligonucleic acid, and polynucleotide are defined to be synonymous throughout. Libraries of synthesized polynucleotides described herein may comprise a plurality of polynucleotides collectively encoding for one or more genes or gene fragments. In some instances, the polynucleotide library comprises coding or non-coding sequences. In some instances, the polynucleotide library encodes for a plurality of cDNA sequences. Reference gene sequences from which the cDNA sequences are based may contain introns, whereas cDNA sequences exclude introns. Polynucleotides described herein may encode for genes or gene fragments from an organism. Exemplary organisms include, without limitation, prokaryotes (e.g., bacteria) and eukaryotes (e.g., mice, rabbits, humans, and non-human primates). In some instances, the polynucleotide library comprises one or more polynucleotides, each of the one or more polynucleotides encoding sequences for multiple exons. Each polynucleotide within a library described herein may encode a different sequence, i.e., non-identical sequence. In some instances, each polynucleotide within a library described herein comprises at least one portion that is complementary to a sequence of another polynucleotide within the library. Polynucleotide sequences described herein may, unless stated otherwise, comprise DNA or RNA.

Provided herein are methods and compositions for production of synthetic (i.e. de novo synthesized) genes. Libraries comprising synthetic genes may be constructed by a variety of methods described in further detail elsewhere herein, such as PCA, non-PCA gene assembly methods or hierarchical gene assembly, combining ("stitching") two or more double-stranded oligonucleotides to produce larger DNA units (i.e., a chassis). Libraries of large constructs may involve oligonucleotides that are at least 1, 1.5, 2, 3, 4, 5, 6, 7, 8, 9, 10, 15, 20, 30, 40, 50, 60, 70, 80, 90, 100, 125, 150, 175, 200, 250, 300, 400, 500 kb long or longer. The large constructs may be bounded by an independently selected upper limit of about 5000, 10000, 20000 or 50000 base pairs. The synthesis of any number of polypeptide-segment encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. cDNA encoding for a gene or gene fragment referred to herein, may comprise at least one region encoding for exon sequence(s) without an intervening intron sequence found in the corresponding genomic sequence. Alternatively, the corresponding genomic sequence to a cDNA may lack an intron sequence in the first place.

Chimeric Antigen Receptor

Figures 10A, 10B, 10C:
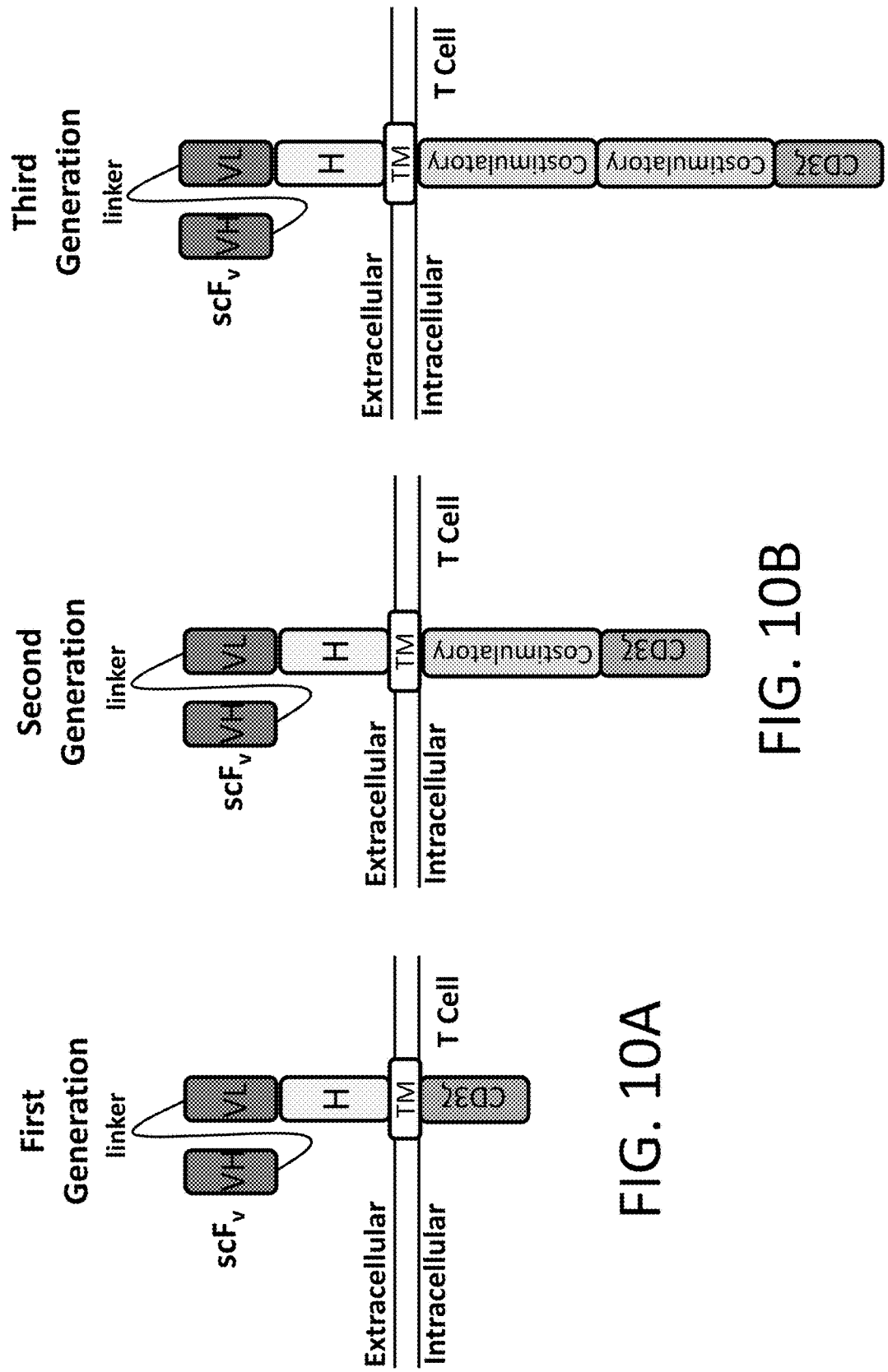
FIGS. 10A-10C illustrate generations of chimeric antigen receptors (CARs). CARs comprise an extracellular single chain variable fragment (scFv), a hinge domain (H), a transmembrane domain (TM), and an intracellular domain. An intracellular domain of a first generation CAR comprises CD3ζ alone (FIG. 10A). An intracellular domain of a second generation CAR comprises a costimulatory domain and CD3ζ (FIG. 10B). An intracellular domain of a third generation CAR comprises two costimulatory domains and CD3ζ (FIG. 10C).
Figure 10E:
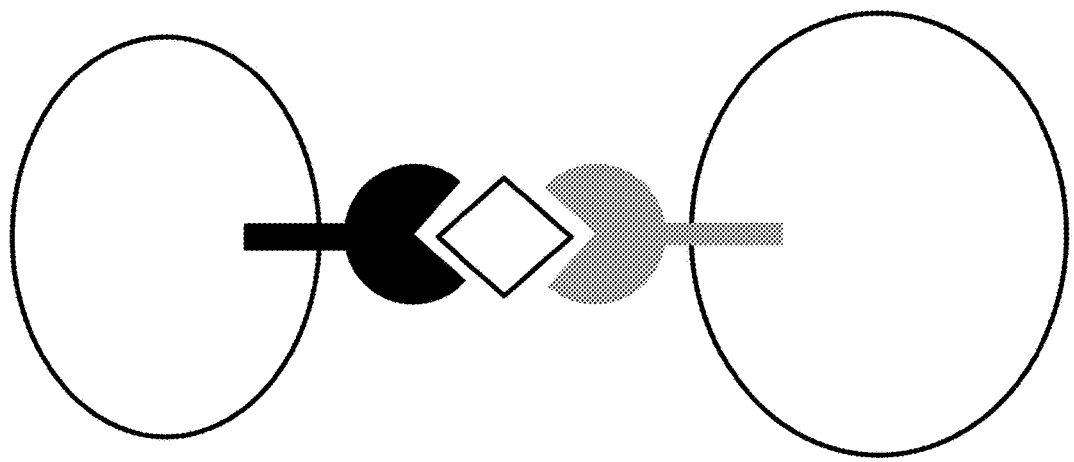
In FIGS. 10D-10E, various CAR binding arrangements are illustrated.
Figure 10D:
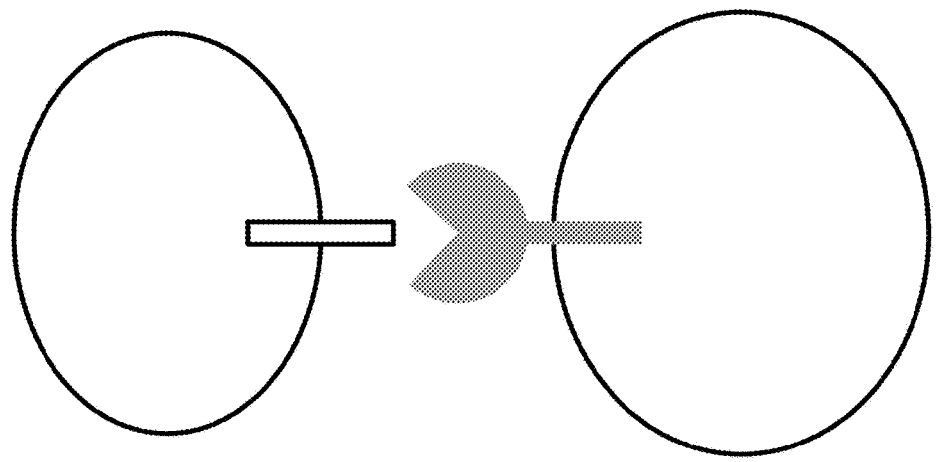

Chimeric antigen receptors (CARs) are generally engineered receptors that recognize a particular antigen such as an antigen whose epitope is unique to cancer cells. Referring to FIGS. 10A-10C, CARs comprise an antigen recognition domain derived from a single chain antibody (scFv), a hinge domain (H) or spacer, a transmembrane domain (TM) that anchors the CAR to the plasma membrane, and an intracellular domain that mediates T cell activation. An intracellular domain of a first generation CAR comprises CD3ζ (FIG. 10A). An intracellular domain of a second generation CAR comprises a costimulatory domain and CD3ζ (FIG. 10B). An intracellular domain of a third generation CAR comprises two costimulatory domains and CD3ζ (FIG. 10C). Exemplary CAR binding schematics are depicted in FIGS. 10D-10E. The CAR may be expressed in a lymphoid cell, e.g., a T cell, and an epitope to the CAR may be expressed in a non-lymphoid cell, or in an in vitro matrix, such as a bead, gel or column. See e.g., FIG. 10D. In some arrangements, the CAR is capable of binding to an epitope of a "linker" protein or peptide, which is able to also serve as an epitope to a surface protein of another surface, e.g., a cell, bead, gel or column. See e.g., FIG. 10E.

Engineering Variance in Chimeric Antigen Receptor

Provided herein are methods for synthesis of variant nucleic acid libraries, wherein each variant nucleic acid encodes for a sequence that is varied in comparison to a reference domain within a CAR. For example, the varied sequence is a nucleic acid sequence that encodes for an antigen recognition domain, a hinge domain, a transmembrane domain, or an intracellular domain. In some instances, the intracellular domain comprises a signaling domain. In some instances, the intracellular domain further comprises a costimulatory domain. In some instances, the variant nucleic acid libraries comprise variant sequences that encode for all domains of a CAR. The resulting nucleic acid library may be an oligonucleotide library, gene fragment library, or gene library. In some instances, the nucleic acid library is expressed in cells to generate a variant protein library.

Variant nucleic acid libraries generated by methods disclosed herein may encode for an antigen recognition domain. An antigen recognition domain may comprise a single chain variable fragment (scFv). In some instances, an antigen recognition domain comprises F(ab')$_2$, Fab', Fab, or Fv. Variant nucleic acid libraries that encode for antigen recognition domains may be designed and synthesized for a particular tumor antigen. Exemplary tumor antigens include, but are not limited to, α-Folate receptor, BCMA, CAIX, CD123, CD138, CD171, CD19, CD20, CD22, CD30, CD33, CD44, CD44v7/8, CEA, cMET, DNAM-1, EDB-F, EGFR, EGFRvIII, EGP-2, EGP-40, EpCAM, FAP, Folate-binding Protein, GD2, GD3, glypican-3, h5T4, HER2, HERS, IL-13, IL-13R-a2, kappa light chain, KDR, Lewis Y, LMP-1, MAGE-A1, mesothelin, MUC-1, MUC-16, PSCA, PSMA, ROR1, TAG-72, VEGFR, and VEGFR2. In some instances, about 25, 50, 100, 250, 500, 1000, or more than 1000 common coding gene sequences of an antigen recognition domain is selected for variation. Variation may include designing of at least 25, 50, 100, 250, 500, 1000, 2000, 5000, 10000, 20000, 50000, 100000, or more than 100000 variants for each of the common coding gene sequences selected.

The hinge domain and transmembrane domain may connect the antigen recognition domain to the intracellular domains and anchor the CAR in the T cell membrane. In some instances, variant nucleic acid libraries are generated that encode for the hinge domain Exemplary hinge domains are immunoglobulin (e.g., IgG1, IgG2, IgG3, IgG4, IgA1, IgA2, IgM, IgD or IgE), CH2CH3 region of immunoglobulin and optionally portions of CD3, and CD8α. In some cases, variant nucleic acid libraries are generated that encode for the transmembrane domain.

Variant nucleic acid libraries generated by methods disclosed herein may comprise sequences that are varied to an intracellular domain. In some instances, the intracellular domain comprises a costimulatory domain. In some instances, variant nucleic acid libraries comprise sequences that are varied to a reference costimulatory domain of a CAR. Exemplary costimulatory domains include, but not limited to, CD8, CD27, CD28, 4-1BB (CD137), ICOS, DAP10, OX40 (CD134) or fragments or combinations thereof. In some instances, about 100, 250, 500, 1000, or more than 1000 common coding gene sequences of a costimulatory domain is selected for variation. Variation includes designing of at least about 500, 1000, 2000, 5000, 10000, 20000, 50000, 100000, or more than 100000 variants for each of the common coding gene sequences selected. Exemplary costimulatory domain sequences are shown in Table 1.

TABLE 1

Costimulatory Domains

| Name | SEQ ID NO | Accession Number | Nucleic Acid Sequence |
|---|---|---|---|
| Human ICOS | 24 | AAL40933.1 | ATGAAGTCAGGCCTCTGGTATTTCTTTCTCTTCTGC TTGCGCATTAAAGTTTTAACAGGAGAAATCAATGG TTCTGCCAATTATGAGATGTTTATATTTCACAACG GAGGTGTACAAATTTTATGCAAATATCCTGACATT GTCCAGCAATTTAAAATGCAGTTGCTGAAAGGGG GGCAAATACTCTGCGATCTCACTAAGACAAAAGG AAGTGGAAACACAGTGTCCATTAAGAGTCTGAAA TTCTGCCATTCTCAGTTATCCAACAACAGTGTCTCT TTTTTTCTATACAACTTGGACCATTCTCATGCCAAC TATTACTTCTGCAACCTATCAATTTTTGATCCTCCT CCTTTTAAAGTAACTCTTACAGGAGGATATTTGCA TATTTATGAATCACAACTTTGTTGCCAGCTGAAGT TCTGGTTACCCATAGGATGTGCAGCCTTTGTTGTA GTCTGCATTTTGGGATGCATACTTATTTGTTGGCTT ACAAAAAAGAAGTATTCATCCAGTGTGCACGACC |

TABLE 1-continued

Costimulatory Domains

| Name | SEQ ID NO | Accession Number | Nucleic Acid Sequence |
|---|---|---|---|
| | | | CTAACGGTGAATACATGTTCATGAGAGCAGTGAA CACAGCCAAAAAATCTAGACTCACAGATGTGACC CTATAA |
| Human OX40 | 25 | BAG60249.1. | ATGGTATCACATCGGTATCCTCGAATTCAAAGTAT CAAAGTACAATTTACCGAATATAAGAAGGAGAAA GGTTTCATCCTCACTTCCCAAAAGGAGGATGAAAT CATGAAGGTGCAGAACAACTCAGTCATCATCAAC TGTGATGGGTTTTATCTCATCTCCCTGAAGGGCTA CTTCTCCCAGGAAGTCAACATTAGCCTTCATTACC AGAAGGATGAGGAGCCCCTCTTCCAACTGAAGAA GGTCAGGTCTGTCAACTCCTTGATGGTGGCCTCTC TGACTTACAAAGACAAAGTCTACTTGAATGTGACC ACTGACAATACCTCCCTGGATGACTTCCATGTGAA TGGCGGAGAACTGATTCTTATCCATCAAAATCCTG GTGAATTCTGTGTCCTTTGA |
| Human 4-1BB (CD137) | 26 | AAR05440.1 | ATGGGAAACAGCTGTTACAACATAGTAGCCACTCT GTTGCTGGTCCTCAACTTTGAGAGGACAAGATCAT TGCAGGATCCTTGTAGTAACTGCCCAGCTGGTACA TTCTGTGATAATAACAGGAATCAGATTTGCAGTCC CTGTCCTCCAAATAGTTTCTCCAGCGCAGGTGGAC AAAGGACCTGTGACATATGCAGGCAGTGTAAAGG TGTTTTCAGGACCAGGAAGGAGTGTTCCTCCACCA GCAATGCAGAGTGTGACTGCACTCCAGGGTTTCAC TGCCTGGGGGCAGGATGCAGCATGTGTGAACAGG ATTGTAAACAAGGTCAAGAACTGACAAAAAAAGG TTGTAAAGACTGTTGCTTTGGGACATTTAACGATC AGAAACGTGGCATCTGTCGACCCTGGACAAACTG TTCTTTGGATGGAAAGTCTGTGCTTGTGAATGGGA CGAAGGAGAGGGACGTGGTCTGTGGACCATCTCC AGCCGACCTCTCTCGGGAGCATCCTCTGTGACCC CGCCTGCCCCTGCGAGAGAGCCAGGACACTCTCC GCAGATCATCTCCTTCTTTCTTGCGCTGACGTCGA CTGCGTTGCTCTTCCTGCTGTTCTTCCTCACGCTCC GTTTCTCTGTTGTTAAACGGGGCAGAAAGAAACTC CTGTATATATTCAAACAACCATTTATGAGACCAGT ACAAACTACTCAAGAGGAAGATGGCTGTAGCTGC CGATTTCCAGAAGAAGAAGAAGGAGGATGTGAAC TGTGA |
| Human CD27 | 27 | AAR84239.1 | ATGGCACGGCCACATCCCTGGTGGCTGTGCGTTCT GGGGACCCTGGTGGGGCTCTCAGCTACTCCAGCCC CCAAGAGCTGCCCAGAGAGGCACTACTGGGCTCA GGGAAAGCTGTGCTGCCAGATGTGTGAGCCAGGA ACATTCCTCGTGAAGGACTGTGACCAGCATAGAA AGGCTGCTCAGTGTGATCCTTGCATACCGGGGGTC TCCTTCTCTCCTGACCACCACACCCGGCCCCACTG TGAGAGCTGTCGGCACTGTAACTCTGGTCTTCTCG TTCGCAACTGCACCATCACTGCCAATGCTGAGTGT GCCTGTCGCAATGGCTGGCAGTGCAGGGACAAGG AGTGCACCGAGTGTGATCCTCTTCCAAACCCTTCG CTGACCGCTCGGTCGTCTCAGGCCCTGAGCCCACA CCCTCAGCCCACCCACTTACCTTATGTCAGTGAGA TGCTGGAGGCCAGGACAGCTGGGCACATGCAGAC TCTGGCTGACTTCAGGCAGCTGCCTGCCCGGACTC TCTCTACCCACTGGCCACCCCAAAGATCCCTGTGC AGCTCCGATTTATTCGCATCCTTGTGATCTTCTCT GGAATGTTCCTGGTTTTCACCCTGGCCGGGGCCCT GTTCCTCCATCAACGAAGGAAATATAGATCAAAC AAAGGAGAAAGTCCTGTGGAGCCTGCAGAGCCTT GTCGTTACAGCTGCCCCAGGGAGGAGGGGCAG CACCATCCCCATCCAGGAGGATTACCGAAAACCG AGCCTGCCTGCTCCCCCTGA |
| Human CD8 alpha | 28 | AAB04637.1 | ATGGCCTTACCAGTGACCGCCTTGCTCCTGCCGCT GGCCTTGCTGCTCCACGCCGCCAGGCCGAGCCAGT TCCGGGTGTCGCCGCTGGATCGGACCTGGAACCTG GGCGAGACAGTGGAGCTGAAGTGCCAGGTGCTGC TGTCCAACCCGACGTCGGGCTGCTCGTGGCTCTTC CAGCCGCGCGGCGCCGCCGCCAGTCCCACCTTCCT CCTATACCTCTCCCAAAACAAGCCCAAGGCGGCC GAGGGGCTGGACACCCAGCGGTTCTCGGGCAAGA GGTTGGGGGACACCTTCGTCCTCACCCTGAGCGAC TTCCGCCGAGAGAACGAGGGCTACTATTTCTGCTC |

TABLE 1-continued

Costimulatory Domains

| Name | SEQ ID NO | Accession Number | Nucleic Acid Sequence |
|---|---|---|---|
| | | | GGCCCTGAGCAACTCCATCATGTACTTCAGCCACT<br>TCGTGCCGGTCTTCCTGCCAGCGAAGCCCACCACG<br>ACGCCAGCGCCGCGACCACCAACACCGGCGCCCA<br>CCATCGCGTCGCAGCCCCTGTCCCTGCGCCCAGAG<br>GCGTGCCGGCCAGCGGCGGGGGCGCAGTGCACA<br>CGAGGGGGCTGGACTTCGCCTGTGATATCTACATC<br>TGGGCGCCCTTGGCCGGGACTTGTGGGGTCCTTCT<br>CCTGTCACTGGTTATCACCCTTTACTGCAACCACA<br>GGAACCGAAGACGTGTTTGCAAATGTCCCCGGCCT<br>GTGGTCAAATCGGGAGACAAGCCCAGCCTTTCGG<br>CGAGATACGTCTAA |
| Human DAP10 | 29 | AAD47911.1 | ATGATCCATCTGGGTCACATCCTCTTCCTGCTTTTG<br>CTCCCAGTGGCTGCAGCTCAGACGACTCCAGGAG<br>AGAGATCATCACTCCCTGCCTTTTACCCTGGCACT<br>TCAGGCTCTTGTTCCGGATGTGGGTCCCTCTCTCTG<br>CCGCTCCTGGCAGGCCTCGTGGCTGCTGATGCGGT<br>GGCATCGCTGCTCATCGTGGGGCGGTGTTCCTGT<br>GCGCACGCCCACGCCGCAGCCCCGCCCAAGAAGA<br>TGGCAAAGTCTACATCAACATGCCAGGCAGGGGC<br>TGA |

Variant nucleic acid libraries as described herein may comprise variants of the intracellular domain. In some instances, the intracellular domain comprises a signaling domain. In some instances, variant nucleic acid libraries generated by methods disclosed herein comprise sequences that are varied when compared to the signaling domain. In some instances, the signaling domain comprises an immunoreceptor tyrosine-based activation motif (ITAM). In some instances, the signaling domain comprises a domain derived from TCR zeta, FcR gamma, FcR beta, CD3 gamma, CD3 delta, CD3 epsilon, CD5, CD22, CD79a, CD79b or CD66d. In some cases, the signaling domain for T-cell activation comprises a domain derived from CD3ζ. In some instances, about 100, 250, 500, 1000, or more than 1000 common coding gene sequences of a signaling domain for T cell activation is selected for variation. Variation includes designing of at least about 500, 1000, 2000, 5000, 10000, 20000, 50000, 100000, or more than 100000 variants for each of the common coding gene sequences selected. Exemplary signaling domain sequences are shown in Table 2.

TABLE 2

Signaling Domain Sequences

| Name | SEQ ID NO | Accession Number | Nucleic Acid Sequence |
|---|---|---|---|
| Human CD3 gamma | 30 | AAI13831.1 | ATGGAACAGGGGAAGGGCCTGGCTGTCCTCATCCTGGCT<br>ATCATTCTTCTTCAAGGTACTTTGGCCCAGTCAATCAAAG<br>GAAACCACTTGGTTAAGGTGTATGACTATCAAGAAGATG<br>GTTCGGTACTTCTGACTTGTGATGCAGAAGCCAAAATAT<br>CACATGGTTTAAAGATGGGAAGATGATCGGCTTCCTAAC<br>TGAAGATAAAAAAAAATGGAATCTGGGAAGTAATGCCAA<br>GGACCCTCGAGGGATGTATCAGTGTAAAGGATCACAGAA<br>CAAGTCAAAACCACTCCAAGTGTATTACAGAATGTGTCA<br>GAACTGCATTGAACTAAATGCAGCCACCATATCTGGCTTT<br>CTCTTTGCTGAAATCGTCAGCATTTTCGTCCTTGCTGTTGG<br>GGTCTACTTCATTGCTGGACAGGATGGAGTTCGCCAGTCG<br>AGAGCTTCAGACAAGCAGACTCTGTTGCCCAATGACCAG<br>CTCTACCAGCCCCTCAAGGATCGAGAAGATGACCAGTAC<br>AGCCACCTTCAAGGAAACCAGTTGAGGAGGAATTGA |
| Human CD3 epsilon | 31 | EAW67364.1 | ATGCAGTCGGGCACTCACTGGAGAGTTCTGGGCCTCTGCC<br>TCTTATCAGTTGGCGTTTGGGGGCAAGATGGTAATGAAG<br>AAATGGGTGGTATTACACAGACACCATATAAAGTCTCCA<br>TCTCTGGAACCACAGTAATATTGACATGCCCTCAGTATCC<br>TGGATCTGAAATACTATGGCAACACAATGATAAAAACAT<br>AGGCGGTGATGAGGATGATAAAAACATAGGCAGTGATGA<br>GGATCACCTGTCACTGAAGGAATTTTCAGAATTGGAGCA<br>AAGTGGTTATTATGTCTGCTACCCCAGAGGAAGCAAACC<br>AGAAGATGCGAACTTTTATCTCTACCTGAGGGCAAGAGT<br>GTGTGAGAACTGCATGGAGATGGATGTGATGTCGGTGGC<br>CACAATTGTCATAGTGGACATCTGCATCACTGGGGGCTTG<br>CTGCTGCTGGTTTACTACTGGAGCAAGAATAGAAAGGCC<br>AAGGCCAAGCCTGTGACACGAGGAGCGGGTGCTGGCGGC |

TABLE 2-continued

Signaling Domain Sequences

| Name | SEQ ID NO | Accession Number | Nucleic Acid Sequence |
|---|---|---|---|
| | | | AGGCAAAGGGGACAAAACAAGGAGAGGCCACCACCTGT<br>TCCCAACCCAGACTATGAGCCCATCCGGAAAGGCCAGCG<br>GGACCTGTATTCTGGCCTGAATCAGAGACGCATCTGA |
| Human CD79 alpha | 32 | AAB20812.1 | ATGCCTGGGGGTCCAGGAGTCCTCCAAGCTCTGCCTGCCA<br>CCATCTTCCTCCTCTTCCTGCTGTCTGCTGTCTACCTGGGC<br>CCTGGGTGCCAGGCCCTGTGGATGCACAAGGTCCCAGCA<br>TCATTGATGGTGAGCCTGGGGAAGACGCCCACTTCCAA<br>TGCCCGCACAATAGCAGCAACAACGCCAACGTCACCTGG<br>TGGCGCGTCCTCCATGGCAACTACACGTGGCCCCCTGAGT<br>TCTTGGGCCCGGGCGAGGACCCCAATGGTACGCTGATCA<br>TCCAGAATGTGAACAAGAGCCATGGGGGCATATACGTGT<br>GCCGGGTCCAGGAGGGCAACGAGTCATACCAGCAGTCCT<br>GCGGCACCTACCTCCGCGTGCGCCAGCCGCCCCCCAGGC<br>CCTTCCTGGACATGGGGGAGGGCACCAAGAACCGAATCA<br>TCACAGCCGAGGGGATCATCCTCCTGTTCTGCGCGGTGGT<br>GCCTGGGACGCTGCTGCTGTTCAGGAAACGATGGCAGAA<br>CGAGAAGCTCGGGTTGGATGCCGGGGATGAATATGAAGA<br>TGAAAACCTTTATGAAGGCCTGAACCTGGACGACTGCTC<br>CATGTATGAGGACATCTCCCGGGGCCTCCAGGGCACCTA<br>CCAGGATGTGGGCAGCCTCAACATAGGAGATGTCCAGCT<br>GGAGAAGCCGTGA |
| Human CD79 beta | 33 | NM_000626.3 | AGGGGACAGGCTGCAGCCGGTGCAGTTACACGTTTTCCT<br>CCAAGGAGCCTCGGACGTTGTCACGGGTTTGGGGTCGGG<br>GACAGAGCGGTGACCATGGCCAGGCTGGCGTTGTCTCCT<br>GTGCCCAGCCACTGGATGGTGGCGTTGCTGCTGCTGCTCT<br>CAGCTGAGCCAGTACCAGCAGCCAGATCGGAGGACCGGT<br>ACCGGAATCCCAAAGGTAGTGCTTGTTCGCGGATCTGGC<br>AGAGCCCACGTTTCATAGCCAGGAAACGGGGCTTCACGG<br>TGAAAATGCACTGCTACATGAACAGCGCCTCCGGCAATG<br>TGAGCTGGCTCTGGAAGCAGGAGATGGACGAGAATCCCC<br>AGCAGCTGAAGCTGGAAAAGGGCCGCATGGAAGAGTCCC<br>AGAACGAATCTCTCGCCACCCTCACCATCCAAGGCATCC<br>GGTTTGAGGACAATGGCATCTACTTCTGTCAGCAGAAGT<br>GCAACAACACCTCGGAGGTCTACCAGGGCTGCGGCACAG<br>AGCTGCGAGTCATGGGATTCAGCACCTTGGCACAGCTGA<br>AGCAGAGGAACACGCTGAAGGATGGTATCATCATGATCC<br>AGACGCTGCTGATCATCCTCTTCATCATCGTGCCTATCTT<br>CCTGCTGCTGGACAAGGATGACAGCAAGGCTGGCATGGA<br>GGAAGATCACACCTACGAGGGCCTGGACATTGACCAGAC<br>AGCCACCTATGAGGACATAGTGACGCTGCGGACAGGGGA<br>AGTGAAGTGGTCTGTAGGTGAGCACCCAGGCCAGGAGTG<br>AGAGCCAGGTCGCCCCATGACCTGGGTGCAGGCTCCCTG<br>GCCTCAGTGACTGCTTCGGAGCTGCCTGGCTCATGGCCCA<br>ACCCCTTTCCTGGACCCCCCAGCTGGCCTCTGAAGCTGGC<br>CCACCAGAGCTGCCATTTGTCTCCAGCCCCTGGTCCCCAG<br>CTCTTGCCAAAGGGCCTGGAGTAGAAGGACAACAGGGCA<br>GCAACTTGGAGGGAGTTCTCTGGGGATGGACGGGACCCA<br>GCCTTCTGGGGGTGCTATGAGGTGATCCGTCCCCACACAT<br>GGGATGGGGAGGCAGAGACTGGTCCAGAGCCCGCAAA<br>TGGACTCGGAGCCGAGGGCCTCCCAGCAGAGCTTGGGAA<br>GGGCCATGGACCCAACTGGGCCCCAGAAGAGCCACAGGA<br>ACATCATTCCTCTCCCGCAACCACTCCCACCCCAGGGAGG<br>CCCTGGCCTCCAGTGCCTTCCCCCGTGGAATAAACGGTGT<br>GTCCTGAGAAACCACACAAAAAAAA |
| Human CD3 zeta | 34 | AAY57330.1 | ATGAAGTGGAAGGCGCTTTTCACCGCGGCCATCCTGCAG<br>GCACAGTTGCCGATTACAGAGGCACAGAGCTTTGGCCTG<br>CTGGATCCCAAACTCTGCTACCTGCTGGATGGAATCCTCT<br>TCATCTATGGTGTCATTCTCACTGCCTTGTTCCTGAGAGT<br>GAAGTTCAGCAGGAGCGCAGACGCCCCCGCGTACCAGCA<br>GGGCCAGAACCAGCTCTATAACGAGCTCAATCTAGGACG<br>AAGAGAGGAGTACGATGTTTTGGACAAGAGACGTGGCCG<br>GGACCCTGAGATGGGGGGAAAGCCGCAGAGAAGGAAGA<br>ACCCTCAGGAAGGCCTGTACAATGAACTGCAGAAAGATA<br>AGATGGCGGAGGCCTACAGTGAGATTGGGATGAAAGGCG<br>AGCGCCGGAGGGGCAAGGGGCACGATGGCCTTTACCAGG<br>GTCTCAGTACAGCCACCAAGGACACCTACGACGCCCTTC<br>ACATGCAGGCCCTGCCCCCTCGCTAA |

Methods provided herein for the synthesis of a variant nucleic acid library that is varied in comparison to a reference domain within a CAR may include: de novo synthesis of a variant library of primer oligonucleotides followed by PCR mutagenesis, or de novo synthesis of multiple fragments of the variant version for annealing and assembly including polymerase chain assembly.

A nucleic acid library as described herein may comprise a plurality of nucleic acids that are varied in comparison to a reference domain within a reference CAR, and variation is generated by de novo synthesis of a variant library of primer oligonucleotides followed by PCR mutagenesis. In some instances, oligonucleotides are synthesized on a surface, wherein each oligonucleotide encodes for a predetermined sequence. In some instances, the predetermined sequence is a predetermined variant of a reference nucleic acid sequence that encodes for an antigen recognition domain, a hinge domain, a transmembrane domain, or an intracellular domain of a CAR. In some instances, oligonucleotide primers are de novo synthesized for use in a series of PCR reactions to generate a library of oligonucleotide variants of a reference nucleic acid sequence that encodes for an antigen recognition domain, a hinge domain, a transmembrane domain, or an intracellular domain of a CAR. In some instances, the oligonucleotide primers are used for amplification from a reference nucleic acid sequence to produce a library of variant nucleic acids encoding for an antigen recognition domain, a hinge domain, a transmembrane domain, or an intracellular domain of a CAR.

In some instances, a variant nucleic acid library varied in comparison to a reference domain within a CAR is generated by de novo synthesis of multiple fragments of the variant version of the common sequence for annealing and assembly including polymerase chain assembly. In some instances, a surface is used for de novo synthesis of multiple fragments of a nucleic acid sequence, wherein at least one of the fragments is synthesized in multiple versions. The nucleic acid sequence may be a variant of a reference nucleic acid sequence that encodes for an antigen recognition domain, a hinge domain, a transmembrane domain, or an intracellular domain of a CAR. In some instances, the fragments are subject to hybridization to generate a CAR variant library. In some instances, the synthesized fragments are amplified and subject to ligation or hybridization to generate a CAR variant library.

In some instances, a CAR variant library comprises nucleic acid sequences that encode for an antigen recognition domain, a hinge domain, a transmembrane domain, or an intracellular domain including a stimulatory domain or a signaling domain of a CAR. In some instances, a CAR variant library comprises nucleic acid sequences that encodes for a single domain of a CAR. In some instances, a CAR variant library comprises nucleic acid sequences that encodes for multiple domains of a CAR. For example, a CAR variant library comprises nucleic acid sequences that encode for all domains of a CAR.

Libraries comprising nucleic acids encoding for variant CARs as described herein comprise various lengths of amino acids when translated. In some instances, the length of each of the amino acid fragments or average length of the amino acid synthesized may be at least or about 15, 20, 25, 30, 35, 40, 45, 50, 55, 60, 65, 70, 75, 80, 85, 90, 95, 100, 105, 110, 115, 120, 125, 130, 135, 140, 145, 150, or more than 150 amino acids. In some instances, the length of the amino acid is in a range of about 15 to 150, 20 to 145, 25 to 140, 30 to 135, 35 to 130, 40 to 125, 45 to 120, 50 to 115, 55 to 110, 60 to 110, 65 to 105, 70 to 100, or 75 to 95 amino acids. In some instances, the length of the amino acid is in a range of about 22 to about 75 amino acids.

A number of variant sequences for the at least one region of the CAR chain for variation are de novo synthesized using methods as described herein. In some instances, a number of variant sequences is de novo synthesized for an antigen recognition domain, a hinge domain, a transmembrane domain, or an intracellular domain of a CAR. In some instances, a number of variant sequences is de novo synthesized for a stimulatory domain or a signaling domain of a CAR. The number of variant sequences may be at least or about 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, or more than 500 sequences. In some instances, the number of variant sequences is at least or about 500, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800, 000, 900,000, 1 million, or more than 1 million sequences. In some instances, the number of variant sequences is in a range of about 10 to 500, 25 to 475, 50 to 450, 75 to 425, 100 to 400, 125 to 375, 150 to 350, 175 to 325, 200 to 300, 225 to 375, 250 to 350, or 275 to 325 sequences.

Provided herein are variant nucleic acids encoding for variant CARs, wherein the variant CARs are antigen specific. In some instances, the antigen is involved in or associated with a disease, disorder, or condition. For example, the antigen is associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In some instances, the antigen is an antigen expressed on a tumor cell. In some instances, an antigen is associated with a pathogen such as a virus or bacterium.

In some instances, the variant CARs recognize antigens that are tissue-restricted. For example, the variant CARs are restricted non-vital cell lineages or tissues. In some instances, the variant CARs recognize antigens from mutated gene products.

Provided herein are variant CAR libraries, wherein the variant CARs encode for variants in an antigen binding interface. In some instances, residues for variation are preselected or predicted residues that contact an antigen. In some instances, the antigen binding interface is the antigen recognition domain. In some instances, residues for variation are preselected or predicted residues located in the binding pocket.

Variant CAR libraries as described herein comprise one or more mutations in a library. In some instances, the CAR variant libraries are single variant libraries comprising variants at a single site across the library. In some instances, the CAR variant libraries are multiple variant libraries comprising variants at a number of sites. In some instances, the number of sites is 2, 3, 4, 5, 6, 7, 8, 9, 10, or more than 10 sites.

Provided here are libraries where one or more preselected codons in a CAR gene or gene fragment encode for variant amino acid residues to generate variation in resulting variant CAR protein libraries. In some instances, up to 10, 20, 30, 40, 50, 60, 70, 80, 90, or 100 amino acid residues are varied. In some instances, up to 30 amino acid residues are varied. In some instances, up to 5 amino acid residues are varied. In some instances, up to 100, 200, 300, 400, 500, 600, 700, 800, 900, 1000, or more than 1000 amino acid residues are varied. In some instances, at least or about 10, 20, 30, 40, 50, 60, 70, 80, 90, or 100 amino acid residues are varied. In some instances, at least or about 100, 200, 300, 400, 500, 600, 700, 800, 900, 1000, or more than 1000 amino acid residues are varied. In some instances, all amino acid residues in a preselected region are varied. In some instances, variant CAR libraries are highly diverse. In some instances, the libraries comprise at least or about $10^{\wedge}6$, $10^{\wedge}8$, $10^{\wedge}9$, $10^{\wedge}10$, $10^{\wedge}12$, or $10^{\wedge}13$ variants. In some instances, the libraries comprise at least or about $10^{\wedge}9$ variants.

Subsequent to synthesis of variant nucleic acid libraries encoding for a reference domain within a CAR, variant nucleic acid libraries may be inserted into a vector sequence. In some instances, the vector sequence is expressed (e.g., by electroporation, transfection, or transduction) in cells and functional consequences are determined. CAR domains that may be varied are an antigen recognition domain, a hinge domain, a transmembrane domain, or an intracellular domain. In some instances, the intracellular domain comprises a signaling domain or a costimulatory domain. In some instances, the variant nucleic acid libraries comprise variant sequences that encode for all domains of a CAR. Functional consequences that may be measured include binding affinity and binding strength. In some instances, variant nucleic acid libraries generated by methods disclosed herein result in increased binding strength of an antigen recognition domain to a tumor antigen associated with a particular cancer of interest. The cancer may be a solid cancer or a hematologic cancer. In some instances, the cancer is bladder cancer, lung cancer, brain cancer, melanoma, breast cancer, Non-Hodgkin lymphoma, cervical cancer, ovarian cancer, colorectal cancer, pancreatic cancer, esophageal cancer, prostate cancer, kidney cancer, skin cancer, leukemia, thyroid cancer, liver cancer, or uterine cancer. Exemplary antigens for use in binding assays include, without limitation, those provided in Table 3.

TABLE 3

Antigens

| Antigen peptide name | Protein Sequence | SEQ ID NO | Disease Target |
|---|---|---|---|
| CD19 | KVSAVTLAY | 35 | B-cell malignancy |
| CD20 | RPKSNIVLL | 36 | B-cell malignancy |
| CEA peptide | IMIGVLVGV | 37 | Metastatic colorectal cancer |
| HER2 | IISAVVGIL | 38 | Breast cancer, lung cancer, prostate cancer, glioma |
| NY-ESO-1 | SLLMWITQV | 39 | Many cancers including melanoma and sarcoma |
| PSMA | KYADKIYSI | 40 | Prostate cancer |

Variant nucleic acid libraries generated using methods described herein may be screened to select a modified CAR domain sequence providing for a protein complex with improved affinity (measure of the strength of interaction between an epitope and an antibody's antigen binding site) for a tumor antigen. Additional functional considerations, such as variant gene expression, avidity, stability, and target cell (i.e. cancer cell) specificity may also be assessed. In some instances, the increased specificity of a CAR provides for reduced cross-reactivity to non-cancer associated antigens compared to a reference non-variant CAR. In some instances, the variant CAR libraries are screened for localization within a cell. In some instances, the variant CAR libraries are screened to identify properly localized variant CARs.

Increased specificity of a variant CAR to a tumor antigen may result in decreased toxicity. Toxicity in some instances that results include cytokine release syndrome (CRS), macrophage activation syndrome (MAS), on-target off-tumor toxicity, autoimmunity, host-graft toxicity, neurotoxicity, and tumor lysis syndrome. Variant nucleic acid libraries encoding for an antigen recognition domain may be inserted into a vector sequence, expressed in cells, and screened for functional consequences such as decreased toxicity. For example, variant nucleic acid libraries are screened for increased cytokine (e.g., interleukin-6 (IL-6), interferon-γ, tumor necrosis factor, IL-2, IL-2-receptor-α, IL-8, and IL-10) release from cells or increased cytokine expression as a measure of CRS.

In some instances, variant nucleic acid libraries generated using methods described herein are screened to select a modified CAR domain sequence providing for improved T cell function or improved T cell activation. In some instances, variant CARs are used to screen T cell pathways affecting cell growth, survival, cellular differentiation, cell death, or intracellular signaling modulation. For example, the serine/threonine kinase Akt has been shown to improve T-cell function and survival resulting in resistance to tumor inhibitory mechanisms. In some cases, variant CARs are used to screen T cell pathways that improve resistance to tumor inhibitory mechanisms. In some instances, variant CARs generated using methods described herein result in enhanced immune response towards a target cell such as a cancer cell. For example, a variant CAR may increase cytotoxic activity of a cytotoxic cell (e.g., a Natural Killer cell or cytotoxic T lymphocyte) towards a target cell such as a cancer cell. In some instances, variant CARs generated using methods described herein result in enhanced immune response towards a target cell such as a cancer cell, thus resulting in increased death of a cancer cell.

In some instances, variant CAR libraries that are expressed in cells are used to identify variant CARs with improved variant gene expression, avidity, stability, affinity, or specificity. For example, a first variant CAR library is generated that comprises improved specificity to a tumor antigen. In some instances, following identification of variant CARs with improved gene expression, avidity, stability, affinity, or specificity, those variant CARs are further varied to produce a second library of variant CARs with a second improvement. For example, variant CARs with improved specificity are further varied to identify variants further comprising improved stability. In some instances, the second library comprises variants in a same region as the first library. In some instances, the second library comprises variants in a different region of the first library. For example, the first library may comprise variants in an antigen recognition domain of the CAR and the second library may comprise variants in a hinge domain, a transmembrane domain, or an intracellular domain of the CAR. In some instances, a number of variant CAR libraries are generated. In some instances, the number of variant CAR libraries is at least 2, 3, 4, 5, 6, 7, 8, 9, 10, 11, 12, or more than 12 variant libraries. In some instances, the variant libraries comprise at least or about $10^1$, $10^2$, $10^3$, $10^4$, $10^5$, or $10^6$ variants. In some instances, each of the variant libraries independently has improvements in gene expression, avidity, stability, affinity, or specificity.

Variant CAR libraries may be engineered into cells and introduced into a subject. In some instances, the cells are autologous, meaning derived from a subject's own cells. Alternately, cells expressing variant CARs are allogeneic, meaning derived from another subject with a similar tissue type. In some instances, cells are tailored to the subject. In some instances, cells are compatible with local tissue.

In some instances, variant nucleic acid libraries as described herein comprise about 50-100000, 100-75000, 250-50000, 500-25000, 1000-15000, 2000-10000, or 4000-8000 sequences. In some instances, variant nucleic acid libraries comprise 500 sequences. In some cases, variant nucleic acid libraries comprise 5000 sequences. In some instances, variant nucleic acid libraries comprise 15000 sequences. In some cases, variant nucleic acid libraries comprise at least 50, 100, 150, 500, 1000, 2000, 5000, 10000, 20000, 50000, 100000, 200000, 400000, 800000, 1000000, or more than 1000000 sequences. Variant nucleic acid libraries may comprise at most 50, 100, 500, 1000, 2000, 5000, 10000, 20000, 50000, 100000, 200000, 400000, 800000, or 1000000 sequences. The total variant library may result in $10^6$, $10^8$, $10^{10}$, $10^{11}$, $10^{12}$, $10^{13}$ or more different nucleic acids.

In some cases, the length of each of the oligonucleotide fragments or average length of the oligonucleotides synthesized may be at least or about at least 10, 15, 20, 25, 30, 35, 40, 45, 50, 100, 150, 200, 300, 400, 500, 2000 nucleotides, or more. The length of each of the oligonucleotide fragments or average length of the oligonucleotides synthesized may be at most or about at most 2000, 500, 400, 300, 200, 150, 100, 50, 45, 35, 30, 25, 20, 19, 18, 17, 16, 15, 14, 13, 12, 11, 10 nucleotides, or less. The length of each of the oligonucleotide fragments or average length of the oligonucleotides synthesized may fall from 10-2000, 10-500, 9-400, 11-300, 12-200, 13-150, 14-100, 15-50, 16-45, 17-40, 18-35, 19-25.

Variant Library Synthesis

Methods described herein provide for synthesis of a library of oligonucleotides each encoding for a predetermined variant of at least one predetermined reference nucleic acid sequence. In some instances, the oligonucleotides synthesized herein are isolated, purified, or isolated and purified. In some cases, the predetermined reference sequence is a nucleic acid sequence encoding for a protein, and the variant library comprises sequences encoding for variation of at least a single codon such that a plurality of different variants of a single residue in the subsequent protein encoded by the synthesized nucleic acid are generated by standard translation processes. The synthesized specific alterations in the nucleic acid sequence may be introduced by incorporating nucleotide changes into overlapping or blunt ended oligonucleotide primers. Alternatively, a population of oligonucleotides may collectively encode for a long nucleic acid (e.g., a gene) and variants thereof. In this arrangement, the population of oligonucleotides may be hybridized and subject to standard molecular biology techniques to form the long nucleic acid (e.g., a gene) and variants thereof. When the long nucleic acid (e.g., a gene) and variants thereof are expressed in cells, a variant protein library is generated. Similarly, provided here are methods for synthesis of variant libraries encoding for RNA sequences (e.g., miRNA, shRNA, and mRNA) or DNA sequences (e.g., enhancer, promoter, UTR, and terminator regions). In some instances, the sequences are exon sequences or coding sequences. In some instances, the sequences do not comprise intron sequences. Also provided here are downstream applications for variants selected out of the libraries synthesized using methods described here. Downstream applications include identification of variant nucleic acid or protein sequences with enhanced biologically relevant functions, e.g., biochemical affinity, enzymatic activity, changes in cellular activity, and for the treatment or prevention of a disease state.

Synthesis Followed by PCR Mutagenesis

A first process for synthesis of a variant library of oligonucleotides is for PCR mutagenesis (saturating or non-saturating) methods. In this workflow, a plurality of oligonucleotides is synthesized, wherein each oligonucleotide encodes for a predetermined sequence which is a predetermined variant of a reference nucleic acid sequence. Referring to the figures, an exemplary workflow in depicted in FIGS. 1A-1D, wherein oligonucleotides are generated on a surface. FIG. 1A depicts an expansion view of a single cluster of a surface with 121 loci. Each oligonucleotide depicted in FIG. 1B is a primer that may be used for amplification from a reference nucleic acid sequence to produce a library of variant long nucleic acids, FIG. 1C. The library of variant long nucleic acids is then, optionally, subject to transcription and or translation to generate a variant RNA or protein library, FIG. 1D. In this exemplary illustration, a device having a substantially planar surface used for de novo synthesis of oligonucleotides is depicted, FIG. 1A. In some instances, the device comprises a cluster of loci, wherein each locus is a site for oligonucleotide extension. In some instances, a single cluster comprises all the oligonucleotide variants needed to generate a desired variant sequence library. In an alternative arrangement, a plate comprises a field of loci which are not segregated into clusters.

In some instances, oligonucleotides synthesized within a cluster (e.g., as seen in FIG. 1A) are amplified by PCR. Such an arrangement may provide for improved oligonucleotide representation compared to amplification of non-identical oligonucleotides across an entire plate without a clustered arrangement. In some instances, amplification of oligonucleotides synthesized on surfaces of loci within a cluster overcomes negative effects on representation due to repeated synthesis of large oligonucleotide populations having oligonucleotides with heavy GC content. In some instances, a cluster described herein, comprises about 50-1000, 75-900, 100-800, 125-700, 150-600, 200-500, 50-500 or 300-400 discrete loci. In some instances, a loci is a spot, well, microwell, channel, or post. In some instances, each cluster has at least 1×, 2×, 3×, 4×, 5×, 6×, 7×, 8×, 9×, 10×, or more redundancy of separate features supporting extension of oligonucleotides having an identical sequence. In some instances, 1× redundancy means not having oligonucleotides with the same sequence.

A de novo synthesized oligonucleotide library described herein may comprise a plurality of oligonucleotides, each with at least one variant sequence at a first position, position "x", and each variant oligonucleotide is used as a primer in a first round of PCR to generate a first extension product. In this example, position "x" in a first oligonucleotide 220 encodes for a variant codon sequence, i.e., one of 19 possible variants from a reference sequence. See FIG. 2A. A second oligonucleotide 225 comprising a sequence overlapping that of the first oligonucleotide is also used as a primer in a separate round of PCR to generate a second extension product. In addition, outer primers 215, 230 may be used for amplification of a fragment from a long nucleic acid sequence. The resultant amplification products are fragments of the long nucleic acid sequence 235, 240. See FIG. 2B. The fragments of the long nucleic acid sequence 235, 240 are then hybridized, and subject to an extension reaction to form a variant of the long nucleic acid 245. See FIG. 2C. The overlapping ends of the first and second extension products may serve as a primer of a second round of PCR, thereby generating a third extension product (FIG. 2D) that contains the variant. To increase the yield, the variant of the long nucleic acid is amplified in a reaction including a DNA polymerase, amplification reagents, and the outer primers 215, 230. In some instances, the second oligonucleotide comprises a sequence adjacent to, but not including, the variant site. In an alternative arrangement, a first oligonucleotide is generated that has a region that overlaps with a second oligonucleotide. In this scenario, the first oligonucleotide is synthesized with variation at a single codon for up to 19 variants. The second oligonucleotide does not comprise a variant sequence. Optionally, a first population comprises the first oligonucleotide variants and additional oligonucleotides encoding for variants at a different codon site. Alternatively, the first oligonucleotide and the second oligonucleotide may be designed for blunt end ligation.

An alternative mutagenesis PCR method is depicted in FIGS. 3A-3F. In such a process, a template nucleic acid molecule 300 comprising a first and second strand 305, 310 is amplified in a PCR reaction containing a first primer 315 and a second primer 320 (FIG. 3A). The amplification reaction includes uracil as a nucleotide reagent. A uracil-labeled extension product 325 (FIG. 3B) is generated, optionally purified, and serves as a template for a subsequent PCR reaction using a first oligonucleotide 335 and a plurality of second oligonucleotides 330 to generate first extension products 340 and 345 (FIGS. 3C-3D). In this process, a plurality of second oligonucleotide 330 comprises oligonucleotides encoding for variant sequences (denoted as X, Y, and Z, in FIG. 3C). The uracil-labeled template nucleic acid is digested by a uracil-specific excision reagent, e.g., USER digest available commercially from New England Biolabs. Variant 335 and different codons 330 with variants X, Y, and Z are added and a limited PCR step is performed to generate FIG. 3D. After the uracil-containing template is digested, the overlapping ends of the extension products serve to prime a PCR reaction with the first extension products 340 and 345 acting as primers in combination with a first outer primer 350 and a second outer primer 355, thereby generating a library of nucleic acid molecules 360 containing a plurality of variants X, Y, and Z at the variant site FIG. 3F.

De Novo Synthesis of a Population with Variant and Non-Variant Portions of a Long Nucleic Acid In a second process for synthesis of a variant library, a surface is used for de novo synthesis of multiple fragments of a long nucleic acid, wherein at least one of the fragments is synthesized in multiple versions, each version being of a different variant sequence. In this arrangement, all of the fragments needed to assemble a library of variant long range nucleic acids are de novo synthesized. The synthesized fragments may have overlapping sequence such that, following synthesis, the fragment library is subject to hybridization. Following hybridization, an extension reaction may be performed to fill in any complementary gaps.

Alternatively, the synthesized fragments may be amplified with primers and then subject to either blunt end ligation or overlapping hybridization. In some instances, the device comprises a cluster of loci, wherein each locus is a site for oligonucleotide extension. In some instances, a single cluster comprises all the oligonucleotide variants and other fragment sequences of a predetermined long nucleic acid to generate a desired variant nucleic acid sequence library. The cluster may comprise about 50 to 500 loci. In some arrangements, a cluster comprises greater than 500 loci.

Each individual oligonucleotide in the first oligonucleotide population may be generated on a separate, individually addressable locus of a cluster. One oligonucleotide variant may be represented by a plurality of individually addressable loci. Each variant in the first oligonucleotide population may be represented 1, 2, 3, 4, 5, 6, 7, 8, 9, 10, or more times. In some instances, each variant in the first oligonucleotide population is represented at 3 or less loci. In some instances, each variant in the first oligonucleotide population is represented at two loci. In some instances, each variant in the first oligonucleotide population is represented at only a single locus.

Methods are provided herein to generate nucleic acid libraries with reduced redundancy. In some instances, variant oligonucleotides may be generated without the need to synthesize the variant oligonucleotide more than 1 time to obtain the desired variant oligonucleotide. In some instances, the present disclosure provides methods to generate variant oligonucleotides without the need to synthesize the variant oligonucleotide more than 1, 2, 3, 4, 5, 6, 7, 8, 9, 10, or more times to generate the desired variant oligonucleotide.

Variant oligonucleotides may be generated without the need to synthesize the variant oligonucleotide at more than 1 discrete site to obtain the desired variant oligonucleotide. The present disclosure provides methods to generate variant oligonucleotides without the need to synthesize the variant oligonucleotide at more than 1 site, 2 sites, 3 sites, 4 sites, 5 sites, 6 sites, 7 sites, 8 sites, 9 sites, or 10 sites. In some instances, an oligonucleotide is synthesized in at most 6, 5, 4, 3, 2, or 1 discrete sites. The same oligonucleotide may be synthesized in 1, 2, or 3 discrete loci on a surface.

In some instances, the amount of loci representing a single variant oligonucleotide is a function of the amount of nucleic acid material required for downstream processing, e.g., an amplification reaction or cellular assay. In some instances, the amount of loci representing a single variant oligonucleotide is a function of the available loci in a single cluster.

Provided herein are methods for generation of a library of oligonucleotides comprising variant oligonucleotides differing at a plurality of sites in a reference nucleic acid. In such cases, each variant library is generated on an individually addressable locus within a cluster of loci. It will be understood that the number of variant sites represented by the oligonucleotide library will be determined by the number of individually addressable loci in the cluster and the number of desired variants at each site. In some instances, each cluster comprises about 50 to 500 loci. In some instances, each cluster comprises 100 to 150 loci.

In an exemplary arrangement, 19 variants are represented at a variant site corresponding to codons encoding for each of the 19 possible variant amino acids. In another exemplary case, 61 variants are represented at a variant site corresponding to triplets encoding for each of the 19 possible variant amino acids. In a non-limiting example, a cluster comprises 121 individually addressable loci. In this example, an oligonucleotide population comprises 6 replicates each of a single-site variant (6 replicates×1 variant site×19 variants=114 loci), 3 replicates each of a double-site variant (3 replicates×2 variant sites×19 variants=114 loci), or 2 replicates each of a triple-site variant (2 replicates×3 variant sites×19 variants=114 loci). In some instances, an oligonucleotide population comprises variants at four, five, six or more than six variant sites.

Provided herein are methods and compositions for production of synthetic (i.e. de novo synthesized or chemically synthesized) oligonucleotides. Libraries of synthesized oligonucleotides described herein may comprise a plurality of oligonucleotides collectively encoding for one or more genes or gene fragments. In some instances, the oligonucleotide library comprises coding or non-coding sequences. In some instances, the oligonucleotide library encodes for a plurality of cDNA sequences. In some instances, the oligonucleotide library comprises one or more oligonucleotides, each of the one or more oligonucleotides encoding sequences for multiple exons. Each oligonucleotide within a library described herein may encode a different sequence, i.e., non-identical sequence. In some instances, each oligonucleotide within a library described herein comprises at least one portion that is complementary to a sequence of another oligonucleotide within the library. Oligonucleotide sequences described herein may, unless stated otherwise, comprise DNA or RNA.

Provided herein are methods and compositions for production of synthetic (i.e. de novo synthesized) genes. Libraries comprising synthetic genes may be constructed by a variety of methods described in further detail elsewhere herein, such as PCA, non-PCA gene assembly methods or hierarchical gene assembly, combining ("stitching") two or more double-stranded oligonucleotides to produce larger DNA units (i.e., a chassis). Libraries of large constructs may involve oligonucleotides that are at least 1, 1.5, 2, 3, 4, 5, 6, 7, 8, 9, 10, 15, 20, 30, 40, 50, 60, 70, 80, 90, 100, 125, 150, 175, 200, 250, 300, 400, 500 kb long or longer. The large constructs may be bound by an independently selected upper limit of about 5000, 10000, 20000 or 50000 base pairs. The synthesis of any number of polypeptide-segment encoding nucleotide sequences may include sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest. The following are non-limiting examples of oligonucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, which is a DNA representation of mRNA, usually obtained by reverse transcription of messenger RNA (mRNA) or by amplification; DNA molecules produced synthetically or by amplification, genomic DNA, recombinant oligonucleotides, branched oligonucleotides, plasmids, vectors, isolated DNA of any sequence, isolated RNA of any sequence, nucleic acid probes, and primers. In the context of cDNA, the term gene or gene fragment refers to a DNA nucleic acid sequence comprising at least one region encoding for exon sequences without an intervening intron sequence.

In various embodiments, methods and compositions described herein relate to a library of genes. The gene library may comprise a plurality of subsegments. In one or more subsegments, the genes of the library may be covalently linked together. In one or more subsegments, the genes of the library may encode for components of a first metabolic pathway with one or more metabolic end products. In one or more subsegments, genes of the library may be selected based on the manufacturing process of one or more targeted metabolic end products. The one or more metabolic end products may comprise a biofuel. In one or more subsegments, the genes of the library may encode for components of a second metabolic pathway with one or more metabolic end products. The one or more end products of the first and second metabolic pathways may comprise one or more shared end products. In some cases, the first metabolic pathway comprises an end product that is manipulated in the second metabolic pathway.

Codon Variation

Variant oligonucleotide libraries described herein may comprise a plurality of oligonucleotides, wherein each oligonucleotide encodes for a variant codon sequence compared to a reference nucleic acid sequence. In some instances, each oligonucleotide of a first oligonucleotide population contains a variant at a single variant site. In some instances, the first oligonucleotide population contains a plurality of variants at a single variant site such that the first oligonucleotide population contains more than one variant at the same variant site. The first oligonucleotide population may comprise oligonucleotides collectively encoding multiple codon variants at the same variant site. The first oligonucleotide population may comprise oligonucleotides collectively encoding up to 19 or more codons at the same position. The first oligonucleotide population may comprise oligonucleotides collectively encoding up to 60 variant triplets at the same position, or the first oligonucleotide population may comprise oligonucleotides collectively encoding up to 61 different triplets of codons at the same position. Each variant may encode for a codon that results in a different amino acid during translation. Table 4 provides a listing of each codon possible (and the representative amino acid) for a variant site.

TABLE 4

List of codons and amino acids

| Amino Acids | One letter code | Three letter code | Codons | | | |
|---|---|---|---|---|---|---|
| Alanine | A | Ala | GCA | GCC | GCG | GCT |
| Cysteine | C | Cys | TGC | TGT | | |
| Aspartic acid | D | Asp | GAC | GAT | | |
| Glutamic acid | E | Glu | GAA | GAG | | |
| Phenylalanine | F | Phe | TTC | TTT | | |
| Glycine | G | Gly | GGA | GGC | GGG | GGT |
| Histidine | H | His | CAC | CAT | | |
| Isoleucine | I | Iso | ATA | ATC | ATT | |
| Lysine | K | Lys | AAA | AAG | | |
| Leucine | L | Leu | TTA | TTG | CTA | CTC | CTG | CTT |
| Methionine | M | Met | ATG | | | |
| Asparagine | N | Asn | AAC | AAT | | |
| Proline | P | Pro | CCA | CCC | CCG | CCT |
| Glutamine | Q | Gln | CAA | CAG | | |
| Arginine | R | Arg | AGA | AGG | CGA | CGC | CGG | CGT |
| Serine | S | Ser | AGC | AGT | TCA | TCC | TCG | TCT |
| Threonine | T | Thr | ACA | ACC | ACG | ACT |
| Valine | V | Val | GTA | GTC | GTG | GTT |
| Tryptophan | W | Trp | TGG | | | |
| Tyrosine | Y | Tyr | TAC | TAT | | |

Provided herein are nucleic acid libraries that may comprise a plurality of nucleic acids, wherein each nucleic acid encodes for a variant codon sequence compared to a reference nucleic acid sequence. In some instances, each nucleic acid of a first nucleic acid population contains a variant at a single variant site. In some instances, the first nucleic acid population contains a plurality of variants at a single variant site such that the first nucleic acid population contains more than one variant at the same variant site. The first nucleic acid population may comprise nucleic acids collectively encoding multiple codon variants at the same variant site. The first oligonucleotide population may comprise nucleic acids collectively encoding up to 19 or more codons at the same position. The first nucleic acid population may comprise nucleic acids collectively encoding up to 60 variant triplets at the same position, or the first nucleic acid population may comprise oligonucleotides collectively encoding up to 61 different triplets of codons at the same position. Each variant may encode for a codon that results in a different amino acid during translation.

An oligonucleotide population may comprise varied oligonucleotides collectively encoding up to 20 codon variations at multiple positions. In such cases, each oligonucleotide in the population comprises variation for codons at more than one position in the same oligonucleotide. In some instances, each oligonucleotide in the population comprises variation for codons at 1, 2, 3, 4, 5, 6, 7, 8, 9, 10, 11, 12, 13, 14, 15, 16, 17, 18, 19, 20 or more codons in a single oligonucleotide. In some instances, each variant long nucleic acid comprises variation for codons at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more codons in a single long nucleic acid. In some instances, the variant oligonucleotide population comprises variation for codons at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more codons in a single oligonucleotide. In some instances, the variant oligonucleotide population comprises variation for codons in at least about 10, 20, 30, 40, 50, 60, 70, 80, 90, 100 or more codons in a single long nucleic acid.

Provided herein are processes where a second oligonucleotide population is generated on a second cluster containing a plurality of individually addressable loci. The second oligonucleotide population may comprise a plurality of second oligonucleotides that are constant for each codon position (i.e., encode the same amino acid at each position). The second oligonucleotide may overlap with at least a portion of the first oligonucleotides. In some instances, the second oligonucleotides do not contain the variant site represented on the first oligonucleotides. Alternatively, the second oligonucleotide population may comprise a plurality of second oligonucleotides that contain at least one variant for one or more codon positions.

Provided herein are methods for synthesizing a library of oligonucleotides where a single population of oligonucleotides is generated comprising variants at multiple codon positions. A first oligonucleotide population may be generated on a first cluster containing a plurality of individually addressable loci. In such cases, the first oligonucleotide population comprises variants at different codon positions. In some instances, the different sites are consecutive (i.e., encoding consecutive amino acids). For example, the first oligonucleotide population comprises variants in two consecutive codon positions, encoding up to 19 variants at a position. In some instances, the first oligonucleotide population comprises variants in two consecutive codon positions, encoding from about 1 to about 19 variants at a position. In some instances, about 38 oligonucleotides are synthesized. In some instances, the oligonucleotides comprising variants in two consecutive codon positions comprise a range of about 36 to about 66 bases in length. A first oligonucleotide population may comprise varied oligonucleotides collectively encoding up to 19 codon variants at the same, or additional variant site. A first oligonucleotide population may include a plurality of first oligonucleotides that contains up to 19 variants at position x, up to 19 variants at position y, and up to 19 variants at position z. In such an arrangement, each variant encodes a different amino acid such that up to 19 amino acid variants are encoded at each of the different variant sites. In an additional instance, a second oligonucleotide population is generated on a second cluster containing a plurality of individually addressable loci. The second oligonucleotide population may comprise a plurality of second oligonucleotides that are constant for each codon position (i.e., encode the same amino acid at each position). The second oligonucleotides may overlap with at least a portion of the first oligonucleotides. The second oligonucleotides may not contain the variant site represented on the first oligonucleotides.

Figure 4A:
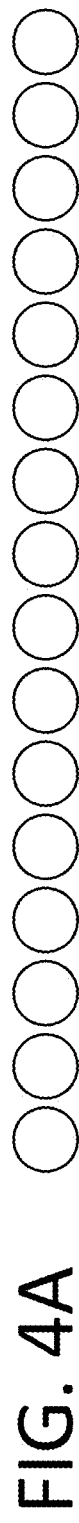
FIGS. 4A-4E depict a reference amino acid sequence (FIG. 4A) having a number of amino acids, each residue indicated by a single circle, and variant amino acid sequences (FIGS. 4B, 4C, 4D, & 4E) generated using methods described herein. The reference amino acid sequence and variant sequences are encoded by nucleic acids and variants thereof generated by processes described herein.
Figure 4B:
Figure 4C:
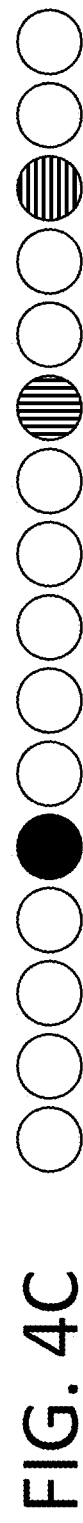
Figure 4D:
Figure 4E:

Variant nucleic acid libraries generated by processes described herein provide for the generation of variant protein libraries. In a first exemplary arrangement, a template oligonucleotide encodes for a sequence that, when transcribed and translated, results in a reference amino acid sequence (FIG. 4A) having a number of codon positions, indicated by a single circle. Oligonucleotide variants of the template may be generated using methods described herein. In some instances, a single variant is present in the oligonucleotide, resulting in a single amino acid sequence (FIG. 4B). In some instances, more than one variant is present in the oligonucleotide, wherein the variants are separated by one or more codons, resulting in a protein with spacing between variant residues (FIG. 4C). In some instances, more than one variant is present in the oligonucleotide, wherein the variants are sequential and adjacent or consecutive to one another, resulting in spaced variant stretches of residues (FIG. 4D). In some instances, two stretches of variants are present in the oligonucleotide, wherein each stretch of variants comprises sequential and adjacent or consecutive variants (FIG. 4E).

Figures 5A, 5B:
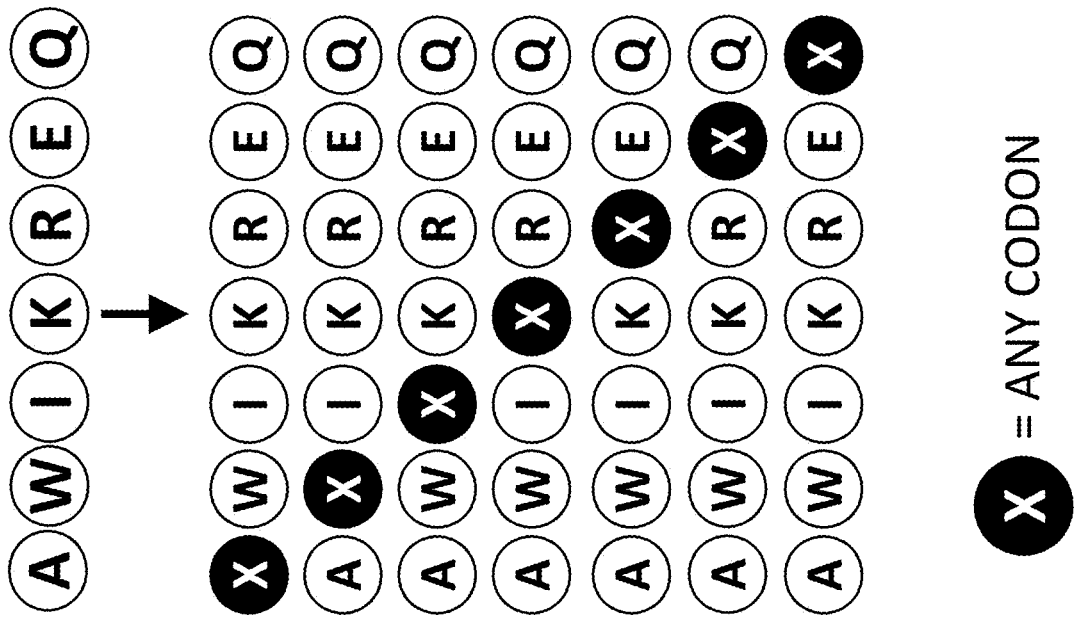
FIGS. 5A-5B depict a reference amino acid sequence (FIG. 5A) and a library of variant amino acid sequences (FIG. 5B), each variant comprising a single residue variant (indicated by an "X"). The reference amino acid sequence and variant sequences are encoded by nucleic acids and variants thereof generated by processes described herein.

Provided herein are methods to generate a library of oligonucleotide variants, wherein each variant comprises a single position codon variant. In one instance, a template oligonucleotide has a number of codon positions wherein exemplary amino acid residues are indicated by circles with their respective one letter code protein codon, FIG. 5A. FIG. 5B depicts a library of amino acid variants encoded by a library of variant nucleic acids, wherein each variant comprises a single position variant, indicated by an "X", located at a different single site. A first position variant has any codon to replace alanine, a second variant with any codon encoded by the library of variant nucleic acids to replace tryptophan, a third variant with any codon to replace isoleucine, a fourth variant with any codon to replace lysine, a fifth variant with any codon to replace arginine, a sixth variant with any codon to replace glutamic acid, and a seventh variant with any codon to replace glutamine. When all or less than all codon variants are encoded by the variant nucleic acid library, a resulting corresponding population of amino acid sequence variants is generated following protein expression (i.e., standard cellular events of DNA transcription followed by translation and processing events).

In some arrangements, a library is generated with multiple sites of single position variants. As depicted in FIG. 6A, a wild-type template is provided. FIG. 6B depicts the resultant amino acid sequence with two sites of single position codon variants, wherein each codon variant encoding for a different amino acid is indicated by differently patterned circles.

Provided herein are methods to generate a library having a stretch of multiple site, single position variants. Each stretch of oligonucleotide or nucleic acid may have 1, 2, 3, 4, 5, or more variants. Each stretch of oligonucleotide or nucleic acid may have at least 1 variant. Each stretch of oligonucleotide or nucleic acid may have at least 2 variants. Each stretch of oligonucleotide or nucleic acid may have at least 3 variants. For example, a stretch of 5 oligonucleotides or nucleic acids may have 1 variant. A stretch of 5 oligonucleotides or nucleic acids may have 2 variants. A stretch of 5 oligonucleotides or nucleic acids may have 3 variants. A stretch of 5 oligonucleotides or nucleic acids may have 4 variants. For example, a stretch of 4 oligonucleotides or nucleic acids may have 1 variant. A stretch of 4 oligonucleotides or nucleic acids may have 2 variants. A stretch of 4 oligonucleotides or nucleic acids may have 3 variants. A stretch of 4 oligonucleotides or nucleic acids may have 4 variants.

Figures 7A, 7B:
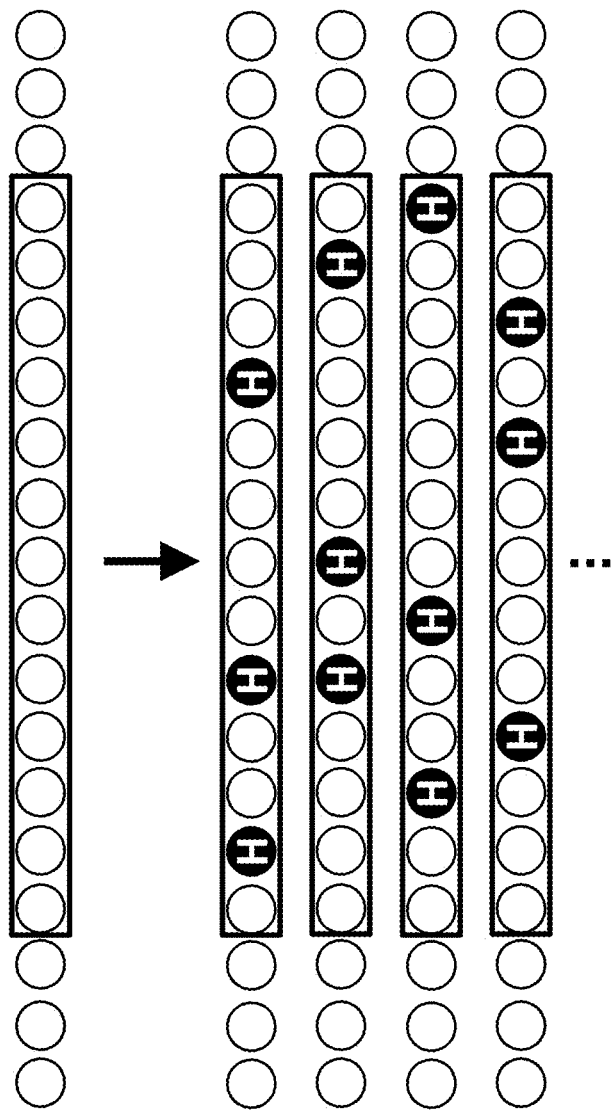
FIGS. 7A-7B depict a reference amino acid sequence (FIG. 7A) and a library of variant amino acid sequences (FIG. 7B), each variant comprising a stretch of amino acids (indicated by a box around the circles), each stretch having three sites of position variants (encoding for histidine) differing in sequence from the reference amino acid sequence. The reference amino acid sequence and variant sequences are encoded by nucleic acids and variants thereof generated by processes described herein.

In some instances, single position variants may all encode for the same amino acid, e.g. a histidine. As depicted in FIG. 7A, a reference amino acid sequence is provided. In this arrangement, a stretch of an oligonucleotide encodes for multiple sites of single position variants and, when expressed, results in an amino acid sequence having all single position variants encoding for a histidine, FIG. 7B. In some embodiments, a variant library synthesized by methods described herein does not encode for more than 4 histidine residues in a resultant amino acid sequence.

Figures 8A, 8B:
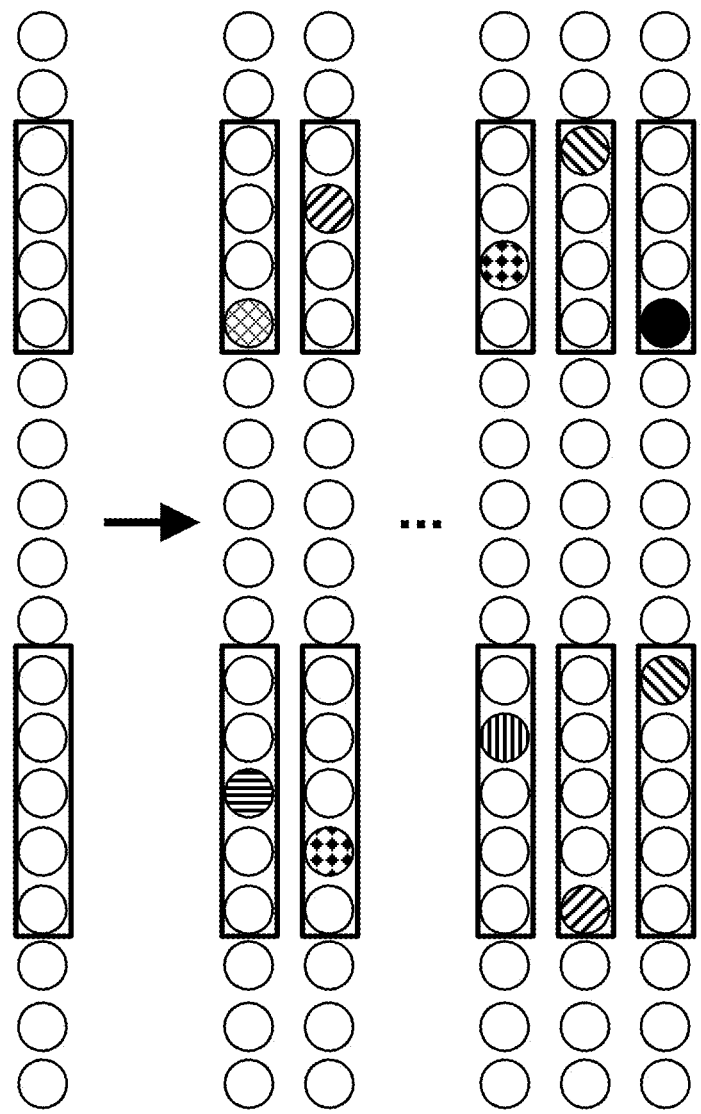
FIGS. 8A-8B depict a reference amino acid sequence (FIG. 8A) and a library of variant amino acid sequences (FIG. 8B), each variant comprising two stretches of amino acid sequence (indicated by a box around the circles), each stretch having one site of single position variants (illustrated by the patterned circles) differing in sequence from reference amino acid sequence. The reference amino acid sequence and variant sequences are encoded by nucleic acids and variants thereof generated by processes described herein.

In some instances, a variant library of nucleic acids generated by methods described herein provides for expression of amino acid sequences having separate stretches of variation. A template amino acid sequence is depicted in FIG. 8A. A stretch of oligonucleotides may have only 1 variant codon in two stretches and, when expressed, result in an amino acid sequence depicted in FIG. 8B. Variants are depicted in FIG. 8B by the differently patterned circles to indicate variation in amino acids at different positions in a single stretch.

Figures 9A, 9B:
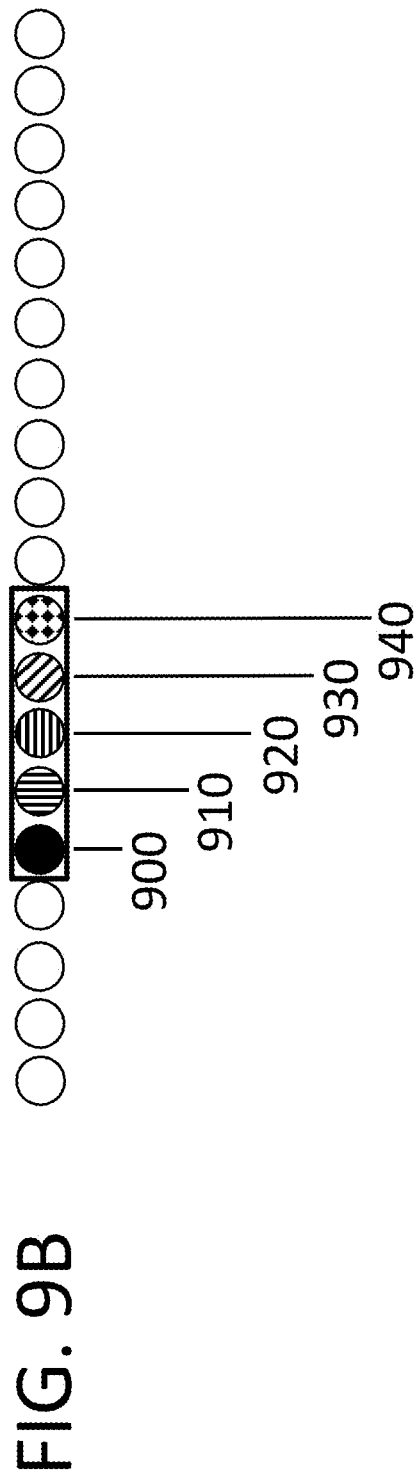
FIGS. 9A-9B depict a reference amino acid sequence (FIG. 9A) and a library of amino acid sequence variants (FIG. 9B), each variant comprising a stretch of amino acids (indicated by patterned circles), each stretch having a single site of multiple position variants differing in sequence from the reference amino acid sequence. In this illustration, 5 positions are varied where the first position has a 50/50 K/R ratio; the second position has a 50/25/25 V/L/S ratio, the third position has a 50/25/25 Y/R/D ratio, the fourth position has an equal ratio for all amino acids, and the fifth position has a 75/25 ratio for G/P. The reference amino acid sequence and variant sequences are encoded by nucleic acids and variants thereof generated by processes described herein.

Provided herein are methods and devices to synthesize oligonucleotide or nucleic acid libraries with 1, 2, 3, or more codon variants, wherein the variant for each site is selectively controlled. The ratio of two amino acids for a single site variant may be about 1:100, 1:50, 1:10, 1:5, 1:3, 1:2, 1:1. The ratio of three amino acids for a single site variant may be about 1:1:100, 1:1:50, 1:1:20, 1:1:10, 1:1:5, 1:1:3, 1:1:2, 1:1:1, 1:10:10, 1:5:5, 1:3:3, or 1:2:2. FIG. 9A depicts a wild-type reference amino acid sequence encoded by a wild-type nucleic acid sequence. FIG. 9B depicts a library of amino acid variants, wherein each variant comprising a stretch of sequence (indicated by the patterned circles), wherein each position may have a certain ratio of amino acids in the resultant variant protein library. The resultant variant protein library is encoded by a variant nucleic acid library generated by methods described herein. In this illustration, 5 positions are varied: the first position 900 has a 50/50 K/R ratio; the second position 910 has a 50/25/25 V/L/S ratio, the third position 920 has a 50/25/25 Y/R/D ratio, the fourth position 930 has an equal ratio for all 20 amino acids, and the fifth position 940 has a 75/25 ratio for G/P. The ratios described herein are exemplary only.

Variation in Expression Cassettes

Figure 11:
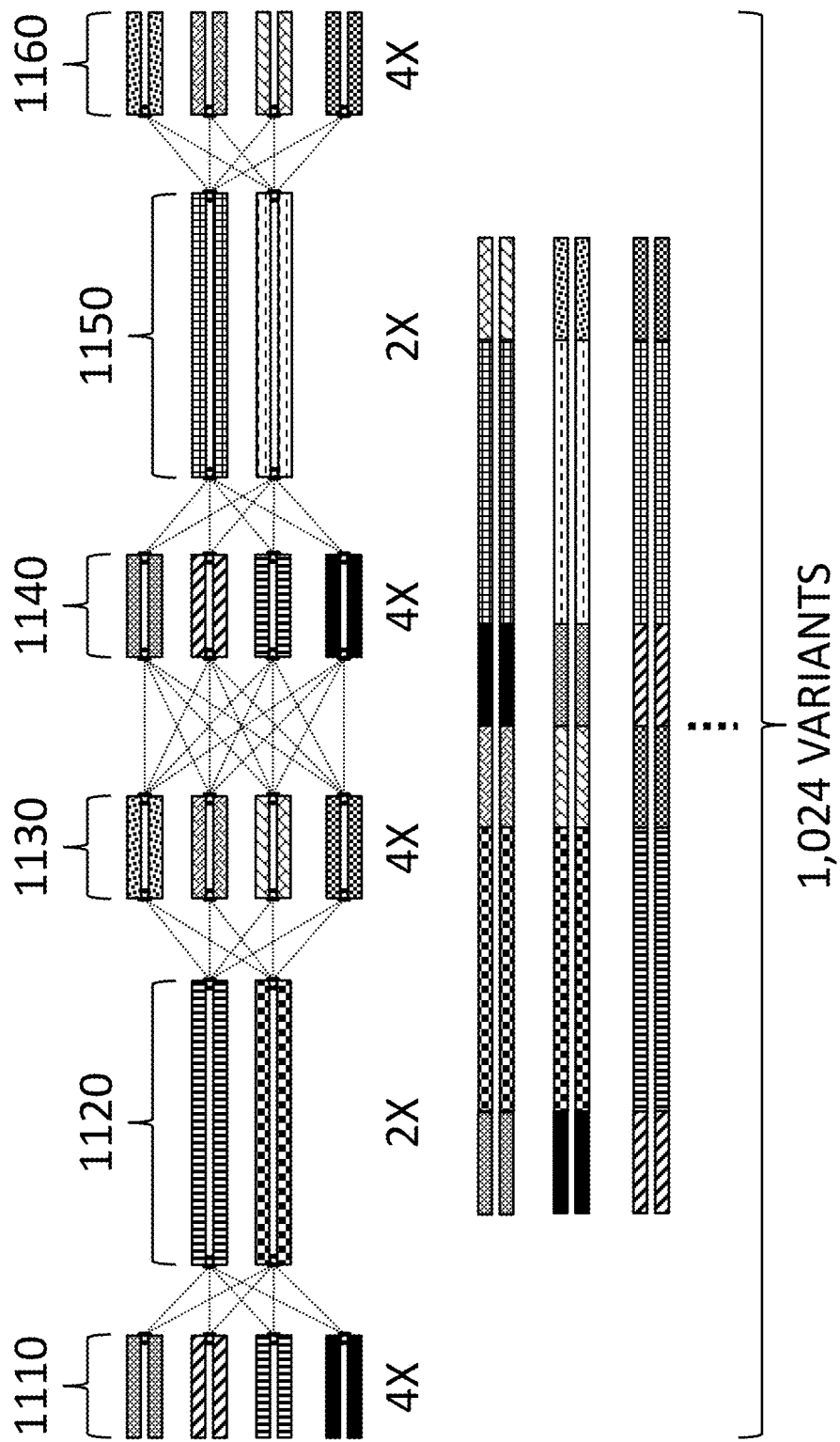
FIG. 11 depicts an exemplary number of variants produced by interchanging sections of two expression cassettes (e.g., promoters, open reading frames, and terminators) to generate a variant library of expression cassettes.

In some instances, a synthesized variant library is generated which encodes for a portion of an expression construct. Exemplary portions of an expression construct include the promoter, open reading frame, and termination region. In some instances, the expression construct encodes for one, two, three or more expression cassettes. An oligonucleotide library may be generated, encoding for codon variation at a single site or multiple sites in separate regions that make up portions of an expression construct cassette, as depicted in FIG. 11. To generate a two construct expressing cassette, variant oligonucleotides were synthesized encoding at least a portion of a variant sequence of a first promoter 1110, first open reading frame 1120, first terminator 1130, second promoter 1140, second open reading frame 1150, or second terminator sequence 1160. After rounds of amplification, as described in previous examples, a library of 1,024 expression constructs was generated. FIG. 11 provides but one example arrangement. In some instances, additional regulator sequences, such as untranslated regulatory region (UTR) or an enhancer region, are also included in an expression cassette referred to herein. An expression cassette may comprise 1, 2, 3, 4, 5, 6, 7, 8, 9, 10 or more components for which variant sequences are generated by methods described herein. In some instances, the expression construct comprises more than one gene in a multicistronic vector. In one example, the synthesized DNA nucleic acids are inserted into viral vectors (e.g., a lentivirus) and then packaged for transduction into cells, or non-viral vectors for transfer into cells, followed by screening and analysis.

Expression vectors for inserting nucleic acids disclosed herein comprise mammalian cells, e.g., human, non-human primate, pig, rabbit and mouse. Exemplary expression vectors include, without limitation, mammalian expression vectors: pSF-CMV-NEO-NH2-PPT-3XFLAG, pSF-CMV-NEO-COOH-3XFLAG, pSF-CMV-PURO-NH2-GST-TEV, pSF-OXB20-COOH-TEV-FLAG(R)-6His ("6His" disclosed as SEQ ID NO: 41), pCEP4 pDEST27, pSF-CMV-Ub-KrYFP, pSF-CMV-FMDV-daGFP, pEF1a-mCherry-N1 Vector, pEF1a-tdTomato Vector, pSF-CMV-FMDV-Hygro, pSF-CMV-PGK-Puro, pMCP-tag(m), and pSF-CMV-PURO-NH2-CMYC. Nucleic acids synthesized by methods described herein may be transferred into cells by various methods known in the art, including, without limitation, transfection, transduction, and electroporation. Exemplary cellular functions tested include, without limitation, changes in cellular proliferation, death, migration/adhesion, metabolic, and cell-signaling activity.

Highly Parallel Nucleic Acid Synthesis

Provided herein is a platform approach utilizing miniaturization, parallelization, and vertical integration of the end-to-end process from oligonucleotide synthesis to gene assembly within nanowells on silicon to create a revolutionary synthesis platform. Devices described herein provide, with the same footprint as a 96-well plate, a silicon synthesis platform capable of increasing throughput by a factor of up to 1,000 or more compared to traditional synthesis methods, with production of up to approximately 1,000,000 or more oligonucleotides, or 10,000 or more genes in a single highly-parallelized run.

With the advent of next-generation sequencing, high resolution genomic data has become an important factor for studies that delve into the biological roles of various genes in both normal biology and disease pathogenesis. At the core of this research is the central dogma of molecular biology and the concept of "residue-by-residue transfer of sequential information." Genomic information encoded in the DNA is transcribed into a message that is then translated into the protein that is the active product within a given biological pathway.

Another exciting area of study is on the discovery, development and manufacturing of therapeutic molecules focused on a highly-specific cellular target. High diversity DNA sequence libraries are at the core of development pipelines for targeted therapeutics. Gene mutants are used to express proteins in a design, build, and test protein engineering cycle that ideally culminates in an optimized gene for high expression of a protein with high affinity for its therapeutic target. As an example, consider the binding pocket of a receptor. The ability to test all sequence permutations of all residues within the binding pocket simultaneously will allow for a thorough exploration, increasing chances of success. Saturation mutagenesis, in which a researcher attempts to generate all possible mutations at a specific site within the receptor, represents one approach to this development challenge. Though costly and time and labor-intensive, it enables each variant to be introduced into each position. In contrast, combinatorial mutagenesis, where a few selected positions or short stretch of DNA may be modified extensively, generates an incomplete repertoire of variants with biased representation.

To accelerate the drug development pipeline, a library with the desired variants available at the intended frequency in the right position available for testing—in other words, a precision library, enables reduced costs as well as turn-around time for screening. Provided herein are methods for synthesizing nucleic acid synthetic variant libraries which provide for precise introduction of each intended variant at the desired frequency. To the end user, this translates to the ability to not only thoroughly sample sequence space but also be able to query these hypotheses in an efficient manner, reducing cost and screening time. Genome-wide editing may elucidate important pathways, libraries where each variant and sequence permutation may be tested for optimal functionality, and thousands of genes may be used to reconstruct entire pathways and genomes to re-engineer biological systems for drug discovery.

In a first example, a drug itself may be optimized using methods described herein. For example, to improve a specified function of an antibody, a variant oligonucleotide library encoding for a portion of the antibody is designed and synthesized. A variant oligonucleotide library for the antibody may then be generated by processes described herein (e.g., PCR mutagenesis followed by insertion into a vector). The antibody is then expressed in a production cell line and screened for enhanced activity. Example screens include examining modulation in binding affinity to an antigen, stability, or effector function (e.g., ADCC, complement, or apoptosis). Exemplary regions to optimize the antibody include, without limitation, the Fc region, Fab region, variable region of the Fab region, constant region of the Fab region, variable domain of the heavy chain or light chain ($V_H$ or $V_L$), and specific complementarity-determining regions (CDRs) of $V_H$ or $V_L$.

Nucleic acid libraries synthesized by methods described herein may be expressed in various cells associated with a disease state. Cells associated with a disease state include cell lines, tissue samples, primary cells from a subject, cultured cells expanded from a subject, or cells in a model system. Exemplary cells include without limitation, prokaryotic and eukaryotic cells. Exemplary eukaryotic cells include, without limitation, animal, plant, and fungal cells. Exemplary animal cells include, without limitation, insect, fish and mammalian cells. Exemplary mammalian cells include mouse, human, and primate cells. Exemplary model systems include, without limitation, plant and animal models of a disease state. Exemplary animals include, without limitation, mice, rabbits, primates, fish, and insects. Exemplary plants include, without limitation, a monocot and dicot. Exemplary plants also include, without limitation, microalgae, kelp, cyanobacteria, and green, brown and red algae, wheat, tobacco, and corn, rice, cotton, vegetables, and fruit.

To identify a variant molecule associated with prevention, reduction or treatment of a disease state, a variant nucleic acid library described herein is expressed in a cell associated with a disease state, or one in which a cell a disease state may be induced. In some instances, an agent is used to induce a disease state in cells. Exemplary tools for disease state induction include, without limitation, a Cre/Lox recombination system, LPS inflammation induction, and streptozotocin to induce hypoglycemia. The cells associated with a disease state may be cells from a model system or cultured cells, as well as cells from a subject having a particular disease condition. Exemplary disease conditions include a bacterial, fungal, viral, autoimmune, or proliferative disorder (e.g., cancer). In some instances, the variant nucleic acid library is expressed in the model system, cell line, or primary cells derived from a subject, and screened for changes in at least one cellular activity. Exemplary cellular activities include, without limitation, proliferation, cycle progression, cell death, adhesion, migration, reproduction, cell signaling, energy production, oxygen utilization, metabolic activity, and aging, response to free radical damage, or any combination thereof.

Substrates

Provided herein are substrates comprising a plurality of clusters, wherein each cluster comprises a plurality of loci that support the attachment and synthesis of oligonucleotides. The term "locus" as used herein refers to a discrete region on a structure which provides support for oligonucleotides encoding for a single predetermined sequence to extend from the surface. In some instances, a locus is on a two dimensional surface, e.g., a substantially planar surface. In some instances, a locus refers to a discrete raised or lowered site on a surface e.g., a well, microwell, channel, or post. In some instances, a surface of a locus comprises a material that is actively functionalized to attach to at least one nucleotide for oligonucleotide synthesis, or preferably, a population of identical nucleotides for synthesis of a population of oligonucleotides. In some instances, oligonucleotide refers to a population of oligonucleotides encoding for the same nucleic acid sequence. In some instances, a surface of a device is inclusive of one or a plurality of surfaces of a substrate.

Average error rates for oligonucleotides synthesized within a library using the systems and methods provided may be less than 1 in 1000, less than 1 in 1250, less than 1 in 1500, less than 1 in 2000, less than 1 in 3000 or less often. In some instances, average error rates for oligonucleotides synthesized within a library using the systems and methods provided are less than 1/500, 1/600, 1/700, 1/800, 1/900, 1/1000, 1/1100, 1/1200, 1/1250, 1/1300, 1/1400, 1/1500, 1/1600, 1/1700, 1/1800, 1/1900, 1/2000, 1/3000, or less. In some instances, average error rates for oligonucleotides synthesized within a library using the systems and methods provided are less than 1/1000.

In some instances, aggregate error rates for oligonucleotides synthesized within a library using the systems and methods provided are less than 1/500, 1/600, 1/700, 1/800, 1/900, 1/1000, 1/1100, 1/1200, 1/1250, 1/1300, 1/1400, 1/1500, 1/1600, 1/1700, 1/1800, 1/1900, 1/2000, 1/3000, or less compared to the predetermined sequences. In some instances, aggregate error rates for oligonucleotides synthesized within a library using the systems and methods provided herein are less than 1/500 or less compared to the predetermined sequences. In some instances, aggregate error rates for oligonucleotides synthesized within a library using the systems and methods provided are less than 1/500, 1/600, 1/700, 1/800, 1/900, or 1/1000. In some instances, aggregate error rates for oligonucleotides synthesized within a library using the systems and methods provided are less than 1/1000.

In some instances, an error correction enzyme may be used for oligonucleotides synthesized within a library using the systems and methods provided herein. In some instances, aggregate error rates for oligonucleotides with error correction may be less than 1/500, 1/600, 1/700, 1/800, 1/900, 1/1000, 1/1100, 1/1200, 1/1300, 1/1400, 1/1500, 1/1600, 1/1700, 1/1800, 1/1900, 1/2000, 1/3000, or less compared to the predetermined sequences. In some instances, aggregate error rates with error correction for oligonucleotides synthesized within a library using the systems and methods provided may be less than 1/500, 1/600, 1/700, 1/800, 1/900, or 1/1000. In some instances, aggregate error rates with error correction for oligonucleotides synthesized within a library using the systems and methods provided may be less than 1/1000.

Error rate may limit the value of gene synthesis for the production of libraries of gene variants. With an error rate of 1/300, about 0.7% of the clones in a 1500 base pair gene will be correct. As most of the errors from oligonucleotide synthesis result in frame-shift mutations, over 99% of the clones in such a library will not produce a full-length protein. Reducing the error rate by 75% would increase the fraction of clones that are correct by a factor of 40. The methods and compositions of the disclosure allow for fast de novo synthesis of large oligonucleotide and gene libraries with error rates that are lower than commonly observed gene synthesis methods both due to the improved quality of synthesis and the applicability of error correction methods that are enabled in a massively parallel and time-efficient manner. Accordingly, libraries may be synthesized with base insertion, deletion, substitution, or total error rates that are under 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less, across the library, or across more than 80%, 85%, 90%, 93%, 95%, 96%, 97%, 98%, 99%, 99.5%, 99.8%, 99.9%, 99.95%, 99.98%, 99.99%, or more of the library. The methods and compositions of the disclosure further relate to large synthetic oligonucleotide and gene libraries with low error rates associated with at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of the oligonucleotides or genes in at least a subset of the library to relate to error free sequences in comparison to a predetermined/preselected sequence. In some instances, at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of the oligonucleotides or genes in an isolated volume within the library have the same sequence. In some instances, at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of any oligonucleotides or genes related with more than 95%, 96%, 97%, 98%, 99%, 99.5%, 99.6%, 99.7%, 99.8%, 99.9% or more similarity or identity have the same sequence. In some instances, the error rate related to a specified locus on an oligonucleotide or gene is optimized.

Thus, a given locus or a plurality of selected loci of one or more oligonucleotides or genes as part of a large library may each have an error rate that is less than 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less. In various instances, such error optimized loci may comprise at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 1500, 2000, 2500, 3000, 4000, 5000, 6000, 7000, 8000, 9000, 10000, 30000, 50000, 75000, 100000, 500000, 1000000, 2000000, 3000000 or more loci. The error optimized loci may be distributed to at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 1500, 2000, 2500, 3000, 4000, 5000, 6000, 7000, 8000, 9000, 10000, 30000, 75000, 100000, 500000, 1000000, 2000000, 3000000 or more oligonucleotides or genes.

The error rates may be achieved with or without error correction. The error rates may be achieved across the library, or across more than 80%, 85%, 90%, 93%, 95%, 96%, 97%, 98%, 99%, 99.5%, 99.8%, 99.9%, 99.95%, 99.98%, 99.99%, or more of the library.

Provided herein are structures that may comprise a surface that supports the synthesis of a plurality of oligonucleotides having different predetermined sequences at addressable locations on a common support. In some instances, a device provides support for the synthesis of more than 2,000; 5,000; 10,000; 20,000; 30,000; 50,000; 75,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical oligonucleotides. In some instances, the device provides support for the synthesis of more than 2,000; 5,000; 10,000; 20,000; 30,000; 50,000; 75,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more oligonucleotides encoding for distinct sequences. In some instances, at least a portion of the oligonucleotides have an identical sequence or are configured to be synthesized with an identical sequence.

Provided herein are methods and devices for manufacture and growth of oligonucleotides about 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, or 2000 bases in length. In some instances, the length of the oligonucleotide formed is about 5, 10, 20, 30, 40, 50, 60, 70, 80, 90, 100, 125, 150, 175, 200, or 225 bases in length. An oligonucleotide may be at least 5, 10, 20, 30, 40, 50, 60, 70, 80, 90, or 100 bases in length. An oligonucleotide may be from 10 to 225 bases in length, from 12 to 100 bases in length, from 20 to 150 bases in length, from 20 to 130 bases in length, from 30 to 100 bases in length, or from 30 to 70 bases in length.

In some instances, oligonucleotides are synthesized on distinct loci of a substrate, wherein each locus supports the synthesis of a population of oligonucleotides. In some instances, each locus supports the synthesis of a population of oligonucleotides having a different sequence than a population of oligonucleotides grown on another locus. In some instances, the loci of a device are located within a plurality of clusters. In some instances, a device comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a device comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some instances, a device comprises about 10,000 distinct loci. The amount of loci within a single cluster is varied in different instances. In some instances, each cluster includes 1, 2, 3, 4, 5, 6, 7, 8, 9, 10, 20, 30, 40, 50, 60, 70, 80, 90, 100, 120, 130, 150, 200, 300, 400, 500 or more loci. In some instances, each cluster includes about 50-500 loci. In some instances, each cluster includes about 100-200 loci. In some instances, each cluster includes about 100-150 loci. In some instances, each cluster includes about 109, 121, 130 or 137 loci. In some instances, each cluster includes about 19, 20, 61, 64 or more loci.

The number of distinct oligonucleotides synthesized on a device may be dependent on the number of distinct loci available in the substrate. In some instances, the density of loci within a cluster of a device is at least or about 1 locus per $mm^2$, 10 loci per $mm^2$, 25 loci per $mm^2$, 50 loci per $mm^2$, 65 loci per $mm^2$, 75 loci per $mm^2$, 100 loci per $mm^2$, 130 loci per $mm^2$, 150 loci per $mm^2$, 175 loci per $mm^2$, 200 loci per $mm^2$, 300 loci per $mm^2$, 400 loci per $mm^2$, 500 loci per $mm^2$, 1,000 loci per $mm^2$ or more. In some instances, a device comprises from about 10 loci per $mm^2$ to about 500 $mm^2$, from about 25 loci per $mm^2$ to about 400 $mm^2$, from about 50 loci per $mm^2$ to about 500 $mm^2$, from about 100 loci per $mm^2$ to about 500 $mm^2$, from about 150 loci per $mm^2$ to about 500 $mm^2$, from about 10 loci per $mm^2$ to about 250 $mm^2$, from about 50 loci per $mm^2$ to about 250 $mm^2$, from about 10 loci per $mm^2$ to about 200 $mm^2$, or from about 50 loci per $mm^2$ to about 200 $mm^2$. In some instances, the distance from the centers of two adjacent loci within a cluster is from about 10 um to about 500 um, from about 10 um to about 200 um, or from about 10 um to about 100 um. In some instances, the distance from two centers of adjacent loci is greater than about 10 um, 20 um, 30 um, 40 um, 50 um, 60 um, 70 um, 80 um, 90 um or 100 um. In some instances, the distance from the centers of two adjacent loci is less than about 200 um, 150 um, 100 um, 80 um, 70 urn, 60 urn, 50 urn, 40 urn, 30 urn, 20 urn or 10 urn. In some instances, each locus has a width of about 0.5 urn, 1 urn, 2 urn, 3 urn, 4 urn, 5 urn, 6 urn, 7 urn, 8 urn, 9 urn, 10 urn, 20 urn, 30 urn, 40 urn, 50 urn, 60 urn, 70 urn, 80 urn, 90 urn or 100 urn. In some instances, each locus has a width of about 0.5 urn to 100 um, about 0.5 urn to 50 urn, about 10 urn to 75 urn, or about 0.5 urn to 50 urn.

In some instances, the density of clusters within a device is at least or about 1 cluster per 100 $mm^2$, 1 cluster per 10 $mm^2$, 1 cluster per 5 $mm^2$, 1 cluster per 4 $mm^2$, 1 cluster per 3 $mm^2$, 1 cluster per 2 $mm^2$, 1 cluster per 1 $mm^2$, 2 clusters per 1 $mm^2$, 3 clusters per 1 $mm^2$, 4 clusters per 1 $mm^2$, 5 clusters per 1 $mm^2$, 10 clusters per 1 $mm^2$, 50 clusters per 1 $mm^2$ or more. In some instances, a device comprises from about 1 cluster per 10 $mm^2$ to about 10 clusters per 1 $mm^2$.

In some instances, the distance from the centers of two adjacent clusters is less than about 50 urn, 100 urn, 200 urn, 500 urn, 1000 urn, or 2000 urn or 5000 urn. In some instances, the distance from the centers of two adjacent clusters is from about 50 urn to about 100 urn, from about 50 urn to about 200 urn, from about 50 urn to about 300 urn, from about 50 urn to about 500 urn, and from about 100 urn to about 2000 urn. In some instances, the distance from the centers of two adjacent clusters is from about 0.05 mm to about 50 mm, from about 0.05 mm to about 10 mm, from about 0.05 mm to about 5 mm, from about 0.05 mm to about 4 mm, from about 0.05 mm to about 3 mm, from about 0.05 mm to about 2 mm, from about 0.1 mm to 10 mm, from about 0.2 mm to 10 mm, from about 0.3 mm to about 10 mm, from about 0.4 mm to about 10 mm, from about 0.5 mm to 10 mm, from about 0.5 mm to about 5 mm, or from about 0.5 mm to about 2 mm. In some instances, each cluster has a diameter or width along one dimension of about 0.5 to 2 mm, about 0.5 to 1 mm, or about 1 to 2 mm. In some instances, each cluster has a diameter or width along one dimension of about 0.5, 0.6, 0.7, 0.8, 0.9, 1, 1.1, 1.2, 1.3, 1.4, 1.5, 1.6, 1.7, 1.8, 1.9 or 2 mm. In some instances, each cluster has an interior diameter or width along one dimension of about 0.5, 0.6, 0.7, 0.8, 0.9, 1, 1.1, 1.15, 1.2, 1.3, 1.4, 1.5, 1.6, 1.7, 1.8, 1.9 or 2 mm.

Structures for oligonucleotide synthesis for use with devices, compositions, systems, and methods as described herein comprise a variety of sizes. A device may be about the size of a standard 96 well plate, for example from about 100 and 200 mm by about 50 and 150 mm. In some instances, a device has a diameter less than or equal to about 1000 mm, 500 mm, 450 mm, 400 mm, 300 mm, 250 nm, 200 mm, 150 mm, 100 mm or 50 mm. In some instances, the diameter of a device is from about 25 mm to 1000 mm, from about 25 mm to about 800 mm, from about 25 mm to about 600 mm, from about 25 mm to about 500 mm, from about 25 mm to about 400 mm, from about 25 mm to about 300 mm, or from about 25 mm to about 200. Non-limiting examples of device size include about 300 mm, 200 mm, 150 mm, 130 mm, 100 mm, 76 mm, 51 mm and 25 mm. In some instances, a device has a planar surface area of at least about 100 $mm^2$; 200 $mm^2$; 500 $mm^2$; 1,000 $mm^2$; 2,000 $mm^2$; 5,000 $mm^2$; 10,000 $mm^2$; 12,000 $mm^2$; 15,000 $mm^2$; 20,000 $mm^2$; 30,000 $mm^2$; 40,000 $mm^2$; 50,000 $mm^2$ or more. In some instances, the thickness of a device is from about 50 mm to about 2000 mm, from about 50 mm to about 1000 mm, from about 100 mm to about 1000 mm, from about 200 mm to about 1000 mm, or from about 250 mm to about 1000 mm Non-limiting examples of device thickness include 275 mm, 375 mm, 525 mm, 625 mm, 675 mm, 725 mm, 775 mm and 925 mm. In some instances, the thickness of a device varies with diameter and depends on the composition of the substrate. For example, a device comprising materials other than silicon has a different thickness than a silicon device of the same diameter. Device thickness may be determined by the mechanical strength of the material used and the device must be thick enough to support its own weight without cracking during handling. In some instances, a structure comprises a plurality of devices described herein.

Surface Materials

Provided herein is a device comprising a surface, wherein the surface is modified to support oligonucleotide synthesis at predetermined locations and with a resulting low error rate, a low dropout rate, a high yield, and a high oligo representation. In some embodiments, surfaces of a device for oligonucleotide synthesis provided herein are fabricated from a variety of materials capable of modification to support a de novo oligonucleotide synthesis reaction. In some cases, the devices are sufficiently conductive, e.g., are able to form uniform electric fields across all or a portion of the device. A device described herein may comprise a flexible material. Exemplary flexible materials include, without limitation, modified nylon, unmodified nylon, nitrocellulose, and polypropylene. A device described herein may comprise a rigid material. Exemplary rigid materials include, without limitation, glass, fuse silica, silicon, silicon dioxide, silicon nitride, plastics (for example, polytetrafluoroethylene, polypropylene, polystyrene, polycarbonate, and blends thereof, and metals (for example, gold, platinum). Devices disclosed herein may be fabricated from a material comprising silicon, polystyrene, agarose, dextran, cellulosic polymers, polyacrylamides, polydimethylsiloxane (PDMS), glass, or any combination thereof. In some cases, a device disclosed herein is manufactured with a combination of materials listed herein or any other suitable material known in the art.

In some cases, a device disclosed herein comprises a silicon dioxide base and a surface layer of silicon oxide. Alternatively, the device may have a base of silicon oxide. A surface of the device provided here may be textured, resulting in an increase in overall surface area for oligonucleotide synthesis. Devices disclosed herein may comprise at least 5%, 10%, 25%, 50%, 80%, 90%, 95%, or 99% silicon. A device disclosed herein may be fabricated from a silicon on insulator (SOI) wafer.

Substrates, devices and reactors provided herein are fabricated from any variety of materials suitable for the methods and compositions described herein. In certain instances, device materials are fabricated to exhibit a low level of nucleotide binding. In some instances, device materials are modified to generate distinct surfaces that exhibit a high level of nucleotide binding. In some instances, device materials are transparent to visible and/or UV light. In some instances, device materials are sufficiently conductive, e.g., are able to form uniform electric fields across all or a portion of a substrate. In some instances, conductive materials are connected to an electric ground. In some instances, the device is heat conductive or insulated. In some instances, the materials are chemical resistant and heat resistant to support chemical or biochemical reactions, for example oligonucleotide synthesis reaction processes. In some instances, a device comprises flexible materials. Flexible materials include, without limitation, modified nylon, unmodified nylon, nitrocellulose, polypropylene, and the like. In some instances, a device comprises rigid materials. Rigid materials include, without limitation, glass, fuse silica, silicon, silicon dioxide, silicon nitride, plastics (for example, polytetraflouroethylene, polypropylene, polystyrene, polycarbonate, and blends thereof, and the like), and metals (for example, gold, platinum, and the like). In some instances, a device is fabricated from a material comprising silicon, polystyrene, agarose, dextran, cellulosic polymers, polyacrylamides, polydimethylsiloxane (PDMS), glass, or any combination thereof. In some instances, a device is manufactured with a combination of materials listed herein or any other suitable material known in the art.

Surface Architecture

Provided herein are devices comprising raised and/or lowered features. One benefit of having such features is an increase in surface area to support oligonucleotide synthesis. In some instances, a device having raised and/or lowered features is referred to as a three-dimensional substrate. In some instances, a three-dimensional device comprises one or more channels. In some instances, one or more loci comprise a channel. In some instances, the channels are accessible to reagent deposition via a deposition device such as an oligonucleotide synthesizer. In some instances, reagents and/or fluids collect in a larger well in fluid communication with one or more channels. For example, a device comprises a plurality of channels corresponding to a plurality of loci with a cluster, and the plurality of channels are in fluid communication with one well of the cluster. In some methods, a library of oligonucleotides is synthesized in a plurality of loci of a cluster.

In some instances, the structure is configured to allow for controlled flow and mass transfer paths for oligonucleotide synthesis on a surface. In some instances, the configuration of a device allows for the controlled and even distribution of mass transfer paths, chemical exposure times, and/or wash efficacy during oligonucleotide synthesis. In some instances, the configuration of a device allows for increased sweep efficiency, for example by providing sufficient volume for growing an oligonucleotide such that the excluded volume by the growing oligonucleotide does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the oligonucleotide. In some instances, a three-dimensional structure allows for managed flow of fluid to allow for the rapid exchange of chemical exposure.

Provided herein are methods to synthesize an amount of DNA of 1 fM, 5 fM, 10 fM, 25 fM, 50 fM, 75 fM, 100 fM, 200 fM, 300 fM, 400 fM, 500 fM, 600 fM, 700 fM, 800 fM, 900 fM, 1 pM, 5 pM, 10 pM, 25 pM, 50 pM, 75 pM, 100 pM, 200 pM, 300 pM, 400 pM, 500 pM, 600 pM, 700 pM, 800 pM, 900 pM, or more. In some instances, an oligonucleotide library may span the length of about 1%, 2%, 3%, 4%, 5%, 10%, 15%, 20%, 30%, 40%, 50%, 60%, 70%, 80%, 90%, 95%, or 100% of a gene. A gene may be varied up to about 1%, 2%, 3%, 4%, 5%, 10%, 15%, 20%, 30%, 40%, 50%, 60%, 70%, 80%, 85%, 90%, 95%, or 100%.

Non-identical oligonucleotides may collectively encode a sequence for at least 1%, 2%, 3%, 4%, 5%, 10%, 15%, 20%, 30%, 40%, 50%, 60%, 70%, 80%, 85%, 90%, 95%, or 100% of a gene. In some instances, an oligonucleotide may encode a sequence of 50%, 60%, 70%, 80%, 85%, 90%, 95%, or more of a gene. In some instances, an oligonucleotide may encode a sequence of 80%, 85%, 90%, 95%, or more of a gene.

In some instances, segregation is achieved by physical structure. In some instances, segregation is achieved by differential functionalization of the surface generating active and passive regions for oligonucleotide synthesis. Differential functionalization is also achieved by alternating the hydrophobicity across the device surface, thereby creating water contact angle effects that cause beading or wetting of the deposited reagents. Employing larger structures may decrease splashing and cross-contamination of distinct oligonucleotide synthesis locations with reagents of the neighboring spots. In some instances, a device, such as an oligonucleotide synthesizer, is used to deposit reagents to distinct oligonucleotide synthesis locations. Substrates having three-dimensional features are configured in a manner that allows for the synthesis of a large number of oligonucleotides (e.g., more than about 10,000) with a low error rate (e.g., less than about 1:500, 1:1000, 1:1500, 1:2,000; 1:3,000; 1:5,000; or 1:10,000). In some instances, a device comprises features with a density of about or greater than about 1, 5, 10, 20, 30, 40, 50, 60, 70, 80, 90, 100, 110, 120, 130, 140, 150, 160, 170, 180, 190, 200, 300, 400 or 500 features per $mm^2$.

A well of a device may have the same or different width, height, and/or volume as another well of the substrate. A channel of a device may have the same or different width, height, and/or volume as another channel of the substrate. In some instances, the width of a cluster is from about 0.05 mm to about 50 mm, from about 0.05 mm to about 10 mm, from about 0.05 mm to about 5 mm, from about 0.05 mm to about 4 mm, from about 0.05 mm to about 3 mm, from about 0.05 mm to about 2 mm, from about 0.05 mm to about 1 mm, from about 0.05 mm to about 0.5 mm, from about 0.05 mm to about 0.1 mm, from about 0.1 mm to 10 mm, from about 0.2 mm to about 10 mm, from about 0.3 mm to about 10 mm, from about 0.4 mm to about 10 mm, from about 0.5 mm to about 10 mm, from about 0.5 mm to about 5 mm, or from about 0.5 mm to about 2 mm. In some instances, the width of a well comprising a cluster is from about 0.05 mm to about 50 mm, from about 0.05 mm to about 10 mm, from about 0.05 mm to about 5 mm, from about 0.05 mm to about 4 mm, from about 0.05 mm to about 3 mm, from about 0.05 mm to about 2 mm, from about 0.05 mm to about 1 mm, from about 0.05 mm to about 0.5 mm, from about 0.05 mm to about 0.1 mm, from about 0.1 mm to about 10 mm, from about 0.2 mm to about 10 mm, from about 0.3 mm to about 10 mm, from about 0.4 mm to about 10 mm, from about 0.5 mm to about 10 mm, from about 0.5 mm to about 5 mm, or from about 0.5 mm to about 2 mm. In some instances, the width of a cluster is less than or about 5 mm, 4 mm, 3 mm, 2 mm, 1 mm, 0.5 mm, 0.1 mm, 0.09 mm, 0.08 mm, 0.07 mm, 0.06 mm or 0.05 mm. In some instances, the width of a cluster is from about 1.0 to about 1.3 mm. In some instances, the width of a cluster is about 1.150 mm. In some instances, the width of a well is less than or about 5 mm, 4 mm, 3 mm, 2 mm, 1 mm, 0.5 mm, 0.1 mm, 0.09 mm, 0.08 mm, 0.07 mm, 0.06 mm or 0.05 mm. In some instances, the width of a well is from about 1.0 to about 1.3 mm. In some instances, the width of a well is about 1.150 mm. In some instances, the width of a cluster is about 0.08 mm. In some instances, the width of a well is about 0.08 mm. The width of a cluster may refer to clusters within a two-dimensional or three-dimensional substrate.

In some instances, the height of a well is from about 20 um to about 1000 um, from about 50 um to about 1000 um, from about 100 um to about 1000 um, from about 200 um to about 1000 um, from about 300 um to about 1000 um, from about 400 um to about 1000 um, or from about 500 um to about 1000 um. In some instances, the height of a well is less than about 1000 um, less than about 900 um, less than about 800 um, less than about 700 um, or less than about 600 um.

In some instances, a device comprises a plurality of channels corresponding to a plurality of loci within a cluster, wherein the height or depth of a channel is from about 5 um to about 500 um, from about 5 um to about 400 um, from about 5 um to about 300 um, from about 5 um to about 200 um, from about 5 um to about 100 um, from about 5 um to about 50 um, or from about 10 um to about 50 um. In some instances, the height of a channel is less than 100 um, less than 80 um, less than 60 um, less than 40 um or less than 20 um.

In some instances, the diameter of a channel, locus (e.g., in a substantially planar substrate) or both channel and locus (e.g., in a three-dimensional device wherein a locus corresponds to a channel) is from about 1 um to about 1000 um, from about 1 um to about 500 um, from about 1 um to about 200 um, from about 1 um to about 100 um, from about 5 um to about 100 um, or from about 10 um to about 100 um, for example, about 90 um, 80 um, 70 um, 60 um, 50 um, 40 um, 30 um, 20 um or 10 um. In some instances, the diameter of a channel, locus, or both channel and locus is less than about 100 um, 90 um, 80 um, 70 um, 60 um, 50 um, 40 um, 30 um, 20 um or 10 um. In some instances, the distance from the center of two adjacent channels, loci, or channels and loci is from about 1 um to about 500 um, from about 1 um to about 200 um, from about 1 um to about 100 um, from about 5 um to about 200 um, from about 5 um to about 100 um, from about 5 um to about 50 um, or from about 5 um to about 30 um, for example, about 20 um.

Surface Modifications

In various instances, surface modifications are employed for the chemical and/or physical alteration of a surface by an additive or subtractive process to change one or more chemical and/or physical properties of a device surface or a selected site or region of a device surface. For example, surface modifications include, without limitation, (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

In some instances, the addition of a chemical layer on top of a surface (referred to as an adhesion promoter) facilitates structured patterning of loci on a surface of a substrate. Exemplary surfaces for application of adhesion promotion include, without limitation, glass, silicon, silicon dioxide and silicon nitride. In some instances, the adhesion promoter is a chemical with a high surface energy. In some instances, a second chemical layer is deposited on a surface of a substrate. In some instances, the second chemical layer has a low surface energy. In some instances, surface energy of a chemical layer coated on a surface supports localization of droplets on the surface. Depending on the patterning arrangement selected, the proximity of loci and/or area of fluid contact at the loci are alterable.

In some instances, a device surface, or resolved loci, onto which nucleic acids or other moieties are deposited, e.g., for oligonucleotide synthesis, are smooth or substantially planar (e.g., two-dimensional) or have irregularities, such as raised or lowered features (e.g., three-dimensional features). In some instances, a device surface is modified with one or more different layers of compounds. Such modification layers of interest include, without limitation, inorganic and organic layers such as metals, metal oxides, polymers, small organic molecules and the like. Non-limiting polymeric layers include peptides, proteins, nucleic acids or mimetics thereof (e.g., peptide nucleic acids and the like), polysaccharides, phospholipids, polyurethanes, polyesters, polycarbonates, polyureas, polyamides, polyetheyleneamines, polyarylene sulfides, polysiloxanes, polyimides, polyacetates, and any other suitable compounds described herein or otherwise known in the art. In some instances, polymers are heteropolymeric. In some instances, polymers are homopolymeric. In some instances, polymers comprise functional moieties or are conjugated.

In some instances, resolved loci of a device are functionalized with one or more moieties that increase and/or decrease surface energy. In some instances, a moiety is chemically inert. In some instances, a moiety is configured to support a desired chemical reaction, for example, one or more processes in an oligonucleotide synthesis reaction. The surface energy, or hydrophobicity, of a surface is a factor for determining the affinity of a nucleotide to attach onto the surface. In some instances, a method for device functionalization may comprise: (a) providing a device having a surface that comprises silicon dioxide; and (b) silanizing the surface using, a suitable silanizing agent described herein or otherwise known in the art, for example, an organofunctional alkoxysilane molecule.

In some instances, the organofunctional alkoxysilane molecule comprises dimethylchloro-octodecyl-silane, methyldichloro-octodecyl-silane, trichloro-octodecyl-silane, trimethyl-octodecyl-silane, triethyl-octodecyl-silane, or any combination thereof. In some instances, a device surface comprises functionalized with polyethylene/polypropylene (functionalized by gamma irradiation or chromic acid oxidation, and reduction to hydroxyalkyl surface), highly cross-linked polystyrene-divinylbenzene (derivatized by chloromethylation, and aminated to benzylamine functional surface), nylon (the terminal aminohexyl groups are directly reactive), or etched with reduced polytetrafluoroethylene. Other methods and functionalizing agents are described in U.S. Pat. No. 5,474,796, which is herein incorporated by reference in its entirety.

In some instances, a device surface is functionalized by contact with a derivatizing composition that contains a mixture of silanes, under reaction conditions effective to couple the silanes to the device surface, typically via reactive hydrophilic moieties present on the device surface. Silanization generally covers a surface through self-assembly with organofunctional alkoxysilane molecules.

A variety of siloxane functionalizing reagents may further be used as currently known in the art, e.g., for lowering or increasing surface energy. The organofunctional alkoxysilanes may be classified according to their organic functions.

Provided herein are devices that may contain patterning of agents capable of coupling to a nucleoside. In some instances, a device may be coated with an active agent. In some instances, a device may be coated with a passive agent. Exemplary active agents for inclusion in coating materials described herein include, without limitation, N-(3-triethoxysilylpropyl)-4-hydroxybutyramide (HAPS), 11-acetoxyundecyltriethoxysilane, n-decyltriethoxysilane, (3-aminopropyl)trimethoxysilane, (3-aminopropyl)triethoxysilane, 3-glycidoxypropyltrimethoxysilane (GOPS), 3-iodo-propyltrimethoxysilane, butyl-aldehydr-trimethoxysilane, dimeric secondary aminoalkyl siloxanes, (3-aminopropyl)-diethoxy-methylsilane, (3-aminopropyl)-dimethyl-ethoxysilane, and (3-aminopropyl)-trimethoxysilane, (3-glycidoxypropyl)-dimethyl-ethoxysilane, glycidoxy-trimethoxysilane, (3-mercaptopropyl)-trimethoxysilane, 3-4 epoxycyclohexyl-ethyl-trimethoxysilane, and (3-mercaptopropyl)-methyl-dimethoxysilane, allyl trichlorochlorosilane, 7-oct-1-enyl trichlorochlorosilane, or bis (3-trimethoxysilylpropyl) amine.

Exemplary passive agents for inclusion in a coating material described herein include, without limitation, perfluorooctyltrichlorosilane; tridecafluoro-1, 1,2,2-tetrahydrooctyl)trichlorosilane; 1H, 1H, 2H, 2H-fluorooctyltriethoxysilane (FOS); trichloro(1H, 1H, 2H, 2H-perfluorooctyl)silane; tert-butyl-[5-fluoro-4-(4,4,5,5-tetramethyl-1,3,2-dioxaborolan-2-yl)indol-1-yl]-dimethyl-silane; CYTOP™; Fluorinert™; perfluoroctyltrichlorosilane (PFOTCS); perfluorooctyldimethylchlorosilane (PFODCS); perfluorodecyltriethoxysilane (PFDTES); pentafluorophenyl-dimethylpropylchloro-silane (PFPTES); perfluorooctyl-triethoxysilane; perfluorooctyltrimethoxysilane; octylchlorosilane; dimethylchloro-octodecyl-silane; methyldichloro-octodecyl-silane; trichloro-octodecyl-silane; trimethyl-octodecyl-silane; triethyl-octodecyl-silane; or octadecyltrichlorosilane.

In some instances, a functionalization agent comprises a hydrocarbon silane such as octadecyltrichlorosilane. In some instances, the functionalizing agent comprises 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide.

Oligonucleotide Synthesis

Methods of the current disclosure for oligonucleotide synthesis may include processes involving phosphoramidite chemistry. In some instances, oligonucleotide synthesis comprises coupling a base with phosphoramidite. Oligonucleotide synthesis may comprise coupling a base by deposition of phosphoramidite under coupling conditions, wherein the same base is optionally deposited with phosphoramidite more than once, i.e., double coupling. Oligonucleotide synthesis may comprise capping of unreacted sites. In some instances, capping is optional. Oligonucleotide synthesis may also comprise oxidation or an oxidation step or oxidation steps. Oligonucleotide synthesis may comprise deblocking, detritylation, and sulfurization. In some instances, oligonucleotide synthesis comprises either oxidation or sulfurization. In some instances, between one or each step during an oligonucleotide synthesis reaction, the device is washed, for example, using tetrazole or acetonitrile. Time frames for any one step in a phosphoramidite synthesis method may be less than about 2 min, 1 min, 50 sec, 40 sec, 30 sec, 20 sec and 10 sec.

Oligonucleotide synthesis using a phosphoramidite method may comprise a subsequent addition of a phosphoramidite building block (e.g., nucleoside phosphoramidite) to a growing oligonucleotide chain for the formation of a phosphite triester linkage. Phosphoramidite oligonucleotide synthesis proceeds in the 3' to 5' direction. Phosphoramidite oligonucleotide synthesis allows for the controlled addition of one nucleotide to a growing nucleic acid chain per synthesis cycle. In some instances, each synthesis cycle comprises a coupling step. Phosphoramidite coupling involves the formation of a phosphite triester linkage between an activated nucleoside phosphoramidite and a nucleoside bound to the substrate, for example, via a linker. In some instances, the nucleoside phosphoramidite is provided to the device activated. In some instances, the nucleoside phosphoramidite is provided to the device with an activator. In some instances, nucleoside phosphoramidites are provided to the device in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition of a nucleoside phosphoramidite, the device is optionally washed. In some instances, the coupling step is repeated one or more additional times, optionally with a wash step between nucleoside phosphoramidite additions to the substrate. In some instances, an oligonucleotide synthesis method used herein comprises 1, 2, 3 or more sequential coupling steps. Prior to coupling, in many cases, the nucleoside bound to the device is de-protected by removal of a protecting group, where the protecting group functions to prevent polymerization. A common protecting group is 4,4'-dimethoxytrityl (DMT).

Following coupling, phosphoramidite oligonucleotide synthesis methods optionally comprise a capping step. In a capping step, the growing oligonucleotide is treated with a capping agent. A capping step is useful to block unreacted substrate-bound 5'—OH groups after coupling from further chain elongation, preventing the formation of oligonucleotides with internal base deletions. Further, phosphoramidites activated with 1H-tetrazole may react, to a small extent, with the O6 position of guanosine. Without being bound by theory, upon oxidation with $I_2$/water, this side product, possibly via O6-N7 migration, may undergo depurination. The apurinic sites may end up being cleaved in the course of the final deprotection of the oligonucleotide thus reducing the yield of the full-length product. The O6 modifications may be removed by treatment with the capping reagent prior to oxidation with $I_2$/water. In some instances, inclusion of a capping step during oligonucleotide synthesis decreases the error rate as compared to synthesis without capping. As an example, the capping step comprises treating the substrate-bound oligonucleotide with a mixture of acetic anhydride and 1-methylimidazole. Following a capping step, the device is optionally washed.

In some instances, following addition of a nucleoside phosphoramidite, and optionally after capping and one or more wash steps, the device bound growing oligonucleotide is oxidized. The oxidation step comprises the phosphite triester is oxidized into a tetracoordinated phosphate triester, a protected precursor of the naturally occurring phosphate diester internucleoside linkage. In some instances, oxidation of the growing oligonucleotide is achieved by treatment with iodine and water, optionally in the presence of a weak base (e.g., pyridine, lutidine, collidine). Oxidation may be carried out under anhydrous conditions using, e.g. tert-Butyl hydroperoxide or (1S)-(+)-(10-camphorsulfonyl)-oxaziridine (CSO). In some methods, a capping step is performed following oxidation. A second capping step allows for device drying, as residual water from oxidation that may persist may inhibit subsequent coupling. Following oxidation, the device and growing oligonucleotide is optionally washed. In some instances, the step of oxidation is substituted with a sulfurization step to obtain oligonucleotide phosphorothioates, wherein any capping steps may be performed after the sulfurization. Many reagents are capable of the efficient sulfur transfer, including but not limited to 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, the protected 5' end of the device bound growing oligonucleotide is removed so that the primary hydroxyl group is reactive with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound oligonucleotide and thus reduces the yield of the desired full-length product. Methods and compositions of the disclosure described herein provide for controlled deblocking conditions limiting undesired depurination reactions. In some instances, the device bound oligonucleotide is washed after deblocking. In some instances, efficient washing after deblocking contributes to synthesized oligonucleotides having a low error rate.

Methods for the synthesis of oligonucleotides typically involve an iterating sequence of the following steps: application of a protected monomer to an actively functionalized surface (e.g., locus) to link with either the activated surface, a linker or with a previously deprotected monomer; deprotection of the applied monomer so that it is reactive with a subsequently applied protected monomer; and application of another protected monomer for linking. One or more intermediate steps include oxidation or sulfurization. In some instances, one or more wash steps precede or follow one or all of the steps.

Methods for phosphoramidite-based oligonucleotide synthesis comprise a series of chemical steps. In some instances, one or more steps of a synthesis method involve reagent cycling, where one or more steps of the method comprise application to the device of a reagent useful for the step. For example, reagents are cycled by a series of liquid deposition and vacuum drying steps. For substrates comprising three-dimensional features such as wells, microwells, channels and the like, reagents are optionally passed through one or more regions of the device via the wells and/or channels.

Methods and systems described herein relate to oligonucleotide synthesis devices for the synthesis of oligonucleotides. The synthesis may be in parallel. For example, at least or about at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 100, 150, 200, 250, 300, 350, 400, 450, 500, 550, 600, 650, 700, 750, 800, 850, 900, 1000, 10000, 50000, 75000, 100000 or more oligonucleotides may be synthesized in parallel. The total number oligonucleotides that may be synthesized in parallel may be from 2-100000, 3-50000, 4-10000, 5-1000, 6-900, 7-850, 8-800, 9-750, 10-700, 11-650, 12-600, 13-550, 14-500, 15-450, 16-400, 17-350, 18-300, 19-250, 20-200, 21-150, 22-100, 23-50, 24-45, 25-40, 30-35. Those of skill in the art appreciate that the total number of oligonucleotides synthesized in parallel may fall within any range bound by any of these values, for example 25-100. The total number of oligonucleotides synthesized in parallel may fall within any range defined by any of the values serving as endpoints of the range. Total molar mass of oligonucleotides synthesized within the device or the molar mass of each of the oligonucleotides may be at least or at least about 10, 20, 30, 40, 50, 100, 250, 500, 750, 1000, 2000, 3000, 4000, 5000, 6000, 7000, 8000, 9000, 10000, 25000, 50000, 75000, 100000 picomoles, or more. The length of each of the oligonucleotides or average length of the oligonucleotides within the device may be at least or about at least 10, 15, 20, 25, 30, 35, 40, 45, 50, 100, 150, 200, 300, 400, 500 nucleotides, or more. The length of each of the oligonucleotides or average length of the oligonucleotides within the device may be at most or about at most 500, 400, 300, 200, 150, 100, 50, 45, 35, 30, 25, 20, 19, 18, 17, 16, 15, 14, 13, 12, 11, 10 nucleotides, or less. The length of each of the oligonucleotides or average length of the oligonucleotides within the device may fall from 10-500, 9-400, 11-300, 12-200, 13-150, 14-100, 15-50, 16-45, 17-40, 18-35, 19-25. Those of skill in the art appreciate that the length of each of the oligonucleotides or average length of the oligonucleotides within the device may fall within any range bound by any of these values, for example 100-300. The length of each of the oligonucleotides or average length of the oligonucleotides within the device may fall within any range defined by any of the values serving as endpoints of the range.

Methods for oligonucleotide synthesis on a surface provided herein allow for synthesis at a fast rate. As an example, at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more are synthesized. Nucleotides include adenine, guanine, thymine, cytosine, uridine building blocks, or analogs/modified versions thereof. In some instances, libraries of oligonucleotides are synthesized in parallel on a substrate. For example, a device comprising about or at least about 100; 1,000; 10,000; 30,000; 75,000; 100,000; 1,000,000; 2,000,000; 3,000,000; 4,000,000; or 5,000,000 resolved loci is able to support the synthesis of at least the same number of distinct oligonucleotides, wherein each oligonucleotide encoding a distinct sequence is synthesized on a resolved locus. In some instances, a library of oligonucleotides is synthesized on a device with low error rates described herein in less than about three months, two months, one month, three weeks, 15, 14, 13, 12, 11, 10, 9, 8, 7, 6, 5, 4, 3, 2 days, 24 hours or less. In some instances, larger nucleic acids assembled from an oligonucleotide library synthesized with a low error rate using the substrates and methods described herein are prepared in less than about three months, two months, one month, three weeks, 15, 14, 13, 12, 11, 10, 9, 8, 7, 6, 5, 4, 3, 2 days, 24 hours or less.

In some instances, methods described herein provide for generation of a library of oligonucleotides comprising variant oligonucleotides differing at a plurality of codon sites. In some instances, an oligonucleotide may have 1 site, 2 sites, 3 sites, 4 sites, 5 sites, 6 sites, 7 sites, 8 sites, 9 sites, 10 sites, 11 sites, 12 sites, 13 sites, 14 sites, 15 sites, 16 sites, 17 sites 18 sites, 19 sites, 20 sites, 30 sites, 40 sites, 50 sites, or more of variant codon sites.

In some instances, the one or more sites of variant codon sites may be adjacent. In some instances, the one or more sites of variant codon sites may not be adjacent and separated by 1, 2, 3, 4, 5, 6, 7, 8, 9, 10, or more codons.

In some instances, an oligonucleotide may comprise multiple sites of variant codon sites, wherein all the variant codon sites are adjacent to one another, forming a stretch of variant codon sites. In some instances, an oligonucleotide may comprise multiple sites of variant codon sites, wherein none the variant codon sites are adjacent to one another. In some instances, an oligonucleotide may comprise multiple sites of variant codon sites, wherein some the variant codon sites are adjacent to one another, forming a stretch of variant codon sites, and some of the variant codon sites are not adjacent to one another.

Figure 12:
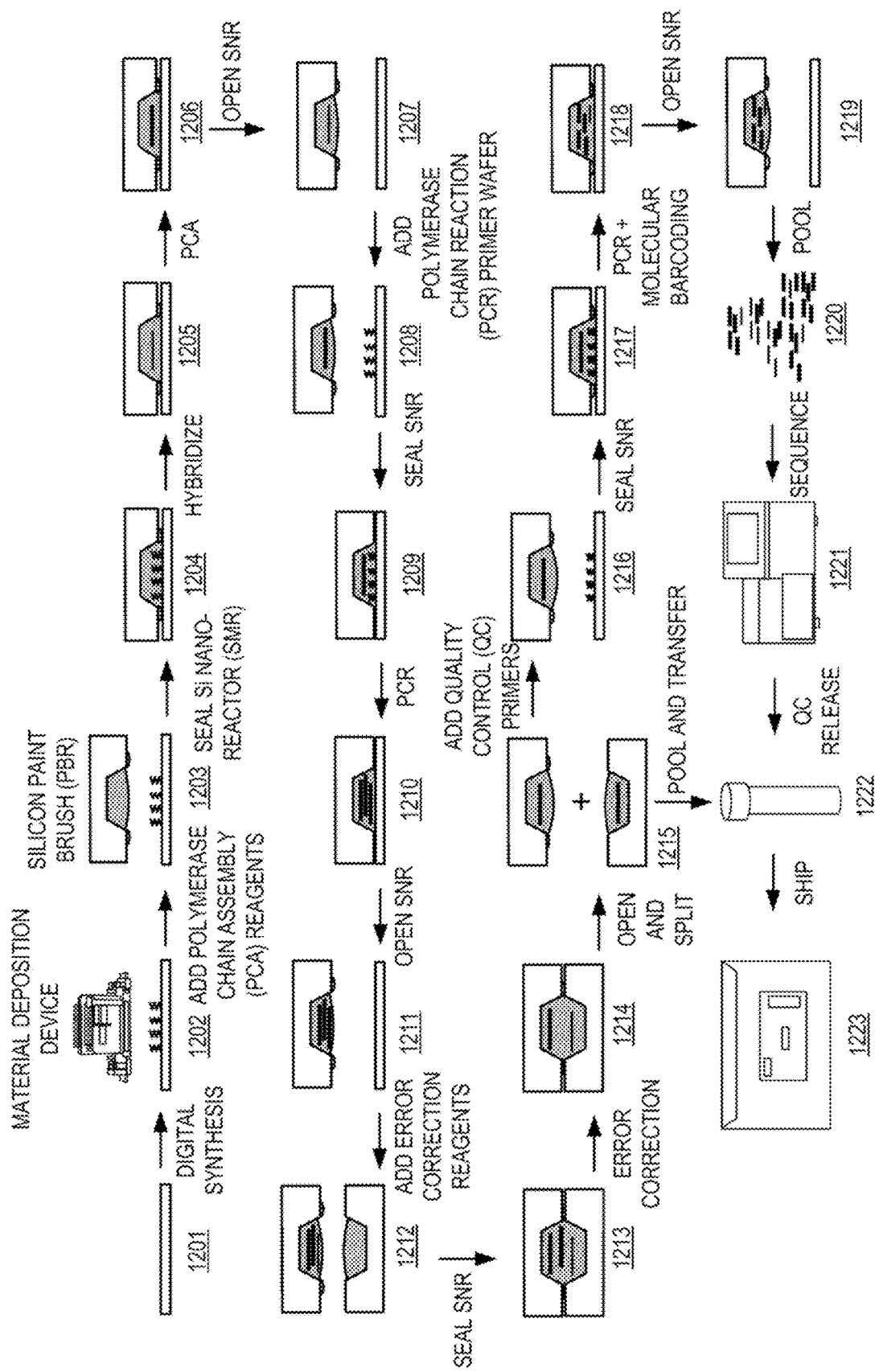
FIG. 12 presents a diagram of steps demonstrating an exemplary process workflow for gene synthesis as disclosed herein.

Referring to the Figures, FIG. 12 illustrates an exemplary process workflow for synthesis of nucleic acids (e.g., genes) from shorter oligonucleotides. The workflow is divided generally into phases: (1) de novo synthesis of a single stranded oligonucleotide library, (2) joining oligonucleotides to form larger fragments, (3) error correction, (4) quality control, and (5) shipment. Prior to de novo synthesis, an intended nucleic acid sequence or group of nucleic acid sequences is preselected. For example, a group of genes is preselected for generation.

Once large oligonucleotides for generation are selected, a predetermined library of oligonucleotides is designed for de novo synthesis. Various suitable methods are known for generating high density oligonucleotide arrays. In the workflow example, a device surface layer 1201 is provided. In the example, chemistry of the surface is altered in order to improve the oligonucleotide synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of oligonucleotide arrays is generated on a solid support and utilizes single nucleotide extension process to extend multiple oligomers in parallel. A material deposition device, such as an oligonucleotide synthesizer, is designed to release reagents in a step wise fashion such that multiple oligonucleotides extend, in parallel, one residue at a time to generate oligomers with a predetermined nucleic acid sequence 1202. In some instances, oligonucleotides are cleaved from the surface at this stage. Cleavage includes gas cleavage, e.g., with ammonia or methylamine.

The generated oligonucleotide libraries are placed in a reaction chamber. In this exemplary workflow, the reaction chamber (also referred to as "nanoreactor") is a silicon coated well, containing PCR reagents and lowered onto the oligonucleotide library 1203. Prior to or after the sealing 1204 of the oligonucleotides, a reagent is added to release the oligonucleotides from the substrate. In the exemplary workflow, the oligonucleotides are released subsequent to sealing of the nanoreactor 1205. Once released, fragments of single stranded oligonucleotides hybridize in order to span an entire long range sequence of DNA. Partial hybridization 1205 is possible because each synthesized oligonucleotide is designed to have a small portion overlapping with at least one other oligonucleotide in the pool.

After hybridization, a PCA reaction is commenced. During the polymerase cycles, the oligonucleotides anneal to complementary fragments and gaps are filled in by a polymerase. Each cycle increases the length of various fragments randomly depending on which oligonucleotides find each other. Complementarity amongst the fragments allows for forming a complete large span of double stranded DNA 1206.

After PCA is complete, the nanoreactor is separated from the device 1207 and positioned for interaction with a device having primers for PCR 1208. After sealing, the nanoreactor is subject to PCR 1209 and the larger nucleic acids are amplified. After PCR 1210, the nanochamber is opened 1211, error correction reagents are added 1212, the chamber is sealed 1213 and an error correction reaction occurs to remove mismatched base pairs and/or strands with poor complementarity from the double stranded PCR amplification products 1214. The nanoreactor is opened and separated 1215. Error corrected product is next subject to additional processing steps, such as PCR and molecular bar coding, and then packaged 1222 for shipment 1223.

In some instances, quality control measures are taken. After error correction, quality control steps include for example interaction with a wafer having sequencing primers for amplification of the error corrected product 1216, sealing the wafer to a chamber containing error corrected amplification product 1217, and performing an additional round of amplification 1218. The nanoreactor is opened 1219 and the products are pooled 1220 and sequenced 1221. After an acceptable quality control determination is made, the packaged product 1222 is approved for shipment 1223.

In some instances, a nucleic acid generated by a workflow such as that in FIG. 12 is subject to mutagenesis using overlapping primers disclosed herein. In some instances, a library of primers is generated by in situ preparation on a solid support and utilize single nucleotide extension process to extend multiple oligomers in parallel. A deposition device, such as an oligonucleotide synthesizer, is designed to release reagents in a step wise fashion such that multiple oligonucleotides extend, in parallel, one residue at a time to generate oligomers with a predetermined nucleic acid sequence 1202.

Computer Systems

Any of the systems described herein, may be operably linked to a computer and may be automated through a computer either locally or remotely. In various instances, the methods and systems of the disclosure may further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the disclosure. The computer systems may be programmed to interface between the user specified base sequence and the position of a material deposition device to deliver the correct reagents to specified regions of the substrate.

Figure 13:
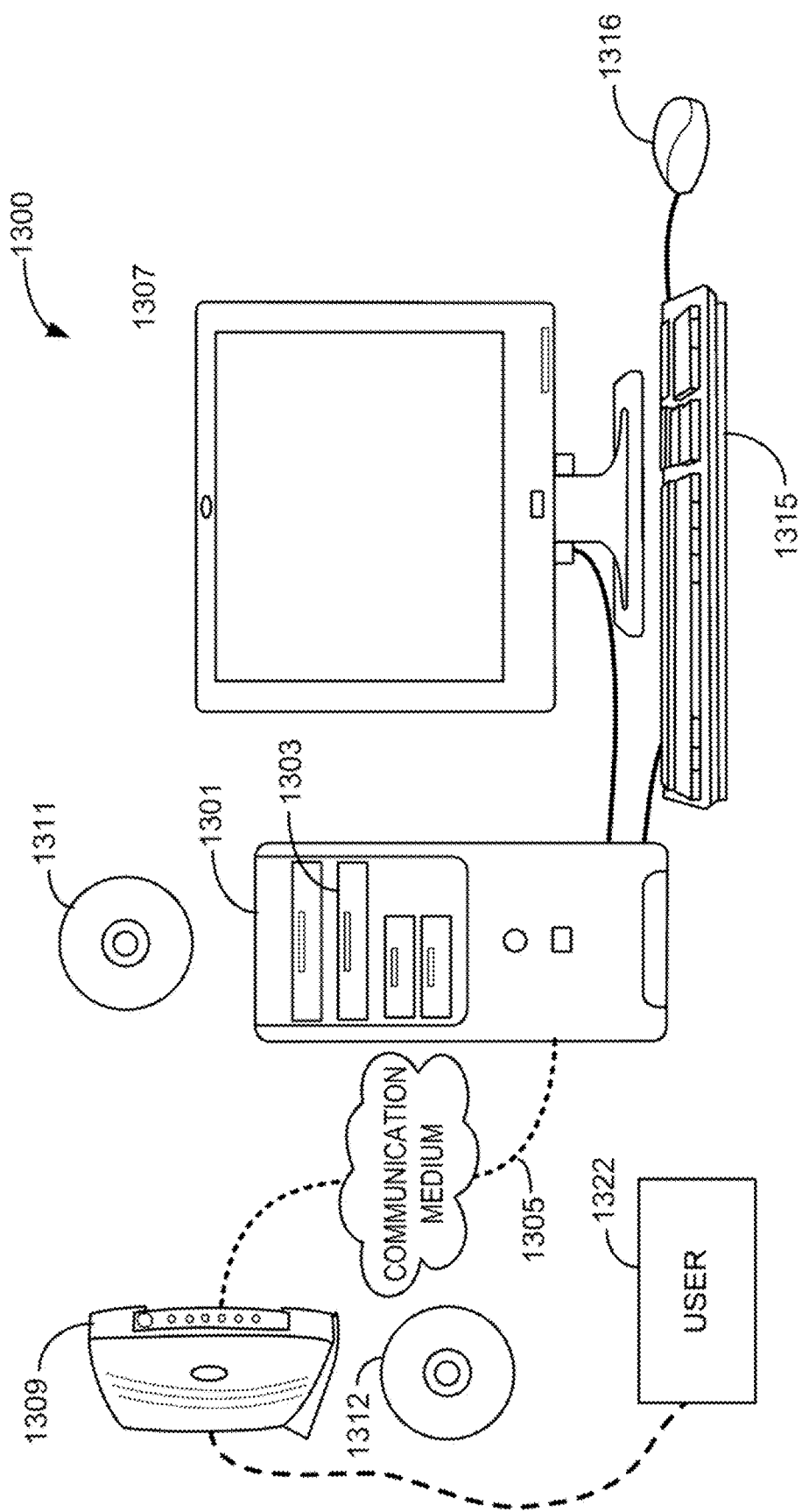
FIG. 13 illustrates an example of a computer system.

The computer system 1300 illustrated in FIG. 13 may be understood as a logical apparatus that can read instructions from media 1311 and/or a network port 1305, which can optionally be connected to server 1309 having fixed media 1312. The system, such as shown in FIG. 13 can include a CPU 1301, disk drives 1303, optional input devices such as keyboard 1315 and/or mouse 1316 and optional monitor 1307. Data communication may be achieved through the indicated communication medium to a server at a local or a remote location. The communication medium may include any means of transmitting and/or receiving data. For example, the communication medium may be a network connection, a wireless connection or an internet connection. Such a connection may provide for communication over the World Wide Web. It is envisioned that data relating to the present disclosure may be transmitted over such networks or connections for reception and/or review by a party 1322 as illustrated in FIG. 13.

Figure 14:
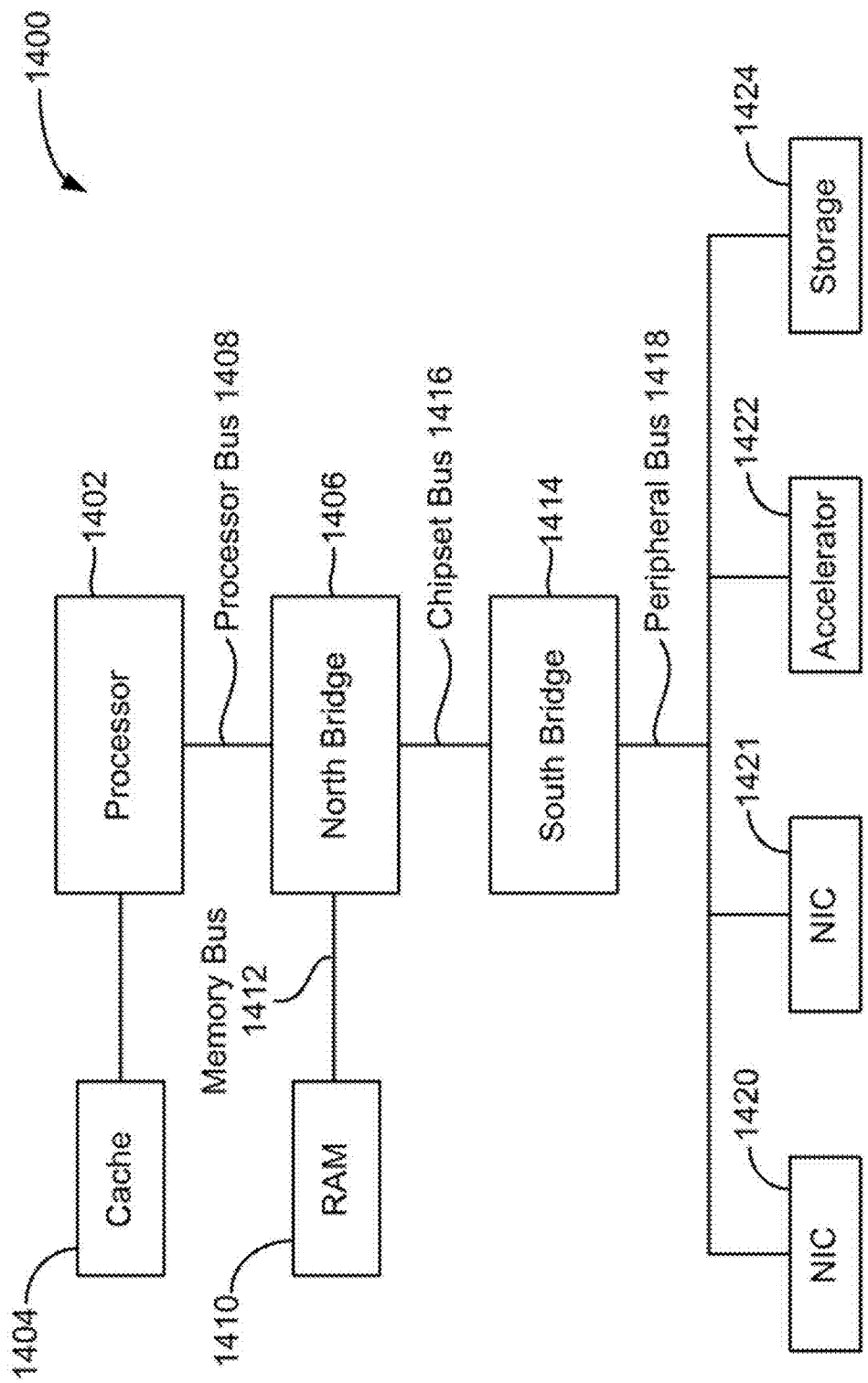
FIG. 14 is a block diagram illustrating an architecture of a computer system.

FIG. 14 is a block diagram illustrating a first example architecture of a computer system 1400 that may be used in connection with example instances of the present disclosure. As depicted in FIG. 14, the example computer system may include a processor 1402 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution may be used for parallel processing. In some instances, multiple processors or processors with multiple cores may also be used, whether in a single computer system, in a cluster, or distributed across systems over a network comprising a plurality of computers, cell phones, and/or personal data assistant devices.

As illustrated in FIG. 14, a high speed cache 1404 may be connected to, or incorporated in, the processor 1402 to provide a high speed memory for instructions or data that have been recently, or are frequently, used by processor 1402. The processor 1402 is connected to a north bridge 1406 by a processor bus 1408. The north bridge 1406 is connected to random access memory (RAM) 1410 by a memory bus 1412 and manages access to the RAM 1410 by the processor 1402. The north bridge 1406 is also connected to a south bridge 1414 by a chipset bus 1416. The south bridge 1414 is, in turn, connected to a peripheral bus 1418. The peripheral bus may be, for example, PCI, PCI-X, PCI Express, or other peripheral bus. The north bridge and south bridge are often referred to as a processor chipset and manage data transfer between the processor, RAM, and peripheral components on the peripheral bus 1418. In some alternative architectures, the functionality of the north bridge may be incorporated into the processor instead of using a separate north bridge chip. In some instances, system 1400 may include an accelerator card 1422 attached to the peripheral bus 1418. The accelerator may include field programmable gate arrays (FPGAs) or other hardware for accelerating certain processing. For example, an accelerator may be used for adaptive data restructuring or to evaluate algebraic expressions used in extended set processing.

Software and data are stored in external storage 1424 and may be loaded into RAM 1410 and/or cache 1404 for use by the processor. The system 1400 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example instances of the present disclosure. In this example, system 1400 also includes network interface cards (NICs) 1420 and 1421 connected to the peripheral bus for providing network interfaces to external storage, such as Network Attached Storage (NAS) and other computer systems that may be used for distributed parallel processing.

Figure 15:
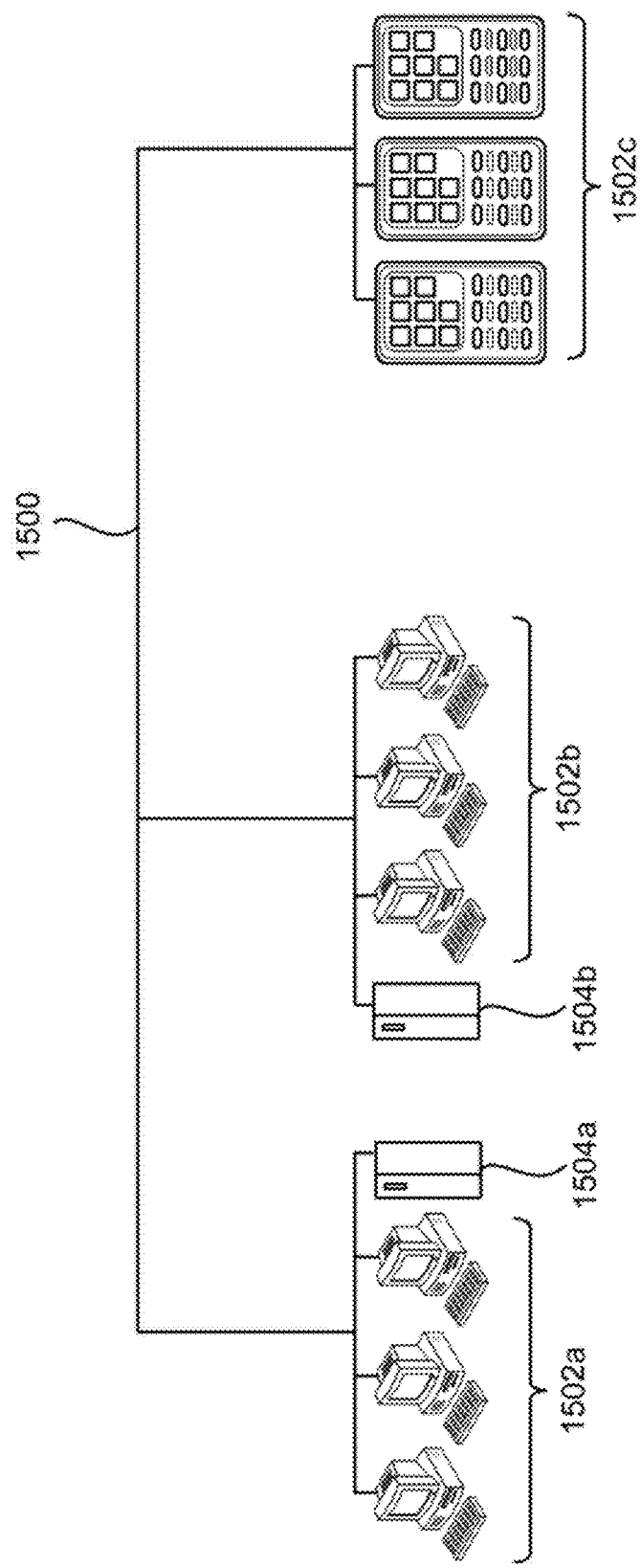
FIG. 15 is a diagram demonstrating a network configured to incorporate a plurality of computer systems, a plurality of cell phones and personal data assistants, and Network Attached Storage (NAS).

FIG. 15 is a diagram showing a network 1500 with a plurality of computer systems 1502a, and 1502b, a plurality of cell phones and personal data assistants 1502c, and Network Attached Storage (NAS) 1504a, and 1504b. In example instances, systems 1502a, 1502b, and 1502c may manage data storage and optimize data access for data stored in Network Attached Storage (NAS) 1504a and 1504b. A mathematical model may be used for the data and be evaluated using distributed parallel processing across computer systems 1502a, and 1502b, and cell phone and personal data assistant systems 1502c. Computer systems 1502a, and 1502b, and cell phone and personal data assistant systems 1502c may also provide parallel processing for adaptive data restructuring of the data stored in Network Attached Storage (NAS) 1504a and 1504b. FIG. 15 illustrates an example only, and a wide variety of other computer architectures and systems may be used in conjunction with the various instances of the present disclosure. For example, a blade server may be used to provide parallel processing. Processor blades may be connected through a back plane to provide parallel processing. Storage may also be connected to the back plane or as Network Attached Storage (NAS) through a separate network interface. In some example instances, processors may maintain separate memory spaces and transmit data through network interfaces, back plane or other connectors for parallel processing by other processors. In other instances, some or all of the processors may use a shared virtual address memory space.

Figure 16:
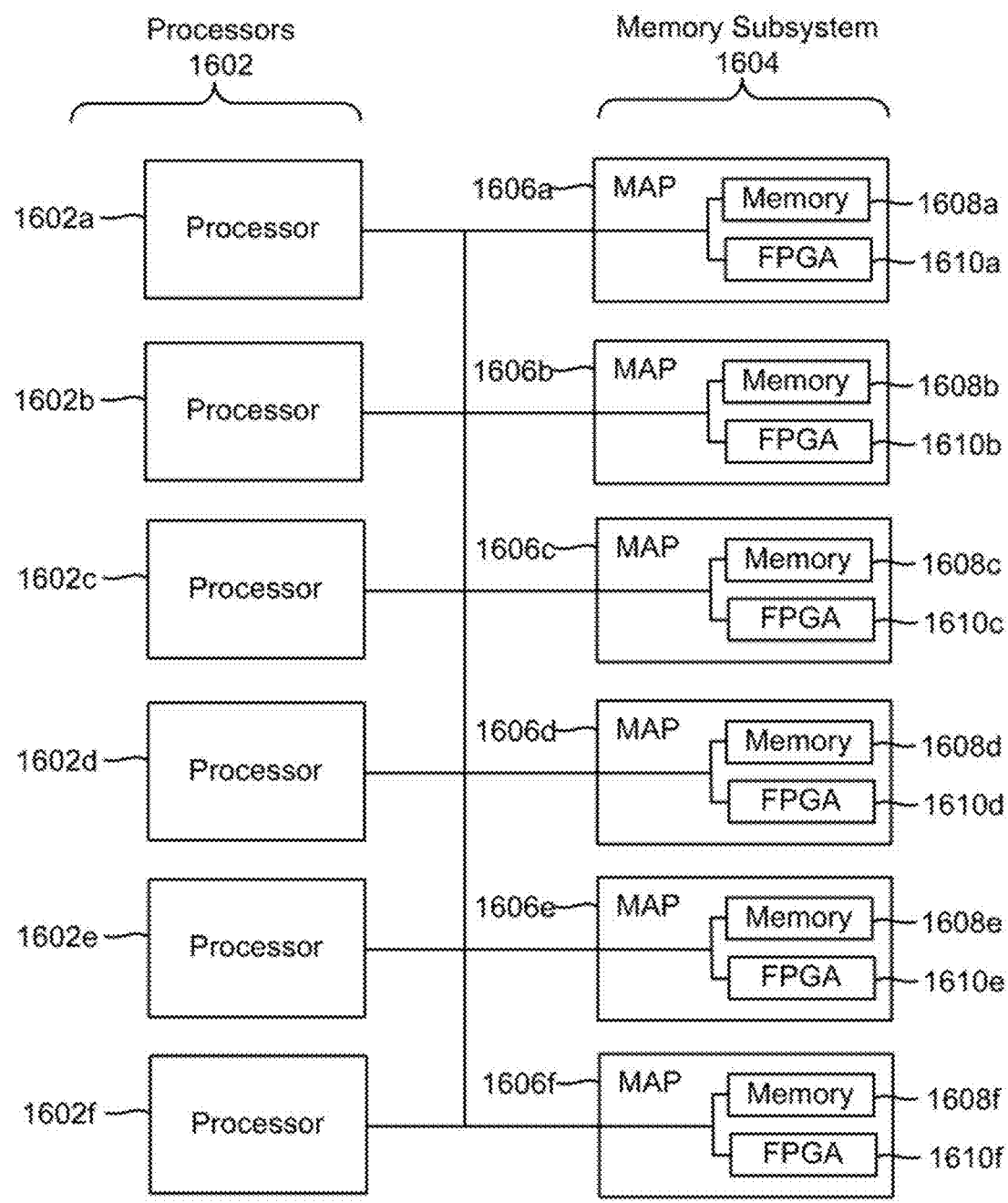
FIG. 16 is a block diagram of a multiprocessor computer system using a shared virtual address memory space.

FIG. 16 is a block diagram of a multiprocessor computer system 1600 using a shared virtual address memory space in accordance with an example instance. The system includes a plurality of processors 1602a-f that may access a shared memory subsystem 1604. The system incorporates a plurality of programmable hardware memory algorithm processors (MAPs) 1606a-f in the memory subsystem 1604. Each MAP 1606a-f may comprise a memory 1608a-f and one or more field programmable gate arrays (FPGAs) 1610a-f. The MAP provides a configurable functional unit and particular algorithms or portions of algorithms may be provided to the FPGAs 1610a-f for processing in close coordination with a respective processor. For example, the MAPs may be used to evaluate algebraic expressions regarding the data model and to perform adaptive data restructuring in example instances. In this example, each MAP is globally accessible by all of the processors for these purposes. In one configuration, each MAP may use Direct Memory Access (DMA) to access an associated memory 1608a-f, allowing it to execute tasks independently of, and asynchronously from the respective microprocessor 1602a-f. In this configuration, a MAP may feed results directly to another MAP for pipelining and parallel execution of algorithms.

The above computer architectures and systems are examples only, and a wide variety of other computer, cell phone, and personal data assistant architectures and systems may be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system may be implemented in software or hardware. Any variety of data storage media may be used in connection with example instances, including random access memory, hard drives, flash memory, tape drives, disk arrays, Network Attached Storage (NAS) and other local or distributed data storage devices and systems.

In example instances, the computer system may be implemented using software modules executing on any of the above or other computer architectures and systems. In other instances, the functions of the system may be implemented partially or completely in firmware, programmable logic devices such as field programmable gate arrays (FPGAs) as referenced in FIG. 16, system on chips (SOCs), application specific integrated circuits (ASICs), or other processing and logic elements. For example, the Set Processor and Optimizer may be implemented with hardware acceleration through the use of a hardware accelerator card, such as accelerator card 1422 illustrated in FIG. 14.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Functionalization of a Device Surface

A device was functionalized to support the attachment and synthesis of a library of oligonucleotides. The device surface was first wet cleaned using a piranha solution comprising 90% $H_2SO_4$ and 10% $H_2O_2$ for 20 minutes. The device was rinsed in several beakers with DI water, held under a DI water gooseneck faucet for 5 min, and dried with $N_2$. The device was subsequently soaked in $NH_4OH$ (1:100; 3 mL:300 mL) for 5 min, rinsed with DI water using a handgun, soaked in three successive beakers with DI water for 1 min each, and then rinsed again with DI water using the handgun. The device was then plasma cleaned by exposing the device surface to $O_2$. A SAMCO PC-300 instrument was used to plasma etch $O_2$ at 250 watts for 1 min in downstream mode.

The cleaned device surface was actively functionalized with a solution comprising N-(3-triethoxysilylpropyl)-4-hydroxybutyramide using a YES-1224P vapor deposition oven system with the following parameters: 0.5 to 1 torr, 60 min, 70° C., 135° C. vaporizer. The device surface was resist coated using a Brewer Science 200× spin coater. SPR™ 3612 photoresist was spin coated on the device at 2500 rpm for 40 sec. The device was pre-baked for 30 min at 90° C. on a Brewer hot plate. The device was subjected to photolithography using a Karl Suss MA6 mask aligner instrument. The device was exposed for 2.2 sec and developed for 1 min in MSF 26A. Remaining developer was rinsed with the handgun and the device soaked in water for 5 min. The device was baked for 30 min at 100° C. in the oven, followed by visual inspection for lithography defects using a Nikon L200. A descum process was used to remove residual resist using the SAMCO PC-300 instrument to $O_2$ plasma etch at 250 watts for 1 min.

The device surface was passively functionalized with a 100 μL solution of perfluorooctyltrichlorosilane mixed with 10 μL light mineral oil. The device was placed in a chamber, pumped for 10 min, and then the valve was closed to the pump and left to stand for 10 min. The chamber was vented to air. The device was resist stripped by performing two soaks for 5 min in 500 mL NMP at 70° C. with ultrasonication at maximum power (9 on Crest system). The device was then soaked for 5 min in 500 mL isopropanol at room temperature with ultrasonication at maximum power. The device was dipped in 300 mL of 200 proof ethanol and blown dry with $N_2$. The functionalized surface was activated to serve as a support for oligonucleotide synthesis.

Example 2: Synthesis of a 50-Mer Sequence on an Oligonucleotide Synthesis Device A two dimensional oligonucleotide synthesis device was assembled into a flowcell, which was connected to a flowcell (Applied Biosystems (ABI394 DNA Synthesizer")). The two-dimensional oligonucleotide synthesis device was uniformly functionalized with N-(3-TRIETHOXYSILYLPROPYL)-4-HYDROXYBUTYRAMIDE (Gelest) was used to synthesize an exemplary oligonucleotide of 50 bp ("50-mer oligonucleotide") using oligonucleotide synthesis methods described herein.

The sequence of the 50-mer was as described in SEQ ID NO.: 20. 5'AGACAATCAACCATTTGGGGTGGACAGC-CTTGACCTCTAGACTTCGGCAT##TTTTTTT TTT3' (SEQ ID NO.: 20), where # denotes Thymidine-succinyl hexamide CED phosphoramidite (CLP-2244 from Chem-Genes), which is a cleavable linker enabling the release of oligos from the surface during deprotection.

The synthesis was done using standard DNA synthesis chemistry (coupling, capping, oxidation, and deblocking) according to the protocol in Table 5 and an ABI synthesizer.

TABLE 5

Synthesis Protocol

General DNA Synthesis — Table 5

| Process Name | Process Step | Time (sec) |
|---|---|---|
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI 394 synthesizer to enable faster flow. Without flow restrictor, flow rates for amidites (0.1M in ACN), Activator, (0.25M Benzoylthiotetrazole ("BTT"; 30-3070-xx from GlenResearch) in ACN), and Ox (0.02M 12 in 20% pyridine, 10% water, and 70% THF) were roughly~100 uL/sec, for acetonitrile ("ACN") and capping reagents (1:1 mix of CapA and CapB, wherein CapA is acetic anhydride in THF/Pyridine and CapB is 16% 1-methylimidazole in THF), roughly~200 uL/sec, and for Deblock (3% dichloroacetic acid in toluene), roughly~300 uL/sec (compared to ~50 uL/sec for all reagents with flow restrictor). The time to completely push out Oxidizer was observed, the timing for chemical flow times was adjusted accordingly and an extra ACN wash was introduced between different chemicals. After oligonucleotide synthesis, the chip was deprotected in gaseous ammonia overnight at 75 psi. Five drops of water were applied to the surface to recover oligonucleotides. The recovered oligonucleotides were then analyzed on a BioAnalyzer small RNA chip (data not shown).

Example 3: Synthesis of a 100-Mer Sequence on an Oligonucleotide Synthesis Device The same process as described in Example 2 for the synthesis of the 50-mer sequence was used for the synthesis of a 100-mer oligonucleotide ("100-mer oligonucleotide"; 5' CGGGATCCTTATCGTCATCGTCGTACA-GATCCCGACCCATTTGCTGTCCACCAGTCATG CTAGCCATACCATGATGATGATGATGAGAACC CCGCAT##TTTTTTTTTT3', where # denotes Thymidine-succinyl hexamide CED phosphoramidite (CLP-2244 from ChemGenes); SEQ ID NO.: 21) on two different silicon chips, the first one uniformly functionalized with N-(3-TRIETHOXYSILYLPROPYL)-4-HYDROXYBUTYR-AMIDE and the second one functionalized with 5/95 mix of 11-acetoxyundecyltriethoxysilane and n-decyltriethoxysilane, and the oligonucleotides extracted from the surface were analyzed on a BioAnalyzer instrument (data not shown).

All ten samples from the two chips were further PCR amplified using a forward (5'ATGCGGGGTTCTCAT-CATC3'; SEQ ID NO.: 22) and a reverse (5'CGGGATCCT-TATCGTCATCG3'; SEQ ID NO.: 23) primer in a 50 uL PCR mix (25 uL NEB Q5 mastermix, 2.5 uL 10 uM Forward primer, 2.5 uL 10 uM Reverse primer, 1 uL oligonucleotide extracted from the surface, and water up to 50 uL) using the following thermalcycling program:

98° C., 30 sec
98° C., 10 sec; 63° C., 10 sec; 72° C., 10 sec; repeat 12 cycles
72° C., 2 min The PCR products were also run on a BioAnalyzer (data not shown), demonstrating sharp peaks at the 100-mer position. Next, the PCR amplified samples were cloned, and Sanger sequenced. Table 6 summarizes the results from the Sanger sequencing for samples taken from spots 1-5 from chip 1 and for samples taken from spots 6-10 from chip 2.

TABLE 6

Sequencing Results

| Spot | Error rate | Cycle efficiency |
|---|---|---|
| 1 | 1/763 bp | 99.87% |
| 2 | 1/824 bp | 99.88% |
| 3 | 1/780 bp | 99.87% |
| 4 | 1/429 bp | 99.77% |
| 5 | 1/1525 bp | 99.93% |
| 6 | 1/1615 bp | 99.94% |
| 7 | 1/531 bp | 99.81% |
| 8 | 1/1769 bp | 99.94% |

TABLE 6-continued

Sequencing Results

| Spot | Error rate | Cycle efficiency |
|---|---|---|
| 9 | 1/854 bp | 99.88% |
| 10 | 1/1451 bp | 99.93% |

Thus, the high quality and uniformity of the synthesized oligonucleotides were repeated on two chips with different surface chemistries. Overall, 89%, corresponding to 233 out of 262 of the 100-mers that were sequenced were perfect sequences with no errors.

Finally, Table 7 summarizes error characteristics for the sequences obtained from the oligonucleotides samples from spots 1-10.

TABLE 7

Error Characteristics

| | Sample ID/Spot no. | | | | | | | | | |
|---|---|---|---|---|---|---|---|---|---|---|
| | OSA_ 0046/1 | OSA_ 0047/2 | OSA_ 0048/3 | OSA_ 0049/4 | OSA_ 0050/5 | OSA_ 0051/6 | OSA_ 0052/7 | OSA_ 0053/8 | OSA_ 0054/9 | OSA_ 0055/10 |
| Total Sequences | 32 | 32 | 32 | 32 | 32 | 32 | 32 | 32 | 32 | 32 |
| Sequencing Quality | 25 of 28 | 27 of 27 | 26 of 30 | 21 of 23 | 25 of 26 | 29 of 30 | 27 of 31 | 29 of 31 | 28 of 29 | 25 of 28 |
| Oligo Quality | 23 of 25 | 25 of 27 | 22 of 26 | 18 of 21 | 24 of 25 | 25 of 29 | 22 of 27 | 28 of 29 | 26 of 28 | 20 of 25 |
| ROI Match Count | 2500 | 2698 | 2561 | 2122 | 2499 | 2666 | 2625 | 2899 | 2798 | 2348 |
| ROI Mutation | 2 | 2 | 1 | 3 | 1 | 0 | 2 | 1 | 2 | 1 |
| ROI Multi Base Deletion | 0 | 0 | 0 | 0 | 0 | 0 | 0 | 0 | 0 | 0 |
| ROI Small Insertion | 1 | 0 | 0 | 0 | 0 | 0 | 0 | 0 | 0 | 0 |
| ROI Single Base Deletion | 0 | 0 | 0 | 0 | 0 | 0 | 0 | 0 | 0 | 0 |
| Large Deletion Count | 0 | 0 | 1 | 0 | 0 | 1 | 1 | 0 | 0 | 0 |
| Mutation: G > A | 2 | 2 | 1 | 2 | 1 | 0 | 2 | 1 | 2 | 1 |
| Mutation: T > C | 0 | 0 | 0 | 1 | 0 | 0 | 0 | 0 | 0 | 0 |
| ROI Error Count | 3 | 2 | 2 | 3 | 1 | 1 | 3 | 1 | 2 | 1 |
| ROI Error Rate | Err: ~1 in 834 | Err: ~1 in 1350 | Err: ~1 in 1282 | Err: ~1 in 708 | Err: ~1 in 2500 | Err: ~1 in 2667 | Err: ~1 in 876 | Err: ~1 in 2900 | Err: ~1 in 1400 | Err: ~1 in 2349 |
| ROI Minus MP Primer Error Rate | MP Err: ~1 in 763 | MP Err: ~1 in 824 | MP Err: ~1 in 780 | MP Err: ~1 in 429 | MP Err: ~1 in 1525 | MP Err: ~1 in 1615 | MP Err: ~1 in 531 | MP Err: ~1 in 1769 | MP Err: ~1 in 854 | MP Err: ~1 in 1451 |

Example 4: Generation of a Nucleic Acid Library by Single-Site, Single Position Mutagenesis Oligonucleotide primers were de novo synthesized for use in a series of PCR reactions to generate a library of oligonucleotide variants of a template nucleic acid, see FIGS. 2A-2D. Four types of primers were generated in FIG. 2A: an outer 5' primer 215, an outer 3' primer 230, an inner 5' primer 225, and an inner 3' primer 220. The inner 5' primer/first oligonucleotide 220 and an inner 3' primer/second oligonucleotide 225 were generated using an oligonucleotide synthesis method as generally outlined in Table 6. The inner 5' primer/first oligonucleotide 220 represents a set of up to 19 primers of predetermined sequence, where each primer in the set differs from another at a single codon, in a single site of the sequence.

Oligonucleotide synthesis was performed on a device having at least two clusters, each cluster having 121 individually addressable loci.

The inner 5' primer 225 and the inner 3' primer 220 were synthesized in separate clusters. The inner 5' primer 225 was replicated 121 times, extending on 121 loci within a single cluster. For inner 3' primer 220, each of the 19 primers of variant sequences were each extended on 6 different loci, resulting in the extension of 114 oligonucleotides on 114 different loci.

Figure 17:
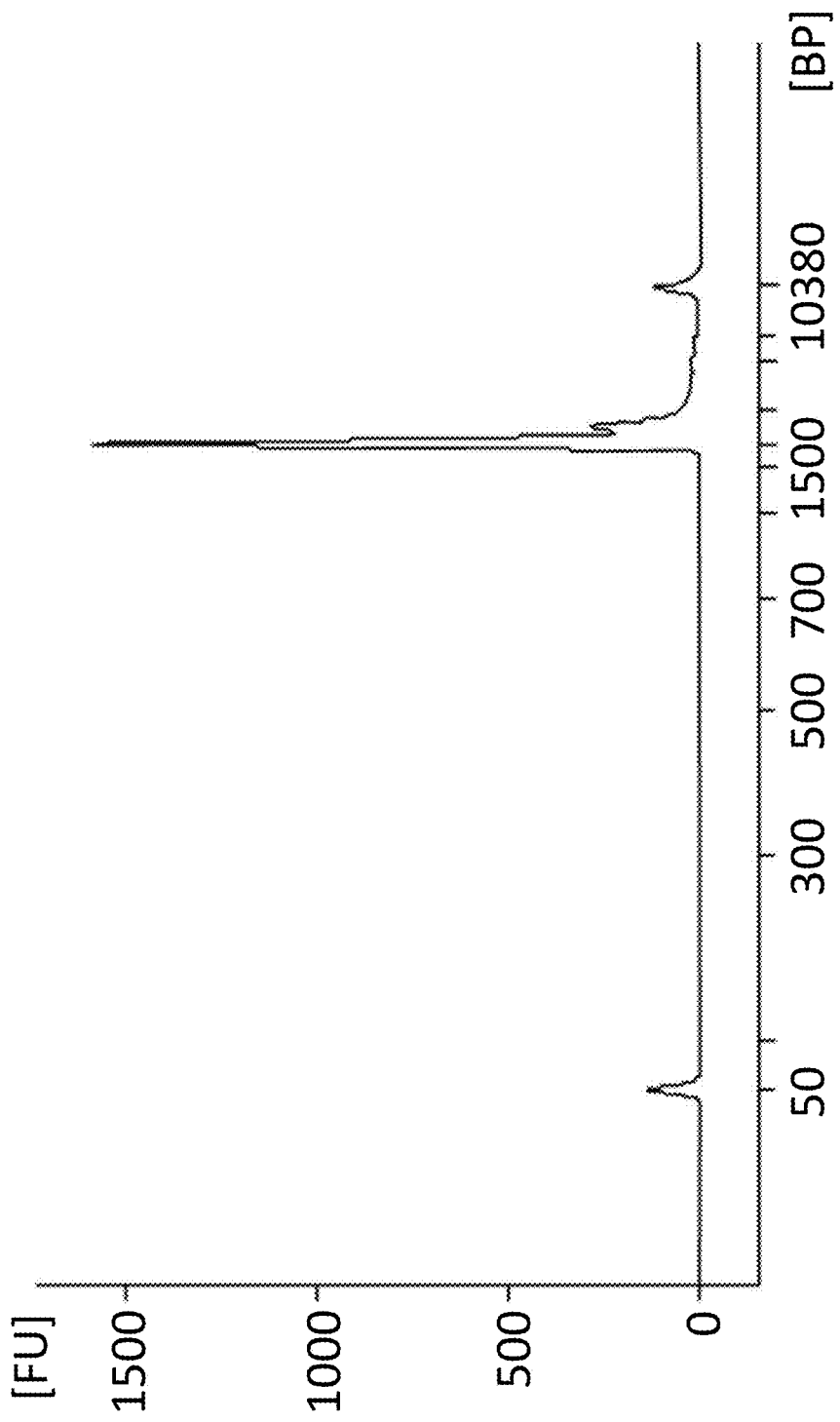
FIG. 17 depicts a BioAnalyzer plot of PCR reaction products resolved by gel electrophoresis.

Synthesized oligonucleotides were cleaved from the surface of the device and transferred to a plastic vial. A first PCR reaction was performed, using fragments of the long nucleic acid sequence 235, 240 to amplify the template nucleic acid, as illustrated in FIG. 2B. A second PCR reaction was performed using primer combination and the products of the first PCR reaction as a template, as illustrated in FIGS. 2C-2D. Analysis of the second PCR products was conducted on a BioAnalyzer, as shown in the trace of FIG. 17.

Figure 18:
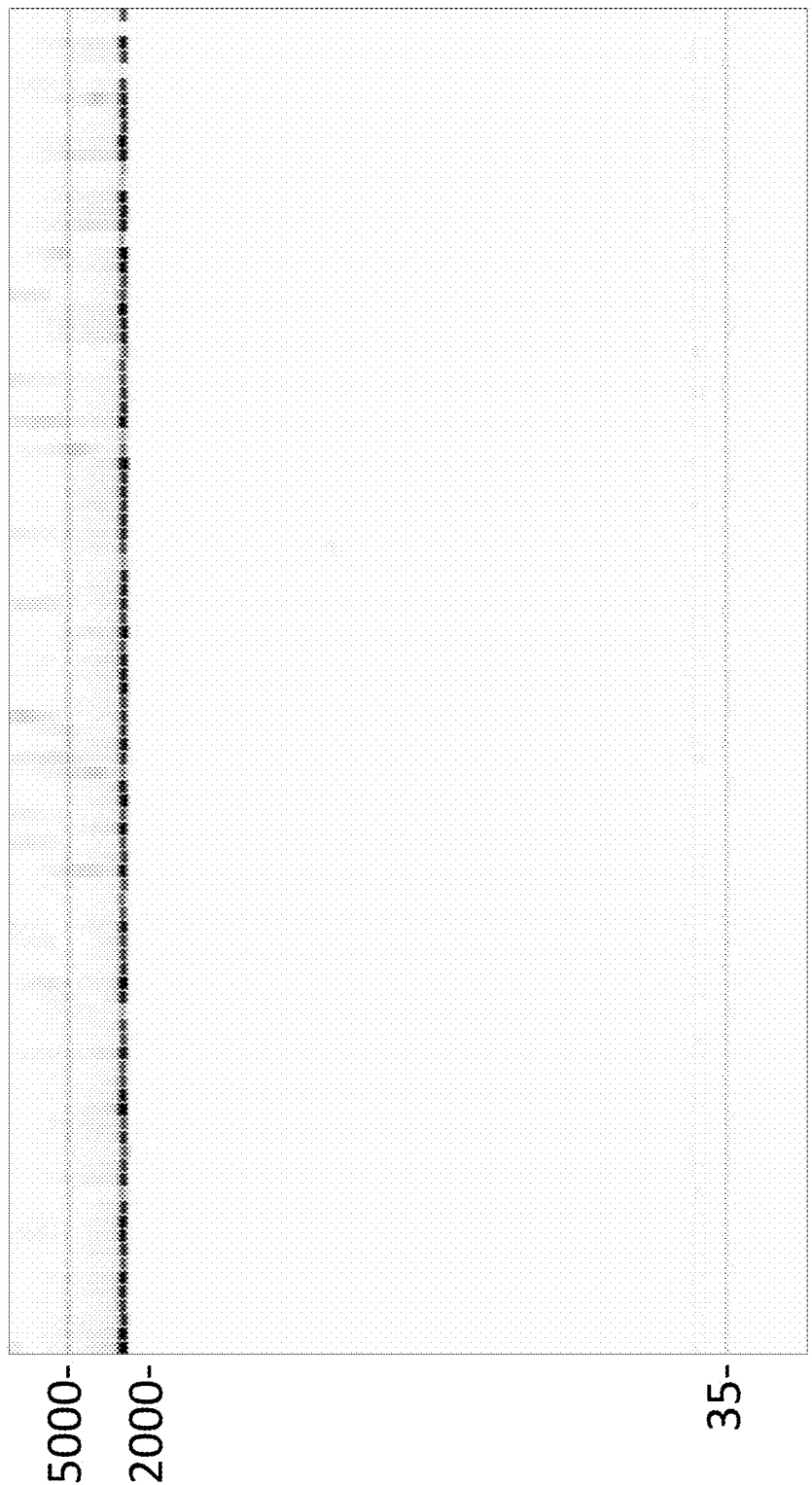
FIG. 18 depicts an electropherogram showing 96 sets of PCR products, each set of PCR products differing in sequence from a wild-type template nucleic acid at a single codon position, where the single codon position of each set is located at a different site in the wild-type template nucleic acid sequence. Each set of PCR products comprises 19 variant nucleic acids, each variant encoding for a different amino acid at their single codon position.

Example 5: Generation of a Nucleic Acid Library Comprising 96 Different Sets of Single Position Variants Four sets of primers, as generally shown in FIG. 2A and addressed in Example 2, were generated using de novo oligonucleotide synthesis. For the inner 5' primer 220, 96 different sets of primers were generated, each set of primers targeting a different single codon positioned within a single site of the template nucleic acid. For each set of primers, 19 different variants were generated, each variant comprising a codon encoding for a different amino acid at the single site. Two rounds of PCR were performed using the generated primers, as generally shown in FIGS. 2A-2D and described in Example 2. The 96 sets of amplification products were visualized in an electropherogram (FIG. 18), which was used to calculate a 100% amplification success rate.

Example 6: Generation of a Nucleic Acid Library Comprising 500 Different Sets of Single Position Variants Four sets of primers, as generally shown in FIG. 2A and addressed in Example 2, were generated using de novo oligonucleotide synthesis. For the inner 5' primer 220, 500 different sets of primers were generated, each set of primers targeting a different single codon positioned within a single site of the template nucleic acid. For each set of primers, 19 different variants were generated, each variant comprising a codon encoding for a different amino acid at the single site. Two rounds of PCR were performed using the generated primers, as generally shown in FIG. 2A and described in Example 2. Electropherograms display each of the 500 sets of PCR products having a population of nucleic acids with 19 variants at a different single site (data not shown). A comprehensive sequencing analysis of the library showed a greater than 99% success rate across preselected codon mutations (sequence trace and analysis data not shown).

Example 7: Single-Site Mutagenesis Primers for 1 Position

An example of codon variation design is provided in Table 8 for Yellow Fluorescent Protein. In this case, a single codon from a 50-mer of the sequence is varied 19 times. Variant nucleic acid sequence is indicated by bold letters. The wild type primer sequence is:

```
                                        (SEQ ID NO.: 1)
ATGGTGAGCAAGGGCGAGGAGCTGTTCACCGGGGTGGTGCCCAT.
```

In this case, the wild type codon encodes for valine, indicated by underline in SEQ ID NO.: 1. Therefore the 19 variants below exclude a codon encoding for valine. In an alternative example, if all triplets are to be considered, then all 60 variants would be generated, including an alternative sequence for the wild type codon.

TABLE 8

Variant Sequences

| SEQ ID NO. | Variant sequence | Variant codon |
|---|---|---|
| 2 | atgTTTAGCAAGGGCGAGGAGCTGTTCACCGGGGTGGTGCCCAT | F |
| 3 | atgTTAAGCAAGGGCGAGGAGCTGTTCACCGGGGTGGTGCCCAT | L |
| 4 | atgATTAGCAAGGGCGAGGAGCTGTTCACCGGGGTGGTGCCCAT | I |
| 5 | atgTCTAGCAAGGGCGAGGAGCTGTTCACCGGGGTGGTGCCCAT | S |
| 6 | atgCCTAGCAAGGGCGAGGAGCTGTTCACCGGGGTGGTGCCCAT | P |
| 7 | atgACTAGCAAGGGCGAGGAGCTGTTCACCGGGGTGGTGCCCAT | T |
| 8 | atgGCTAGCAAGGGCGAGGAGCTGTTCACCGGGGTGGTGCCCAT | A |
| 9 | atgTATAGCAAGGGCGAGGAGCTGTTCACCGGGGTGGTGCCCAT | Y |
| 10 | atgCATAGCAAGGGCGAGGAGCTGTTCACCGGGGTGGTGCCCAT | H |
| 11 | atgCAAAGCAAGGGCGAGGAGCTGTTCACCGGGGTGGTGCCCAT | Q |
| 12 | atgAATAGCAAGGGCGAGGAGCTGTTCACCGGGGTGGTGCCCAT | N |
| 13 | atgAAAAGCAAGGGCGAGGAGCTGTTCACCGGGGTGGTGCCCAT | K |
| 14 | atgGATAGCAAGGGCGAGGAGCTGTTCACCGGGGTGGTGCCCAT | D |
| 15 | atgGAAAGCAAGGGCGAGGAGCTGTTCACCGGGGTGGTGCCCAT | E |
| 16 | atgTGTAGCAAGGGCGAGGAGCTGTTCACCGGGGTGGTGCCCAT | C |
| 17 | atgTGGAGCAAGGGCGAGGAGCTGTTCACCGGGGTGGTGCCCAT | W |
| 18 | atgCGTAGCAAGGGCGAGGAGCTGTTCACCGGGGTGGTGCCCAT | R |
| 19 | atgGGTAGCAAGGGCGAGGAGCTGTTCACCGGGGTGGTGCCCAT | G |

Example 8: Single Site, Dual Position Nucleic Acid Variants

De novo oligonucleotide synthesis was performed under conditions similar to those described in Example 2. A single cluster on a device was generated which contained synthesized predetermined variants of a nucleic acid for 2 consecutive codon positions at a single site, each position being a codon encoding for an amino acid. In this arrangement, 19 variants/per position were generated for 2 positions with 3 replicates of each nucleic acid, resulting in 114 nucleic acids synthesized.

Example 9: Multiple Site, Dual Position Nucleic Acid Variants

De novo oligonucleotide synthesis was performed under conditions similar to those described in Example 2. A single cluster on a device was generated which contained synthesized predetermined variants of a nucleic acid for 2 non-consecutive codon positions, each position being a codon encoding for an amino acid. In this arrangement, 19 variants/per position were generated for 2 positions.

Example 10: Single Stretch, Triple Position Nucleic Acid Variants

De novo oligonucleotide synthesis was performed under conditions similar to those described in Example 2. A single cluster on a device was generated which contained synthesized predetermined variants of a reference nucleic acid for 3 consecutive codon positions. In the 3 consecutive codon position arrangement, 19 variants/per position were generated for 3 positions with 2 replicates of each nucleic acid, and resulted in 114 nucleic acids synthesized.

Example 11: Multiple Site, Triple Position Nucleic Acid Variants

De novo oligonucleotide synthesis was performed under conditions similar to those described in Example 2. A single cluster on a device was generated which contains synthesized predetermined variants of a reference nucleic acid for at least 3 non-consecutive codon positions. Within a predetermined region, the location of codons encoding for 3 histidine residues were varied.

Example 12: Multiple Site, Multiple Position Nucleic Acid Variants

De novo oligonucleotide synthesis was performed under conditions similar to those described in Example 2. A single cluster on a device was generated which contained synthesized predetermined variants of a reference nucleic acid for 1 or more codon positions in 1 or more stretches. Five positions were varied in the library. The first position encoded codons for a resultant 50/50 K/R ratio in the expressed protein; the second position encoded codons for a resultant 50/25/25 V/L/S ratio in the expressed protein, the third position encoded codons for a resultant a 50/25/25 Y/R/D ratio in the expressed protein, the fourth position encoded codons for a resultant an equal ratio for all amino acids in the expressed protein, and the fifth position encoded codons for a resultant a 75/25 G/P ratio in the expressed protein.

Example 13: Modular Plasmid Components for Expressing Diverse Peptides

A nucleic acid library is generated as in Examples 4-6 and 8-12, encoding for codon variation at a single site or multiple sites for each of separate regions that make up portions of an expression construct cassette, as depicted in FIG. 11. To generate a two construct expressing cassette, variant oligonucleotides were synthesized encoding at least a portion of a variant sequence of a first promoter 1110, first open reading frame 1120, first terminator 1130, second promoter 1140, second open reading frame 1150, or second terminator sequence 1160. After rounds of amplification, as described in previous examples, a library of 1,024 expression constructs is generated.

Example 14: Multiple Site, Single Position Variants

A nucleic acid library is generated as in Examples 4-6 and 8-12, encoding for codon variation at a single site or multiple sites in a region encoding for at least a portion of nucleic acid. A library of oligonucleotide variants is generated, wherein the library consists of multiple site, single position variants. See, for example, FIG. 6B.

Example 15: Variant Library Synthesis

De novo oligonucleotide synthesis is performed under conditions similar to those described in Example 2. At least 30,000 non-identical oligonucleotides are de novo synthesized, wherein each of the non-identical oligonucleotides encodes for a different codon variant of an amino acid sequence. The synthesized at least 30,000 non-identical oligonucleotides have an aggregate error rate of less than 1 in 1:000 bases compared to predetermined sequences for each of the at least 30,000 non-identical oligonucleotides. The library is used for PCR mutagenesis of a long nucleic acid and at least 30,000 non-identical variant nucleic acids are formed.

Example 16: Cluster-Based Variant Library Synthesis

De novo oligonucleotide synthesis is performed under conditions similar to those described in Example 2. A single cluster on a device is generated which contained synthesized predetermined variants of a reference oligonucleotide for 2 codon positions. In the 2 consecutive codon position arrangement, 19 variants/per position were generated for the 2 positions with 2 replicates of each oligonucleotide, and resulted in 38 oligonucleotides synthesized. Each variant sequence is 40 bases in length. In the same cluster, additional non-variant oligonucleotide sequences are generated, where the additional non-variant oligonucleotides and the variant oligonucleotides collective encode for 38 variants of the coding sequence of a gene. Each of the oligonucleotides has at least one region reverse complementary to another of the oligonucleotides. The oligonucleotides in the cluster are released by gaseous ammonia cleavage. A pin comprising water contacts the cluster, picks up the oligonucleotides, and moves the oligonucleotides to a small vial. The vial also contains DNA polymerase reagents for a polymerase cycling assembly (PCA) reaction. The oligonucleotides anneal, gaps are filled in by an extension reaction, and resultant double-stranded DNA molecules are formed, forming a variant nucleic acid library. The variant nucleic acid library is, optionally, subjected to restriction enzyme is then ligated into expression vectors.

Example 17: Generation of a Variant Nucleic Acid Library

CAR variant libraries are generated, as described in Examples 8-16, to have variance in an antigen recognition domain, a hinge domain, a transmembrane domain, or an intracellular domain compared to a reference sequence. Alternatively, CAR variant libraries are also generated to have variance in all domains of a CAR. The CAR variant libraries are screened against a known tumor antigen. Variant sequences that result in increased T cell activation and/or T cell binding are identified. The tumor antigen may be expressed on a primary cultured cell, non-primary cultured cell, or in a non-cellular setting, such as on a plate, beads, slurry, or column.

Example 18: Expression and Screening of a Variant CAR Library

The library of variant CAR genes described in Example 17 are transferred into mammalian cells to generate a library of cell populations, each cell population expressing a different CAR variant protein. The protein library is screened for CAR complexes with improved affinity (measure of the strength of interaction between an epitope and an antibody's antigen binding site) for a tumor antigen, such as HER2 or NY-ESO-1. Additional functional considerations, such as variant gene expression, avidity (measure of the overall strength of an antibody-antigen complex), stability, and target specificity are also assessed.

Example 19: Manufacturing and Delivery of Engineered T Cells

T cells are harvested from a subject diagnosed with cancer and are genetically engineered with a CAR selected after performing analysis in Example 18. After a brief period of in vitro expansion and passing of product-specific release criteria, the engineered T-cells are administered to the same subject.

Example 20: Variant Peptide Library

A nucleic acid library is generated as in Examples 4-6 and 8-12, encoding for codon variation at a single site or multiple sites for common tumor antigens. After rounds of amplification, as described in previous examples, libraries of 1,024 expression constructs for each of the antigen variants are generated. The libraries are transferred into mammalian cells to generate a library of cell populations and are screened for improved binding affinity and target specificity.

Example 21: Variant Peptide Library and Variant Library of CARs

A nucleic acid is generated as in Examples 4-6 and 8-12, encoding for codon variation at a single site or multiple sites for an antigen recognition domain of a CAR. A nucleic acid library is generated as in Example 20, encoding for codon variation at a single site or multiple sites for common tumor antigens. After rounds of amplification, as described in previous examples, libraries of 1,024 expression constructs for each of the CAR variants and the antigen variants are generated. The libraries are transferred into mammalian cells to generate a library of cell populations and are screened for improved binding affinity and target specificity.

Example 22: Variant CARs

A nucleic acid library is generated as in Examples 4-6 and 8-12 to generate nucleic acids encoding for variant CARs. Variants are generated at three sites to generate a library comprising about $10^3$ variant CARs.

The variant CARs are screened in vitro against tumor antigens for specificity of the variant CARs to the tumor antigen. Variant CARs that are highly specific for the tumor antigen are then further variegated to generate a second library. The second library comprises variation in residues located in the hinge domain, the transmembrane domain, or the intracellular domain of the CAR. The second library is expressed in cells and screened in vitro for a second improvement, for example, avidity, stability, affinity, or expression.

Select CAR genes or gene fragment variants having desired features after screening products from the first and/or second variant libraries are selected for development of a potential therapeutic.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

---

What is claimed is:

1. A method of synthesizing an oligonucleotide library, comprising:
   a. providing a first set of preselected oligonucleotide sequences encoding for at least 400 sequences of a chimeric antigen receptor gene or gene fragment, wherein each sequence comprises at least one variation of at least two preselected codons for an amino acid residue in an antigen recognition domain;
   b. synthesizing the first set of preselected oligonucleotide sequences; and
   c. screening a first activity for proteins encoded by the first set of oligonucleotide sequences, wherein the first activity is specificity, avidity, affinity, stability, or expression, wherein the first set of preselected oligonucleotides comprises all variations of the at least two preselected codons.

2. The method of claim 1, wherein each oligonucleotide is at least 50 bases or at least 100 bases in length.

3. The method of claim 1, wherein each sequence comprises at least one variation of at least three preselected codons.

4. The method of claim 1, wherein each sequence comprises at least one variation of four or more preselected codons.

5. The method of claim 1, wherein the at least two preselected codons are consecutive codons.

6. The method of claim 1, further comprising amplification of the first set of oligonucleotide sequences to generate a first library of expression constructs.

7. The method of claim 6, further comprising transferring the expression constructs into mammalian cells to generate a first library of cell populations expressing variant chimeric expression antigens.

8. The method of claim 1, wherein the chimeric antigen receptor gene or gene fragment is from a tumor antigen.

9. The method of claim 7, further comprising:
   a. screening the variant chimeric expression antigens for binding specificity;
   b. generating a second library of expression constructs from the variant chimeric expression antigens showing increased specificity; and
   c. transferring the second library of expression constructs to mammalian cells to generate a second library of cell populations expressing variant chimeric expression antigens.

10. The method of claim 1, further comprising:
    a. contacting the oligonucleotide sequences with DNA polymerase reagents to generate a polymerase cycling assembly (PCA) reaction;
    b. annealing the oligonucleotide sequences;
    c. filling gaps with an extension reaction; and
    d. ligating the oligonucleotide sequences into expression vectors.

11. A method of synthesizing an oligonucleotide library, comprising:
    a. providing a first set of preselected oligonucleotide sequences encoding for at least 400 sequences of a chimeric antigen receptor gene or gene fragment, wherein each sequence comprises at least one variation of at least two preselected codons for an amino acid residue in an antigen recognition domain; and
    b. synthesizing the first set of preselected oligonucleotide sequences, wherein the first set of preselected oligonucleotides comprises all variations of the at least two preselected codons.

12. The method of claim 11, wherein each oligonucleotide is at least 50 bases or at least 100 bases in length.

13. The method of claim 11, wherein the at least two preselected codons are consecutive codons.

* * * * *

SEQUENCE LISTING

<160> NUMBER OF SEQ ID NOS: 49

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
atggtgagca agggcgagga gctgttcacc ggggtggtgc ccat          44

```
<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atgtttagca agggcgagga gctgttcacc ggggtggtgc ccat            44

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgttaagca agggcgagga gctgttcacc ggggtggtgc ccat             44

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgattagca agggcgagga gctgttcacc ggggtggtgc ccat             44

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atgtctagca agggcgagga gctgttcacc ggggtggtgc ccat             44

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atgcctagca agggcgagga gctgttcacc ggggtggtgc ccat             44

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atgactagca agggcgagga gctgttcacc ggggtggtgc ccat             44
```

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atggctagca agggcgagga gctgttcacc ggggtggtgc ccat                    44

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atgtatagca agggcgagga gctgttcacc ggggtggtgc ccat                    44

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atgcatagca agggcgagga gctgttcacc ggggtggtgc ccat                    44

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atgcaaagca agggcgagga gctgttcacc ggggtggtgc ccat                    44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atgaatagca agggcgagga gctgttcacc ggggtggtgc ccat                    44

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atgaaaagca agggcgagga gctgttcacc ggggtggtgc ccat                    44

```
<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atggatagca agggcgagga gctgttcacc ggggtggtgc ccat                    44

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atggaaagca agggcgagga gctgttcacc ggggtggtgc ccat                    44

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atgtgtagca agggcgagga gctgttcacc ggggtggtgc ccat                    44

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
atgtggagca agggcgagga gctgttcacc ggggtggtgc ccat                    44

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atgcgtagca agggcgagga gctgttcacc ggggtggtgc ccat                    44

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atgggtagca agggcgagga gctgttcacc ggggtggtgc ccat                    44

<210> SEQ ID NO 20
```

```
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
agacaatcaa ccatttgggg tggacagcct tgacctctag acttcggcat tttttttttt    60
tt                                                                   62

<210> SEQ ID NO 21
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
cgggatcctt atcgtcatcg tcgtacagat cccgacccat tgctgtcca ccagtcatgc     60 tagccatacc atgatgatga tgatgatgag aaccccgcat tttttttttt tt           112

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atgcggggtt ctcatcatc                                                 19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgggatcctt atcgtcatcg                                                20

<210> SEQ ID NO 24
<211> LENGTH: 600
<212> TYPE: DNA
<213> ORGANISM: Homo sapiens

<400> SEQUENCE: 24
atgaagtcag gcctctggta tttctttctc ttctgcttgc gcattaaagt tttaacagga    60
gaaatcaatg gttctgccaa ttatgagatg tttatatttc acaacggagg tgtacaaatt   120
ttatgcaaat atcctgacat tgtccagcaa tttaaaatgc agttgctgaa agggggcaa    180 atactctgcg atctcactaa gacaaaagga agtggaaaca cagtgtccat taagagtctg   240
aaattctgcc attctcagtt atccaacaac agtgtctctt ttttctata caacttggac    300 cattctcatg ccaactatta cttctgcaac ctatcaattt ttgatcctcc tccttttaaa   360
gtaactctta caggaggata tttgcatatt tatgaatcac aactttgttg ccagctgaag   420
ttctggttac ccataggatg tgcagccttt gttgtagtct gcattttggg atgcatactt   480
atttgttggc ttacaaaaaa gaagtattca tccagtgtgc acgaccctaa cggtgaatac   540
```

| | |
|---|---|
| atgttcatga gagcagtgaa cacagccaaa aaatctagac tcacagatgt gaccctataa | 600 |

<210> SEQ ID NO 25
<211> LENGTH: 402
<212> TYPE: DNA
<213> ORGANISM: Homo sapiens

<400> SEQUENCE: 25

| | |
|---|---|
| atggtatcac atcggtatcc tcgaattcaa agtatcaaag tacaatttac cgaatataag | 60 |
| aaggagaaag gtttcatcct cacttcccaa aaggaggatg aaatcatgaa ggtgcagaac | 120 |
| aactcagtca tcatcaactg tgatgggttt tatctcatct ccctgaaggg ctacttctcc | 180 |
| caggaagtca acattagcct tcattaccag aaggatgagg agcccctctt ccaactgaag | 240 |
| aaggtcaggt ctgtcaactc cttgatggtg gcctctctga cttacaaaga caaagtctac | 300 |
| ttgaatgtga ccactgacaa tacctccctg gatgacttcc atgtgaatgg cggagaactg | 360 |
| attcttatcc atcaaaatcc tggtgaattc tgtgtccttt ga | 402 |

<210> SEQ ID NO 26
<211> LENGTH: 768
<212> TYPE: DNA
<213> ORGANISM: Homo sapiens

<400> SEQUENCE: 26

| | |
|---|---|
| atgggaaaca gctgttacaa catagtagcc actctgttgc tggtcctcaa ctttgagagg | 60 |
| acaagatcat tgcaggatcc ttgtagtaac tgcccagctg gtacattctg tgataataac | 120 |
| aggaatcaga tttgcagtcc ctgtcctcca aatagtttct ccagcgcagg tggacaaagg | 180 |
| acctgtgaca tatgcaggca gtgtaaaggt gttttcagga ccaggaagga gtgttcctcc | 240 |
| accagcaatg cagagtgtga ctgcactcca gggtttcact gcctgggggc aggatgcagc | 300 |
| atgtgtgaac aggattgtaa acaaggtcaa gaactgacaa aaaaaggttg taaagactgt | 360 |
| tgctttggga catttaacga tcagaaacgt ggcatctgtc gaccctggac aaactgttct | 420 |
| ttggatggaa agtctgtgct tgtgaatggg acgaaggaga gggacgtggt ctgtggacca | 480 |
| tctccagccg acctctctcc gggagcatcc tctgtgaccc cgcctgcccc tcgagagag | 540 |
| ccaggacact ctccgcagat catctccttc tttcttgcgc tgacgtcgac tgcgttgctc | 600 |
| ttcctgctgt tcttcctcac gctccgtttc tctgttgtta acggggcag aaagaaactc | 660 |
| ctgtatatat tcaaacaacc atttatgaga ccagtacaaa ctactcaaga ggaagatggc | 720 |
| tgtagctgcc gatttccaga agaagaagaa ggaggatgtg aactgtga | 768 |

<210> SEQ ID NO 27
<211> LENGTH: 783
<212> TYPE: DNA
<213> ORGANISM: Homo sapiens

<400> SEQUENCE: 27

| | |
|---|---|
| atggcacggc cacatccctg gtggctgtgc gttctgggga ccctggtggg gctctcagct | 60 |
| actccagccc ccaagagctg cccagagagg cactactggg ctcagggaaa gctgtgctgc | 120 |
| cagatgtgtg agccaggaac attcctcgtg aaggactgta ccagcatag aaaggctgct | 180 |
| cagtgtgatc cttgcatacc gggggtctcc ttctctcctg accaccacac ccggccccac | 240 |
| tgtgagagct gtcggcactg taactctggt cttctcgttc gcaactgcac catcactgcc | 300 |
| aatgctgagt gtgcctgtcg caatggctgg cagtgcaggg acaaggagtg caccgagtgt | 360 |

```
gatcctcttc caaacccttc gctgaccgct cggtcgtctc aggccctgag cccacaccct    420
cagcccaccc acttacctta tgtcagtgag atgctggagg ccaggacagc tgggcacatg    480
cagactctgg ctgacttcag gcagctgcct gcccggactc tctctaccca ctggccaccc    540
caaagatccc tgtgcagctc cgatttatt cgcatccttg tgatcttctc tggaatgttc     600
cttgttttca ccctggccgg ggccctgttc ctccatcaac gaaggaaata tagatcaaac    660
aaaggagaaa gtcctgtgga gcctgcagag ccttgtcgtt acagctgccc cagggaggag    720
gagggcagca ccatccccat ccaggaggat taccgaaaac cggagcctgc ctgctccccc    780
tga                                                                  783
```

```
<210> SEQ ID NO 28
<211> LENGTH: 708
<212> TYPE: DNA
<213> ORGANISM: Homo sapiens

<400> SEQUENCE: 28
atggccttac cagtgaccgc cttgctcctg ccgctggcct tgctgctcca cgccgccagg     60
ccgagccagt tccgggtgtc gccgctggat cggacctgga acctgggcga cacagtggag    120
ctgaagtgcc aggtgctgct gtccaacccg acgtcgggcg gctcgtggct cttccagccg    180
cgcggcgccg ccgccagtcc caccttcctc ctatacctct cccaaaacaa gcccaaggcg    240
gccgaggggc tggacaccca gcggttctcg ggcaagaggt tggggacac cttcgtcctc    300 accctgagcg acttccgccg agagaacgag ggctactatt tctgctcggc cctgagcaac   360
tccatcatgt acttcagcca cttcgtgccg gtcttcctgc cagcgaagcc caccacgacg    420
ccagcgccgc gaccaccaac accggcgccc accatcgcgt cgcagcccct gtccctgcgc    480
ccagaggcgt gccggccagc ggcgggggc gcagtgcaca cgagggggct ggacttcgcc     540
tgtgatatct acatctgggc gcccttggcc gggacttgtg gggtccttct cctgtcactg    600
gttatcaccc tttactgcaa ccacaggaac cgaagacgtg tttgcaaatg tccccggcct    660
gtggtcaaat cgggagacaa gcccagcctt cggcgagat acgtctaa                   708
```

```
<210> SEQ ID NO 29
<211> LENGTH: 282
<212> TYPE: DNA
<213> ORGANISM: Homo sapiens

<400> SEQUENCE: 29
atgatccatc tgggtcacat cctcttcctg cttttgctcc cagtggctgc agctcagacg     60
actccaggag agagatcatc actccctgcc ttttaccctg gcacttcagg ctcttgttcc    120
ggatgtgggt ccctctctct gccgctcctg gcaggcctcg tggctgctga tgcggtggca    180
tcgctgctca tcgtggggc ggtgttcctg tgcgcacgcc cacgccgcag ccccgcccaa     240
gaagatggca aagtctacat caacatgcca ggcaggggct ga                       282
```

```
<210> SEQ ID NO 30
<211> LENGTH: 549
<212> TYPE: DNA
<213> ORGANISM: Homo sapiens

<400> SEQUENCE: 30
atggaacagg ggaagggcct ggctgtcctc atcctggcta tcattcttct tcaaggtact     60
ttggcccagt caatcaaagg aaaccacttg gttaaggtgt atgactatca agaagatggt    120
tcggtacttc tgacttgtga tgcagaagcc aaaaatatca catggtttaa agatgggaag    180
```

```
atgatcggct tcctaactga agataaaaaa aaatggaatc tgggaagtaa tgccaaggac    240
cctcgaggga tgtatcagtg taaaggatca cagaacaagt caaaaccact ccaagtgtat    300
tacagaatgt gtcagaactg cattgaacta aatgcagcca ccatatctgg ctttctcttt    360
gctgaaatcg tcagcatttt cgtccttgct gttggggtct acttcattgc tggacaggat    420
ggagttcgcc agtcgagagc ttcagacaag cagactctgt tgcccaatga ccagctctac    480
cagcccctca aggatcgaga agatgaccag tacagccacc ttcaaggaaa ccagttgagg    540
aggaattga                                                            549

<210> SEQ ID NO 31
<211> LENGTH: 624
<212> TYPE: DNA
<213> ORGANISM: Homo sapiens

<400> SEQUENCE: 31
atgcagtcgg gcactcactg gagagttctg ggcctctgcc tcttatcagt tggcgtttgg     60
gggcaagatg gtaatgaaga aatgggtggt attacacaga caccatataa agtctccatc    120
tctggaacca cagtaatatt gacatgccct cagtatcctg gatctgaaat actatggcaa    180
cacaatgata aaaacatagg cggtgatgag gatgataaaa acataggcag tgatgaggat    240
cacctgtcac tgaaggaatt ttcagaattg gagcaaagtg gttattatgt ctgctacccc    300
agaggaagca aaccagaaga tgcgaacttt tatctctacc tgagggcaag agtgtgtgag    360
aactgcatgg agatggatgt gatgtcggtg gccacaattg tcatagtgga catctgcatc    420
actgggggct tgctgctgct ggtttactac tggagcaaga atagaaaggc caaggccaag    480
cctgtgacac gaggagcggg tgctggcggc aggcaaaggg gacaaaacaa ggagaggcca    540
ccacctgttc ccaacccaga ctatgagccc atccggaaag ccagcgggga cctgtattct    600
ggcctgaatc agagacgcat ctga                                           624

<210> SEQ ID NO 32
<211> LENGTH: 681
<212> TYPE: DNA
<213> ORGANISM: Homo sapiens

<400> SEQUENCE: 32
atgcctgggg gtccaggagt cctccaagct ctgcctgcca ccatcttcct cctcttcctg     60
ctgtctgctg tctacctggg ccctgggtgc caggccctgt ggatgcacaa ggtcccagca    120
tcattgatgg tgagcctggg ggaagacgcc cacttccaat gcccgcacaa tagcagcaac    180
aacgccaacg tcacctggtg gcgcgtcctc catggcaact acacgtggcc ccctgagttc    240
ttgggcccgg gcgaggaccc caatggtacg ctgatcatcc agaatgtgaa caagagccat    300
gggggcatat acgtgtgccg ggtccaggag ggcaacagtt cataccagca gtcctgcggc    360
acctacctcc gcgtgcgcca gccgcccccc aggcccttcc tggacatggg ggagggcacc    420
aagaaccgaa tcatcacagc cgaggggatc atcctcctgt tctgcgcggt ggtgcctggg    480
acgctgctgc tgttcaggaa acgatggcag aacgagaagc tcgggttgga tgccgggggat    540 gaatatgaag atgaaaacct ttatgaaggc ctgaacctgg acgactgctc catgtatgag    600
gacatctccc ggggcctcca gggcacctac caggatgtgg gcagcctcaa cataggagat    660
gtccagctgg agaagccgtg a                                              681

<210> SEQ ID NO 33
```

<211> LENGTH: 1280
<212> TYPE: DNA
<213> ORGANISM: Homo sapiens

<400> SEQUENCE: 33

| | | | | | |
|---|---|---|---|---|---|
| agggacagg | ctgcagccgg | tgcagttaca | cgttttcctc | caaggagcct | cggacgttgt | 60 |
| cacgggtttg | gggtcgggga | cagagcggtg | accatggcca | ggctggcgtt | gtctcctgtg | 120 |
| cccagccact | ggatggtggc | gttgctgctg | ctgctctcag | ctgagccagt | accagcagcc | 180 |
| agatcggagg | accggtaccg | gaatcccaaa | ggtagtgctt | gttcgcggat | ctggcagagc | 240 |
| ccacgtttca | tagccaggaa | acggggcttc | acggtgaaaa | tgcactgcta | catgaacagc | 300 |
| gcctccggca | atgtgagctg | gctctggaag | caggagatgg | acgagaatcc | ccagcagctg | 360 |
| aagctggaaa | agggccgcat | ggaagagtcc | cagaacgaat | ctctcgccac | cctcaccatc | 420 |
| caaggcatcc | ggtttgagga | caatggcatc | tacttctgtc | agcagaagtg | caacaacacc | 480 |
| tcggaggtct | accagggctg | cggcacagag | ctgcgagtca | tgggattcag | caccttggca | 540 |
| cagctgaagc | agaggaacac | gctgaaggat | ggtatcatca | tgatccagac | gctgctgatc | 600 |
| atcctcttca | tcatcgtgcc | tatcttcctg | ctgctggaca | aggatgacag | caaggctggc | 660 |
| atggaggaag | atcacaccta | cgagggcctg | acattgacc | agacagccac | ctatgaggac | 720 |
| atagtgacgc | tgcggacagg | ggaagtgaag | tggtctgtag | gtgagcaccc | aggccaggag | 780 |
| tgagagccag | gtcgccccat | gacctgggtg | caggctccct | ggcctcagtg | actgcttcgg | 840 |
| agctgcctgg | ctcatggccc | aaccccttc | ctggaccccc | cagctggcct | ctgaagctgg | 900 |
| cccaccagag | ctgccatttg | tctccagccc | ctggtcccca | gctcttgcca | aagggcctgg | 960 |
| agtagaagga | caacagggca | gcaacttgga | gggagttctc | tggggatgga | cgggacccag | 1020 |
| ccttctgggg | gtgctatgag | gtgatccgtc | cccacacatg | ggatggggga | ggcagagact | 1080 |
| ggtccagagc | ccgcaaatgg | actcggagcc | gagggcctcc | cagcagagct | tgggaagggc | 1140 |
| catgaccca | actgggcccc | agaagagcca | caggaacatc | attcctctcc | cgcaaccact | 1200 |
| cccacccag | ggaggccctg | gcctccagtg | ccttcccccg | tggaataaac | ggtgtgtcct | 1260 |
| gagaaaccac | acaaaaaaaa | | | | | 1280 |

<210> SEQ ID NO 34
<211> LENGTH: 495
<212> TYPE: DNA
<213> ORGANISM: Homo sapiens

<400> SEQUENCE: 34

| | | | | | |
|---|---|---|---|---|---|
| atgaagtgga | aggcgctttt | caccgcggcc | atcctgcagg | cacagttgcc | gattacagag | 60 |
| gcacagagct | ttggcctgct | ggatcccaaa | ctctgctacc | tgctggatgg | aatcctcttc | 120 |
| atctatggtg | tcattctcac | tgccttgttc | ctgagagtga | agttcagcag | gagcgcagac | 180 |
| gcccccgcgt | accagcaggg | ccagaaccag | ctctataacg | agctcaatct | aggacgaaga | 240 |
| gaggagtacg | atgttttgga | caagagacgt | ggccggacc | ctgagatggg | gggaaagccg | 300 |
| cagagaagga | agaaccctca | ggaaggcctg | tacaatgaac | tgcagaaaga | taagatggcg | 360 |
| gaggcctaca | gtgagattgg | gatgaaaggc | gagcgccgga | ggggcaaggg | gcacgatggc | 420 |
| ctttaccagg | gtctcagtac | agccaccaag | gacacctacg | acgcccttca | catgcaggcc | 480 |
| ctgccccctc | gctaa | | | | | 495 |

<210> SEQ ID NO 35
<211> LENGTH: 9

```
<212> TYPE: PRT
<213> ORGANISM: Homo sapiens

<400> SEQUENCE: 35

Lys Val Ser Ala Val Thr Leu Ala Tyr
1               5

<210> SEQ ID NO 36
<211> LENGTH: 9
<212> TYPE: PRT
<213> ORGANISM: Homo sapiens

<400> SEQUENCE: 36

Arg Pro Lys Ser Asn Ile Val Leu Leu
1               5

<210> SEQ ID NO 37
<211> LENGTH: 9
<212> TYPE: PRT
<213> ORGANISM: Homo sapiens

<400> SEQUENCE: 37

Ile Met Ile Gly Val Leu Val Gly Val
1               5

<210> SEQ ID NO 38
<211> LENGTH: 9
<212> TYPE: PRT
<213> ORGANISM: Homo sapiens

<400> SEQUENCE: 38

Ile Ile Ser Ala Val Val Gly Ile Leu
1               5

<210> SEQ ID NO 39
<211> LENGTH: 9
<212> TYPE: PRT
<213> ORGANISM: Homo sapiens

<400> SEQUENCE: 39

Ser Leu Leu Met Trp Ile Thr Gln Val
1               5

<210> SEQ ID NO 40
<211> LENGTH: 9
<212> TYPE: PRT
<213> ORGANISM: Homo sapiens

<400> SEQUENCE: 40

Lys Tyr Ala Asp Lys Ile Tyr Ser Ile
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 41

His His His His His His
1               5

<210> SEQ ID NO 42
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Trp Ile Lys Arg Glu Gln
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 43

Xaa Trp Ile Lys Arg Glu Gln
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 44

Ala Xaa Ile Lys Arg Glu Gln
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 45

Ala Trp Xaa Lys Arg Glu Gln
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
```

```
<400> SEQUENCE: 46

Ala Trp Ile Xaa Arg Glu Gln
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 47

Ala Trp Ile Lys Xaa Glu Gln
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid

<400> SEQUENCE: 48

Ala Trp Ile Lys Arg Xaa Gln
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid

<400> SEQUENCE: 49

Ala Trp Ile Lys Arg Glu Xaa
1               5
```